(12) United States Patent
Weaver et al.

(10) Patent No.: US 10,403,830 B2
(45) Date of Patent: *Sep. 3, 2019

(54) ORGANIC ELECTROLUMINESCENT MATERIALS AND DEVICES

(71) Applicant: Universal Display Corporation, Ewing, NJ (US)

(72) Inventors: Michael S. Weaver, Princeton, NJ (US); Nicholas J. Thompson, Trenton, NJ (US); Jason Brooks, Philadelphia, PA (US); Geza Szigethy, Ewing, NJ (US); Glenn Morello, Pittsburgh, PA (US); Jun Deng, Murrysville, PA (US); Peter I. Djurovich, Long Beach, CA (US); Hsiao-Fan Chen, Lawrenceville, NJ (US)

(73) Assignee: Universal Display Corporation, Ewing, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/399,724

(22) Filed: Jan. 5, 2017

(65) Prior Publication Data

US 2017/0162802 A1 Jun. 8, 2017

Related U.S. Application Data

(63) Continuation-in-part of application No. 14/933,684, filed on Nov. 5, 2015, which is a continuation-in-part of application No. PCT/US2015/029269, filed on May 5, 2015.

(60) Provisional application No. 62/082,970, filed on Nov. 21, 2014, provisional application No. 61/990,239, filed on May 8, 2014, provisional application No. 62/251,447, filed on Nov. 5, 2015.

(51) Int. Cl.

| | | |
|---|---|---|
| *H01L 51/54* | (2006.01) | |
| *C09K 11/06* | (2006.01) | |
| *H01L 51/00* | (2006.01) | |
| *C07F 15/00* | (2006.01) | |
| *C07D 471/16* | (2006.01) | |
| *C07D 498/16* | (2006.01) | |
| *C07D 513/16* | (2006.01) | |
| *C09K 11/02* | (2006.01) | |
| *H01L 51/50* | (2006.01) | |

(52) U.S. Cl.
CPC ........ *H01L 51/0085* (2013.01); *C07D 471/16* (2013.01); *C07D 498/16* (2013.01); *C07D 513/16* (2013.01); *C07F 15/0033* (2013.01); *C09K 11/025* (2013.01); *C09K 11/06* (2013.01); *H01L 51/0087* (2013.01); *C09K 2211/1007* (2013.01); *C09K 2211/1011* (2013.01); *C09K 2211/1022* (2013.01); *C09K 2211/1029* (2013.01); *C09K 2211/1044* (2013.01); *C09K 2211/1088* (2013.01); *C09K 2211/185* (2013.01); *H01L 51/5016* (2013.01)

(58) Field of Classification Search
CPC ... C09K 11/06; C09K 11/025; C09K 2211/00; C09K 2211/10; C09K 2211/1007; C09K 2211/1011; C09K 2211/1022; C09K 2211/1029; C09K 2211/1044; C09K 2211/1088; C09K 2211/185; C07D 471/16; C07D 498/16; C07D 513/16; C07F 7/00; C07F 7/1852; C07F 15/00; C07F 15/0033; C07F 15/0086; H01L 27/32; H01L 51/0032; H01L 51/005; H01L 51/0071; H01L 51/0072; H01L 51/0073; H01L 51/0074; H01L 51/0085; H01L 51/0087; H01L 51/0086; H01L 51/50; H01L 51/5012; H01L 51/5016; H01L 51/5206; H01L 51/5221
USPC ....... 428/690, 691, 917, 411.4, 336; 427/58, 427/66; 313/500–512; 257/40, 88–104, 257/E51.001–E51.052; 252/301.16–301.35

See application file for complete search history.

(56) References Cited

U.S. PATENT DOCUMENTS

| | | | |
|---|---|---|---|
| 4,769,292 | A | 9/1988 | Tang et al. |
| 5,061,569 | A | 10/1991 | VanSlyke et al. |
| 5,247,190 | A | 9/1993 | Friend et al. |
| 5,703,436 | A | 12/1997 | Forrest et al. |
| 5,707,745 | A | 1/1998 | Forrest et al. |
| 5,834,893 | A | 11/1998 | Bulovic et al. |
| 5,844,363 | A | 12/1998 | Gu et al. |

(Continued)

FOREIGN PATENT DOCUMENTS

| | | |
|---|---|---|
| EP | 0650955 | 5/1995 |
| EP | 1725079 | 11/2006 |

(Continued)

OTHER PUBLICATIONS

Extended European Search Report dated Aug. 31, 2016 for corresponding European Application No. 16001000.5.

(Continued)

*Primary Examiner* — Andrew K Bohaty
(74) *Attorney, Agent, or Firm* — Duane Morris LLP

(57) ABSTRACT

An organic light emitting device (OLED) is provided. The OLED has an anode, a cathode, and an emission layer, disposed between the anode and the cathode, including a first emitting compound; wherein the first emitting compound is capable of functioning as a blue phosphorescent emitter in the OLED at room temperature; wherein the first emitting compound has PLQY of less than 90% at room temperature; wherein the OLED has an external quantum efficiency of between 8% and 20% at 1 mA/cm².

19 Claims, 14 Drawing Sheets

(56) References Cited

U.S. PATENT DOCUMENTS

| | | |
|---|---|---|
| 6,013,982 A | 1/2000 | Thompson et al. |
| 6,087,196 A | 7/2000 | Sturm et al. |
| 6,091,195 A | 7/2000 | Forrest et al. |
| 6,097,147 A | 8/2000 | Baldo et al. |
| 6,294,398 B1 | 9/2001 | Kim et al. |
| 6,303,238 B1 | 10/2001 | Thompson et al. |
| 6,337,102 B1 | 1/2002 | Forrest et al. |
| 6,468,819 B1 | 10/2002 | Kim et al. |
| 6,528,187 B1 | 3/2003 | Okada |
| 6,687,266 B1 | 2/2004 | Ma et al. |
| 6,835,469 B2 | 12/2004 | Kwong et al. |
| 6,921,915 B2 | 7/2005 | Takiguchi et al. |
| 7,087,321 B2 | 8/2006 | Kwong et al. |
| 7,090,928 B2 | 8/2006 | Thompson et al. |
| 7,154,114 B2 | 12/2006 | Brooks et al. |
| 7,250,226 B2 | 7/2007 | Tokito et al. |
| 7,279,704 B2 | 10/2007 | Walters et al. |
| 7,332,232 B2 | 2/2008 | Ma et al. |
| 7,338,722 B2 | 3/2008 | Thompson et al. |
| 7,393,599 B2 | 7/2008 | Thompson et al. |
| 7,396,598 B2 | 7/2008 | Takeuchi et al. |
| 7,431,968 B1 | 10/2008 | Shtein et al. |
| 7,445,855 B2 | 11/2008 | Mackenzie et al. |
| 7,534,505 B2 | 5/2009 | Lin et al. |
| 2002/0034656 A1 | 3/2002 | Thompson et al. |
| 2002/0134984 A1 | 9/2002 | Igarashi |
| 2002/0158242 A1 | 10/2002 | Son et al. |
| 2003/0138657 A1 | 7/2003 | Li et al. |
| 2003/0152802 A1 | 8/2003 | Tsuboyama et al. |
| 2003/0162053 A1 | 8/2003 | Marks et al. |
| 2003/0175553 A1 | 9/2003 | Thompson |
| 2003/0230980 A1 | 12/2003 | Forrest et al. |
| 2004/0036077 A1 | 2/2004 | Ise |
| 2004/0137267 A1 | 7/2004 | Igarashi et al. |
| 2004/0137268 A1 | 7/2004 | Igarashi et al. |
| 2004/0174116 A1 | 9/2004 | Lu et al. |
| 2004/0247933 A1 | 12/2004 | Thoms |
| 2005/0025993 A1 | 2/2005 | Thompson et al. |
| 2005/0112407 A1 | 5/2005 | Ogasawara et al. |
| 2005/0238919 A1 | 10/2005 | Ogasawara |
| 2005/0244673 A1 | 11/2005 | Satoh et al. |
| 2005/0260441 A1 | 11/2005 | Thompson et al. |
| 2005/0260449 A1 | 11/2005 | Walters et al. |
| 2006/0008670 A1 | 1/2006 | Lin et al. |
| 2006/0202194 A1 | 9/2006 | Jeong et al. |
| 2006/0240279 A1 | 10/2006 | Adamovich et al. |
| 2006/0251923 A1 | 11/2006 | Lin et al. |
| 2006/0263635 A1 | 11/2006 | Ise |
| 2006/0280965 A1 | 12/2006 | Kwong et al. |
| 2007/0082284 A1 | 4/2007 | Stoessel et al. |
| 2007/0190359 A1* | 8/2007 | Knowles ............ C07F 15/0033 428/690 |
| 2007/0278938 A1 | 12/2007 | Yabunouchi et al. |
| 2008/0015355 A1 | 1/2008 | Schafer et al. |
| 2008/0018221 A1 | 1/2008 | Egen et al. |
| 2008/0106190 A1 | 5/2008 | Yabunouchi et al. |
| 2008/0124572 A1 | 5/2008 | Mizuki et al. |
| 2008/0220265 A1 | 9/2008 | Xia et al. |
| 2008/0297033 A1 | 12/2008 | Knowles et al. |
| 2009/0008605 A1 | 1/2009 | Kawamura et al. |
| 2009/0009065 A1 | 1/2009 | Nishimura et al. |
| 2009/0017330 A1 | 1/2009 | Iwakuma et al. |
| 2009/0030202 A1 | 1/2009 | Iwakuma et al. |
| 2009/0039776 A1 | 2/2009 | Yamada et al. |
| 2009/0045730 A1 | 2/2009 | Nishimura et al. |
| 2009/0045731 A1 | 2/2009 | Nishimura et al. |
| 2009/0101870 A1 | 4/2009 | Pakash et al. |
| 2009/0108737 A1 | 4/2009 | Kwong et al. |
| 2009/0115316 A1 | 5/2009 | Zheng et al. |
| 2009/0165846 A1 | 7/2009 | Johannes et al. |
| 2009/0167162 A1 | 7/2009 | Lin et al. |
| 2009/0179554 A1 | 7/2009 | Kuma et al. |
| 2012/0223276 A1 | 9/2012 | Parham et al. |
| 2012/0223634 A1* | 9/2012 | Xia ...................... C09K 11/06 313/504 |
| 2012/0292607 A1 | 11/2012 | Watanabe et al. |
| 2013/0168656 A1 | 7/2013 | Tsai et al. |
| 2014/0014930 A1 | 1/2014 | Hirose et al. |
| 2014/0110642 A1 | 4/2014 | Stoessel et al. |
| 2014/0364605 A1 | 12/2014 | Li et al. |
| 2015/0194616 A1 | 7/2015 | Li et al. |
| 2015/0207086 A1 | 7/2015 | Li et al. |
| 2016/0072082 A1 | 3/2016 | Brooks et al. |
| 2017/0162802 A1 | 6/2017 | Weaver et al. |

FOREIGN PATENT DOCUMENTS

| | | |
|---|---|---|
| EP | 2034538 | 3/2009 |
| JP | 200511610 | 1/2005 |
| JP | 2007123392 | 5/2007 |
| JP | 2007254297 | 10/2007 |
| JP | 2008074939 | 4/2008 |
| JP | 2012-004529 | 1/2012 |
| WO | 01/39234 | 5/2001 |
| WO | 02/02714 | 1/2002 |
| WO | 02015645 | 2/2002 |
| WO | 03040257 | 5/2003 |
| WO | 03060956 | 7/2003 |
| WO | 2004093207 | 10/2004 |
| WO | 04107822 | 12/2004 |
| WO | 2005014551 | 2/2005 |
| WO | 2005019373 | 3/2005 |
| WO | 2005030900 | 4/2005 |
| WO | 2005089025 | 9/2005 |
| WO | 2005123873 | 12/2005 |
| WO | 2006009024 | 1/2006 |
| WO | 2006056418 | 6/2006 |
| WO | 2006072002 | 7/2006 |
| WO | 2006082742 | 8/2006 |
| WO | 2006098120 | 9/2006 |
| WO | 2006100298 | 9/2006 |
| WO | 2006103874 | 10/2006 |
| WO | 2006114966 | 11/2006 |
| WO | 2006132173 | 12/2006 |
| WO | 2007002683 | 1/2007 |
| WO | 2007004380 | 1/2007 |
| WO | 2007063754 | 6/2007 |
| WO | 2007063796 | 6/2007 |
| WO | 2008056746 | 5/2008 |
| WO | 2008101842 | 8/2008 |
| WO | 2008132085 | 11/2008 |
| WO | 2008/156879 | 12/2008 |
| WO | 2009000673 | 12/2008 |
| WO | 2009003898 | 1/2009 |
| WO | 2009008311 | 1/2009 |
| WO | 2009018009 | 2/2009 |
| WO | 2009021126 | 2/2009 |
| WO | 2009050290 | 4/2009 |
| WO | 2009062578 | 5/2009 |
| WO | 2009063833 | 5/2009 |
| WO | 2009066778 | 5/2009 |
| WO | 2009066779 | 5/2009 |
| WO | 2009086028 | 7/2009 |
| WO | 2009100991 | 8/2009 |
| WO | 2015/171627 | 11/2015 |

OTHER PUBLICATIONS

International Search Report and Written Opinion dated Jul. 24, 2015 for corresponding PCT Application No. PCT/US15/29269.

Adachi, Chihaya et al., "Organic Electroluminescent Device Having a Hole Conductor as an Emitting Layer," Appl. Phys. Lett., 55(15): 1489-1491 (1989).

Adachi, Chihaya et al., "Nearly 100% Internal Phosphorescence Efficiency in an Organic Light Emitting Device," J. Appl. Phys., 90(10): 5048-5051 (2001).

Adachi, Chihaya et al., "High-Efficiency Red Electrophosphorescence Devices," Appl. Phys. Lett., 78(11)1622-1624 (2001).

Aonuma, Masaki et al., "Material Design of Hole Transport Materials Capable of Thick-Film Formation in Organic Light Emitting Diodes," Appl. Phys. Lett, 90, Apr. 30, 2007, 183503-1-183503-3.

Baldo et al., Highly Efficient Phosphorescent Emission from Organic Electroluminescent Devices, Nature, vol. 395, 151-154, (1998).

(56) References Cited

OTHER PUBLICATIONS

Baldo et al., Very high-efficiency green organic light-emitting devices based on electrophosphorescence, Appl. Phys. Lett., vol. 75, No. 1, 4-6 (1999).
Gao, Zhigiang et al., "Bright-Blue Electroluminescence From a Silyl-Substituted ter-(phenylene-vinylene) derivative," Appl. Phys. Lett., 74(6): 865-867 (1999).
Guo, Tzung-Fang et al., "Highly Efficient Electrophosphorescent Polymer Light-Emitting Devices," Organic Electronics, 1: 15-20 (2000).
Hamada, Yuji et al., "High Luminance in Organic Electroluminescent Devices with Bis(10-hydroxybenzo[h]quinolinato) beryllium as an Emitter," Chem. Lett, 905-906 (1993).
Holmes, R.J. et al., "Blue Organic Electrophosphorescence Using Exothermic Host-Guest Energy Transfer," Appl. Phys. Lett., 82(15):2422-2424 (2003).
Hu, Nan-Xing et al., "Novel High Tg Hole-Transport Molecules Based on Indolo[3,2-b]carbazoles for Organic Light-Emitting Devices," Synthetic Metals, 111-112:421-424 (2000).
Huang, Jinsong et al., "Highly Efficient Red-Emission Polymer Phosphorescent Light-Emitting Diodes Based on Two Novel Tris(1-phenylisoquinolinato-C2,N)iridium(III) Derivatives," Adv. Mater., 19:739-743 (2007).
Huang, Wei-Sheng et al., "Highly Phosphorescent Bis-Cyclometalated Iridium Complexes Containing Benzoimidazole-Based Ligands," Chem. Mater., 16(12):2480-2488 (2004).
Hung, L.S. et al., "Anode Modification in Organic Light-Emitting Diodes by Low-Frequency Plasma Polymerization of CHF3," Appl. Phys. Lett., 78(5):673-675 (2001).
Ikai, Masamichi et al., "Highly Efficient Phosphorescence From Organic Light-Emitting Devices with an Exciton-Block Layer," Appl. Phys. Lett., 79(2):156-158 (2001).
Ikeda, Hisao et al., "P-185 Low-Drive-Voltage OLEDs with a Buffer Layer Having Molybdenum Oxide," SID Symposium Digest, 37:923-926 (2006).
Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater. Chem., 3(3):319-320 (1993).
Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).
Kido, Junji et al., 1,2,4-Triazole Derivative as an Electron Transport Layer in Organic Electroluminescent Devices, Jpn. J. Appl. Phys., 32:L917-L920 (1993).
Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino) triphenylamine (m-MTDATA), as Hole-Transport Materials," Adv. Mater., 6(9):677-679 (1994).
Kwong, Raymond C. et al., "High Operational Stability of Electrophosphorescent Devices," Appl. Phys. Lett., 81(1) 162-164 (2002).
Lamansky, Sergey et al., "Synthesis and Characterization of Phosphorescent Cyclometalated Iridium Complexes," Inorg. Chem., 40(7):1704-1711 (2001).
Lee, Chang-Lyoul et al., "Polymer Phosphorescent Light-Emitting Devices Doped with Tris(2-phenylpyridine) Iridium as a Triplet Emitter," Appl. Phys. Lett., 77(15):2280-2282 (2000).
Lo, Shih-Chun et al., "Blue Phosphorescence from Iridium(III) Complexes at Room Temperature," Chem. Mater., 18 (21)5119-5129 (2006).
Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).
Mi, Bao-Xiu et al., "Thermally Stable Hole-Transporting Material for Organic Light-Emitting Diode an Isoindole Derivative," Chem. Mater., 15(16):3148-3151 (2003).

Nishida, Jun-ichi et al., "Preparation, Characterization, and Electroluminescence Characteristics of α-Diimine-type Platinum(II) Complexes with Perfluorinated Phenyl Groups as Ligands," Chem. Lett., 34(4): 592-593 (2005).
Niu, Yu-Hua et al., "Highly Efficient Electrophosphorescent Devices with Saturated Red Emission from a Neutral Osmium Complex," Chem. Mater., 17(13):3532-3536 (2005).
Noda, Tetsuya and Shirota,Yasuhiko, "5,5'-Bis(dimesitylboryl)-2,2'-bithiophene and 5,5"-Bis (dimesitylboryl)-2,2'5',2"-terthiophene as a Novel Family of Electron-Transporting Amorphous Molecular Materials," J. Am. Chem. Soc., 120 (37):9714-9715 (1998).
Okumoto, Kenji et al., "Green Fluorescent Organic Light-Emitting Device with External Quantum Efficiency of Nearly 10%," Appl. Phys. Lett., 89:063504-1-063504-3 (2006).
Palilis, Leonidas C., "High Efficiency Molecular Organic Light-Emitting Diodes Based on Silole Derivatives and Their Exciplexes," Organic Electronics, 4:113-121 (2003).
Paulose, Betty Marie Jennifer S. et al., "First Examples of Alkenyl Pyridines as Organic Ligands for Phosphorescent Iridium Complexes," Adv. Mater., 16(22):2003-2007 (2004).
Ranjan, Sudhir et al., "Realizing Green Phosphorescent Light-Emitting Materials from Rhenium(I) Pyrazolato Diimine Complexes," Inorg. Chem., 42(4):1248-1255 (2003).
Sakamoto, Youichi et al., "Synthesis, Characterization, and Electron-Transport Property of Perfluorinated Phenylene Dendrimers," J. Am. Chem. Soc., 122(8):1832-1833 (2000).
Salbeck, J. et al., "Low Molecular Organic Glasses for Blue Electroluminescence," Synthetic Metals, 91: 209-215 (1997).
Shirota, Yasuhiko et al., "Starburst Molecules Based on pi-Electron Systems as Materials for Organic Electroluminescent Devices," Journal of Luminescence, 72-74:985-991 (1997).
Sotoyama, Wataru et al., "Efficient Organic Light-Emitting Diodes with Phosphorescent Platinum Complexes Containing N^C^N-Coordinating Tridentate Ligand," Appl. Phys. Lett., 86:153505-1-153505-3 (2005).
Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).
T. Östergård et al., "Langmuir-Blodgett Light-Emitting Diodes of Poly(3-Hexylthiophene) Electro-Optical Characteristics Related to Structure," Synthetic Metals, 88:171-177 (1997).
Takizawa, Shin-ya et al., "Phosphorescent Iridium Complexes Based on 2-Phenylimidazo[1,2- α]pyridine Ligands Tuning of Emission Color toward the Blue Region and Application to Polymer Light-Emitting Devices," Inorg. Chem., 46(10):4308-4319 (2007).
Tang, C.W. and VanSlyke, S.A., "Organic Electroluminescent Diodes," Appl. Phys. Lett., 51(12):913-915 (1987).
Tung, Yung-Liang et al., "Organic Light-Emitting Diodes Based on Charge-Neutral Ru II PHosphorescent Emitters," Adv. Mater., 17(8)1059-1064 (2005).
Van Slyke, S. A. et al., "Organic Electroluminescent Devices with Improved Stability," Appl. Phys. Lett., 69 (15):2160-2162 (1996).
Wang, Y. et al., "Highly Efficient Electroluminescent Materials Based on Fluorinated Organometallic Iridium Compounds," Appl. Phys. Lett, 79(4):449-451 (2001).
Wong, Keith Man-Chung et al., A Novel Class of Phosphorescent Gold(III) Alkynyl-Based Organic Light-Emitting Devices with Tunable Colour, Chem. Commun., 2906-2908 (2005).
Wong, Wai-Yeung, "Multifunctional Iridium Complexes Based on Carbazole Modules as Highly Efficient Electrophosphors," Angew. Chem. Int. Ed., 45:7800-7803 (2006).
International Preliminary Report on Patentability issued in connection with International patent application No. PCT/US15/29269, dated Nov. 8, 2016, 10 pages.
Notice of Reasons for Rejection dated Jul. 3, 2018 for corresponding Japanese Patent Application No. 2016-567017.
Li, G.uijie et al. "Modifying Emission Spectral Bandwidth of Phosphorescent Platinum(II) Complexes Through Synthetic Control" Inorg. Chem. 2017, 56, pp. 8244-8256.
Fleetham, Tyler et al., "Efficient "Pure" Blue OLEDs Employing Tetradentate Pt Complexes with a Narrow Spectral Bandwidth" Adv. Mater. 2014, 26, pp. 7116-7121.

(56) References Cited

OTHER PUBLICATIONS

Zhu, Zhi-Qiang et al., "Efficient Cyclometalated Platinum(II) Complex with Superior Operational Stability" Adv. Mater. 2017, 29, 1605002, pp. 1-5.

Fleetham, Tyler B. et al. "Tetradentate Pt(II) Complexes with 6-Membered Chelate Rings: A New Route for Stable and Efficient Blue Organic Light Emitting Diodes" Chem. Mater. 2016, 28, pp. 3276-3282.

Fleetham, Tyler et al. "Efficient and stable single-doped white OLEDs using a palladium-based phosphorescent excimer† " Chem. Sci., 2017, 8, pp. 7983-7990.

\* cited by examiner

ORGANIC ELECTROLUMINESCENT MATERIALS AND DEVICES

CROSS-REFERENCE TO RELATED APPLICATIONS

This application is a continuation-in-part of U.S. application Ser. No. 14/933,684, filed on Nov. 5, 2015, which is a continuation-in-part of PCT application Serial No. PCT/US15/29269, filed on May 5, 2015, which claims priority to U.S. Provisional Application Ser. No. 61/990,239, filed on May 8, 2014, and to U.S. Provisional Application Ser. No. 62/082,970, filed on Nov. 21, 2014, the entire contents of which are incorporated herein by reference. This application also claims priority to U.S. Provisional Application Ser. No. 62/251,447, filed on Nov. 5, 2015, the entire contents of which are incorporated herein by reference.

FIELD OF THE INVENTION

The present invention generally relates to the design of an OLED device where the photoluminescent quantum yield (PLQY) of a phosphorescent emitter contained within the OLED is designed to be deliberately low in order to extend the operation lifetime of the OLED.

JOINT RESEARCH AGREEMENT

The claimed inventions were made by, on behalf of, and/or in connection with one or more of the following parties to a joint university corporation research agreement: University of Southern California, and the Universal Display Corporation. The agreement was in effect on and before the date the claimed inventions were made, and the claimed inventions were made as a result of activities undertaken within the scope of the agreement.

BACKGROUND OF THE INVENTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable. However, this invention will use these generally undesirable non-radiative mechanism to improve device lifetime at the expense of efficiency.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence may be referred to as a "forbidden" transition because the transition requires a change in spin states, and quantum mechanics indicates that such a transition is not favored. As a result, phosphorescence generally occurs in a time frame exceeding at least 10 nanoseconds, and typically greater than 100 nanoseconds. If the natural radiative lifetime of phosphorescence is too long, triplets may decay by a non-radiative mechanism, such that no light is emitted. Organic phosphorescence is also often observed in molecules containing heteroatoms with unshared pairs of electrons at very low temperatures. 2,2'-bipyridine is such a molecule. Non-radiative decay mechanisms are typically temperature dependent, such that an organic material that exhibits phosphorescence at liquid nitrogen temperatures typically does not exhibit phosphorescence at room temperature. But, as demonstrated by Baldo, this problem may be addressed by selecting phosphorescent compounds that do phosphoresce at room temperature. Representative emissive layers include doped or un-doped phosphorescent organometallic materials such as disclosed in U.S. Pat. Nos. 6,303,238; 6,310,360; 6,830,828 and 6,835,469; U.S. Patent Application Publication No. 2002-0182441; and WO 2002/074015.

Phosphorescence may be preceded by a transition from a triplet excited state to an intermediate non-triplet state from which the emissive decay occurs. For example, organic molecules coordinated to lanthanide elements often phosphoresce from excited states localized on the lanthanide metal. However, such materials do not phosphoresce directly from a triplet excited state but instead emit from an atomic excited state centered on the lanthanide metal ion. The europium diketonate complexes illustrate one group of these types of species.

Phosphorescence from triplets can be enhanced over fluorescence by confining, preferably through bonding, the organic molecule in close proximity to an atom of high atomic number. This phenomenon, called the heavy atom effect, is created by a mechanism known as spin-orbit coupling. Such a phosphorescent transition may be observed from an excited metal-to-ligand charge transfer (MLCT) state of an organometallic molecule such as tris(2-phenylpyridine)iridium(III).

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Alternatively, the OLED can be designed to emit white light. In conventional liquid crystal displays, emission from a white backlight is filtered using absorption filters to produce red, green and blue emission. The same technique can also be used with OLEDs. The white OLED can be either a single EML device or a stacked structure. Color may be measured using CIE coordinates, which are well known to the art.

One example of a green emissive molecule is tris(2-phenylpyridine) iridium, denoted Ir(ppy)$_3$, which has the following structure:

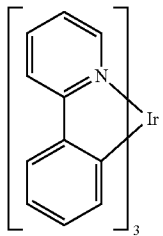

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY OF THE INVENTION

According to an aspect of the present disclosure, An organic light emitting device (OLED) is provided. The OLED comprises an anode, a cathode, and an emission layer, disposed between the anode and the cathode, comprising a first emitting compound; wherein the first emitting compound is capable of functioning as a blue phosphorescent emitter in the OLED at room temperature; wherein the first emitting compound has PLQY of less than 90% at room temperature; wherein the OLED has an external quantum efficiency of between 8% and 20% at 1 mA/cm$^2$. In one aspect, the OLED has a performance lifetime of at least 30 hours under a constant current of 20 mA/cm$^2$ to 80% of the initial luminance at room temperature. In another aspect, the first emitting compound has less than 2 microsecond of the fastest component of its photoluminescence transient that fits to a multiple exponential function at room temperature under inert atmosphere. In a further aspect, the first emitting compound has a structure $(L_A)_n ML_m$ according to the following Formula 1:

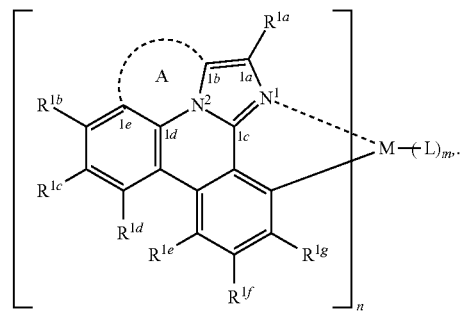

Formula 1

In Formula 1, M is a metal having an atomic weight greater than 40, n has a value of at least 1 and m+n is the maxiumn number of ligands that may be attached to the metal M;

wherein A is a linking group having two to three linking atoms, wherein the linking atoms are each independently selected from the group consisting of C, Si, O, S, N, B or combinations thereof;

wherein $R^{1a}$-$R^{1g}$ are each independently selected from the group consisting of hydrogen, deuterium, alkyl, cycloalkyl, heteroalkyl, alkoxy, aryloxy, amino, silyl, alkenyl, cycloalkenyl, heteroalkenyl, alkynyl, aralkyl, CN, $CF_3$, $CO_2R$, C(O)R, $C(O)NR_2$, $NR_2$, $NO_2$, OR, SR, $SO_2$, SOR, $SO_3R$, halo, aryl, heteroaryl, a heterocyclic group, and combinations thereof;

wherein each R is independently selected from the group consisting of hydrogen, deuterium, halo, alkyl, cycloalkyl, heteroalkyl, alkoxy, aryloxy, amino, silyl, alkenyl, cycloalkenyl, heteroalkenyl, alkynyl, aralkyl, aryl, heteroaryl, and combinations thereof;

wherein any one of the ring atoms to which $R^{1b}$ to $R^{1g}$ are attached may be replaced with a nitrogen atom, wherein when the ring atom is replaced with a nitrogen atom the corresponding R group is not present; and wherein L is a substituted or unsubstituted cyclometallated ligand.

BRIEF DESCRIPTION OF THE DRAWINGS

The foregoing summary, as well as the following detailed description of exemplary embodiments of the compounds, compositions and devices in accordance with the present invention, will be better understood when read in conjunction with the appended drawings of exemplary embodiments. It should be understood, however, that the invention is not limited to the precise arrangements and instrumentalities shown.

In the drawings.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices,"

Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Imidazophenanthridines are useful ligands that can provide 460 nm emission when ligated to both platinum and iridium metals. Phosphorescent imidazophenanthridine complexes can provide deep blue emission with tunable photoluminescent quantum yield, ranging from nearly zero to unity. Unfortunately, the device lifetime is limited for both iridium and platinum based blue-emitting complexes. We provide a strategy herein to improve the stability of the imidazophenanthridine ligand by addressing a bond on the ligand that is shown by computational theory, mass spec fragmentation analysis, and photooxidative studies to be a weak bond due to polycyclic ring strain and electronic structure.

Figure 1:
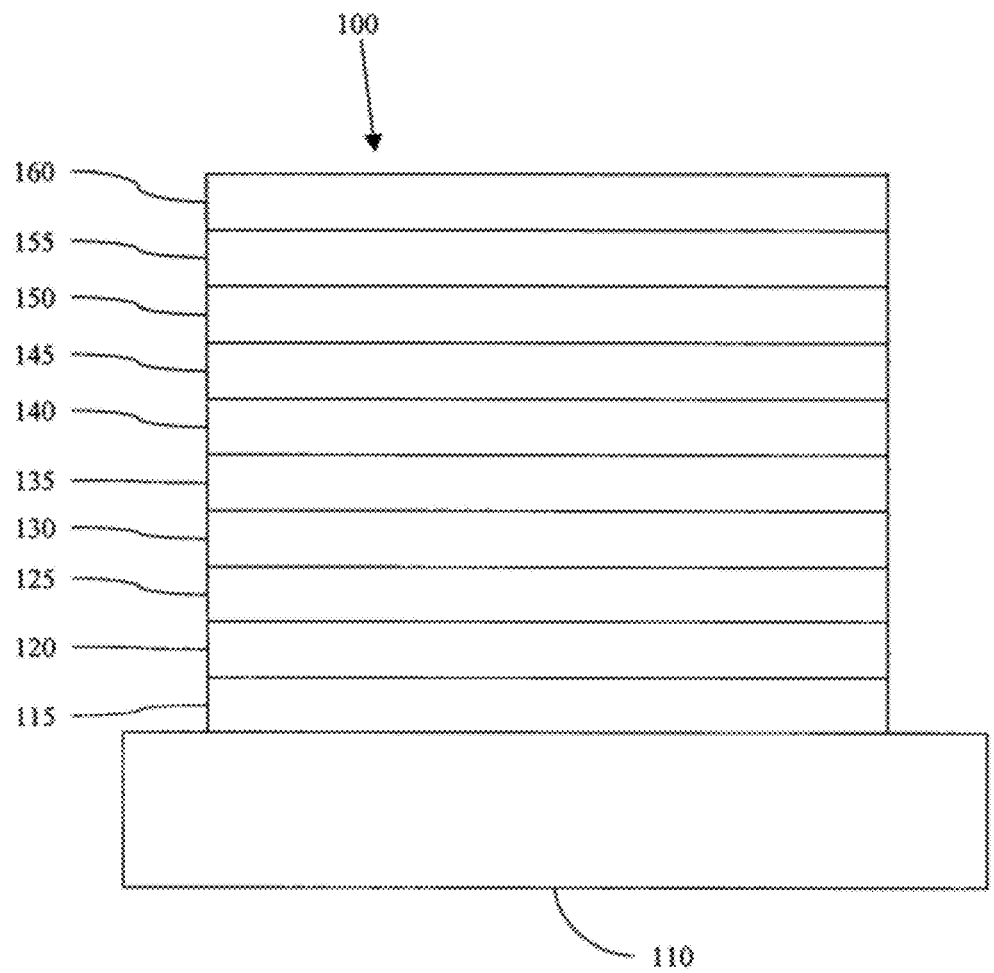
FIG. 1 shows an exemplary organic light emitting device 100.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, a cathode 160, and a barrier layer 170. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with F4-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
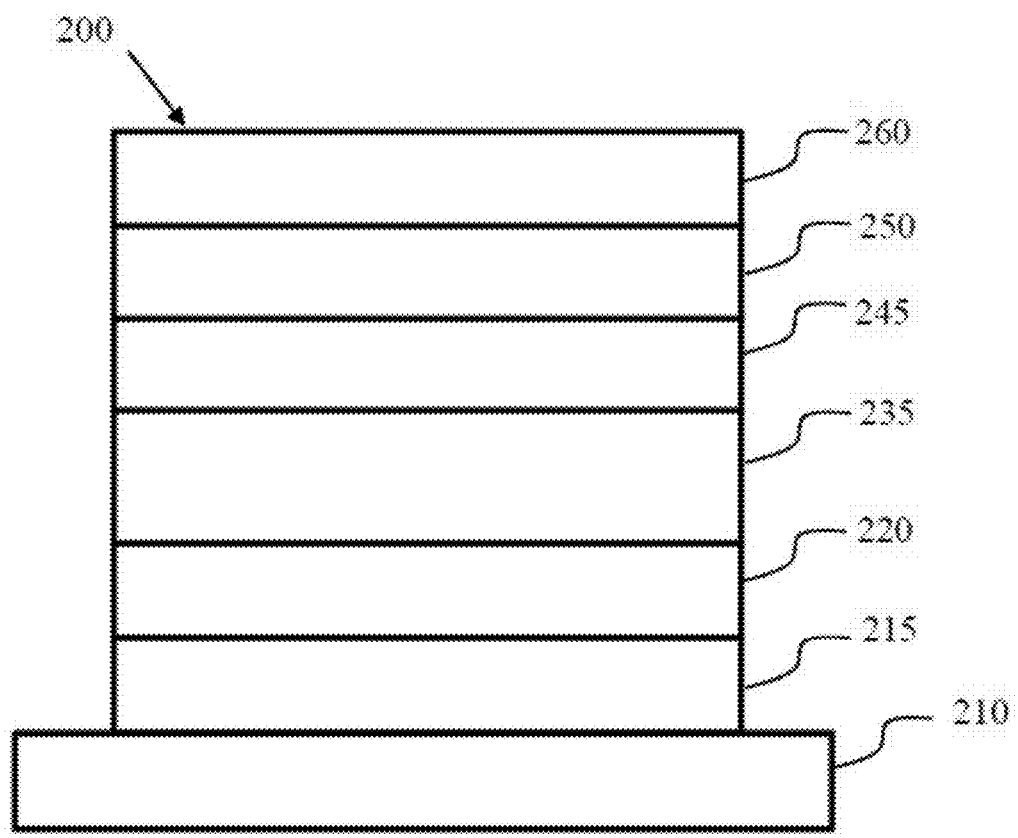
FIG. 2 illustrates an exemplary organic light emitting device 200 according to the present disclosure.
Figure 3:
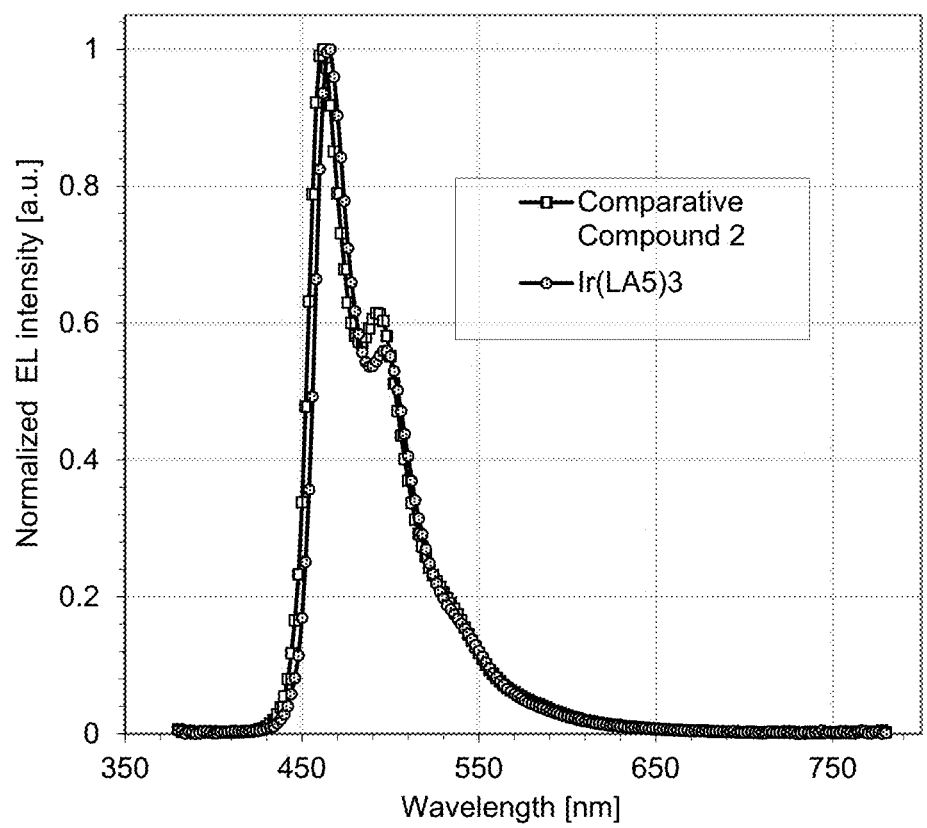
FIG. 3 shows the EL spectra from a $Ir(LA5)_3$ emitting OLED and a Comparative Compound 2 emitting OLED.
Figure 4:
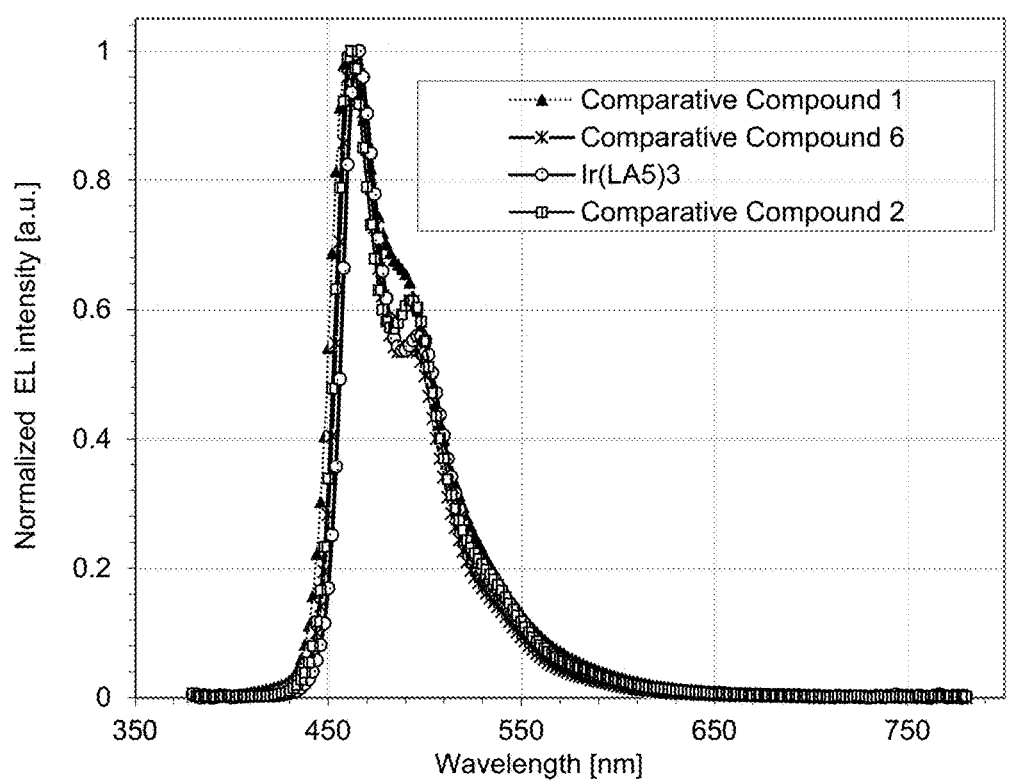
FIG. 4 shows the EL spectra from a $Ir(LA5)_3$ emitting OLED, a Comparative Compound 6 emitting OLED, a Comparative Compound 1 emitting OLED and a Comparative Compound 2 emitting OLED.
Figure 5:
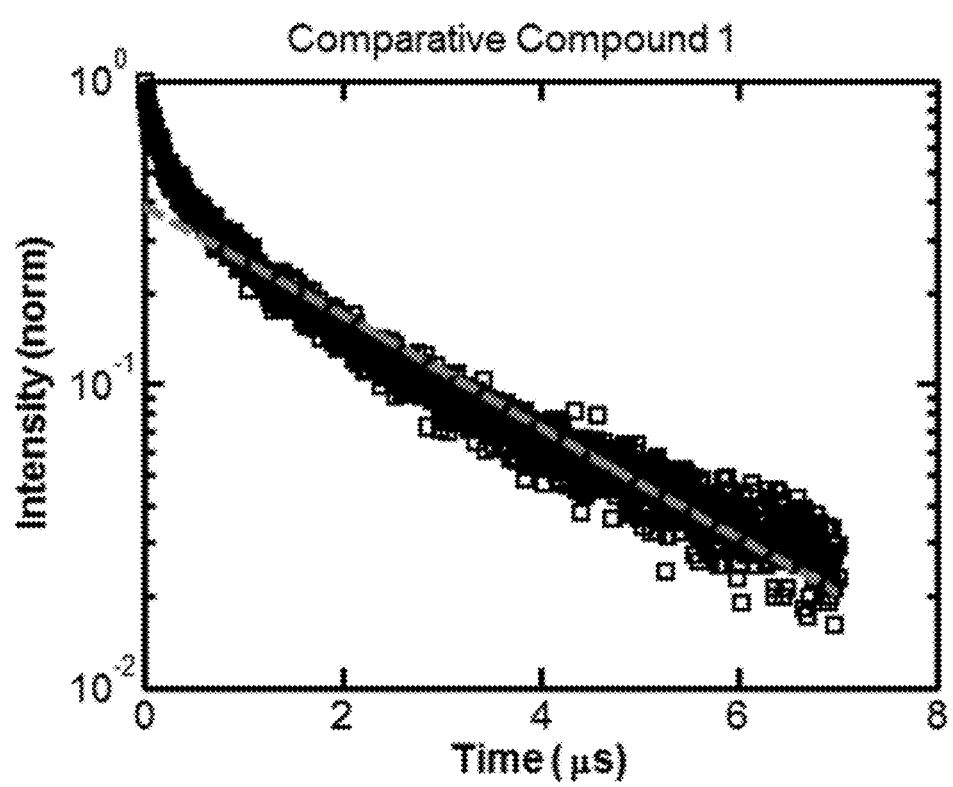
FIG. 5 shows the PL transient data of Comparative Compound 1 in PMMA measured in an inert atmosphere.
Figure 6:
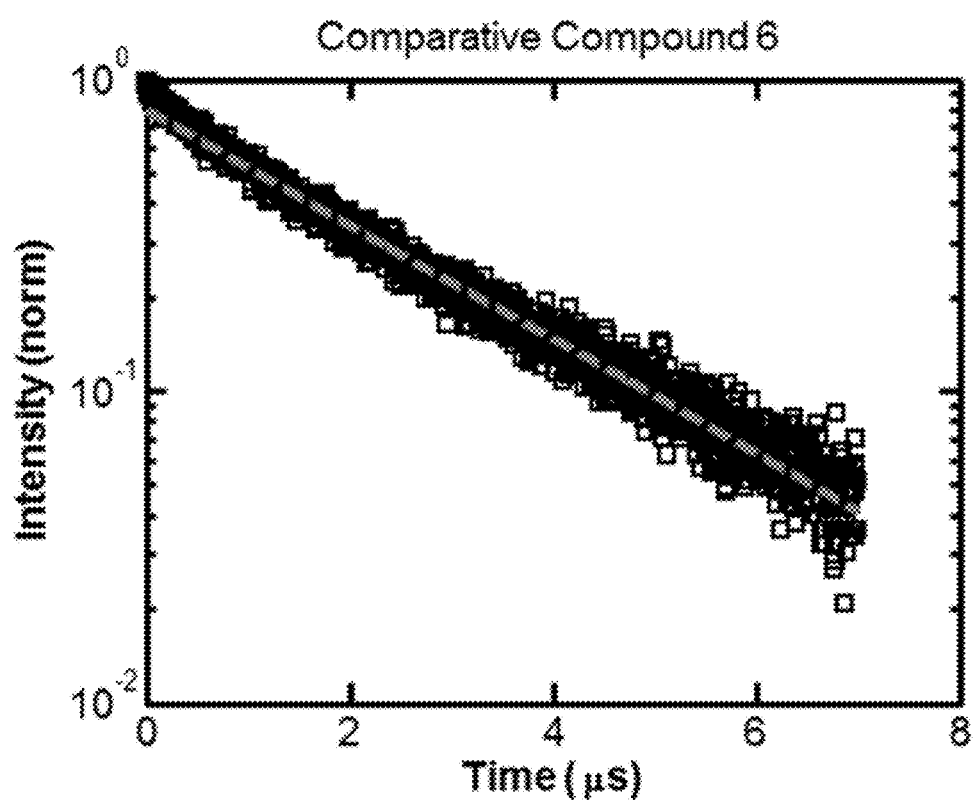
FIG. 6 shows the PL transient data of Comparative Compound 6 in PMMA measured in an inert atmosphere.
Figure 7:
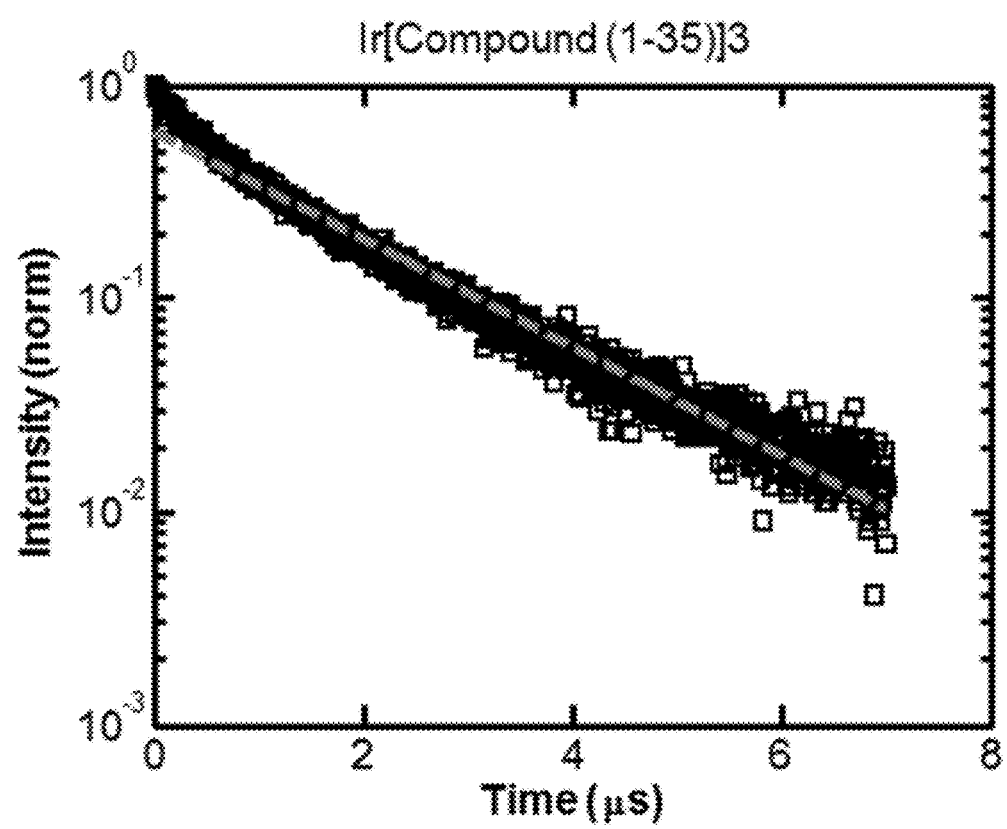
FIG. 7 shows the PL transient data of Ir[Compound (1-35)]3 in PMMA measured in an inert atmosphere.
Figure 8:
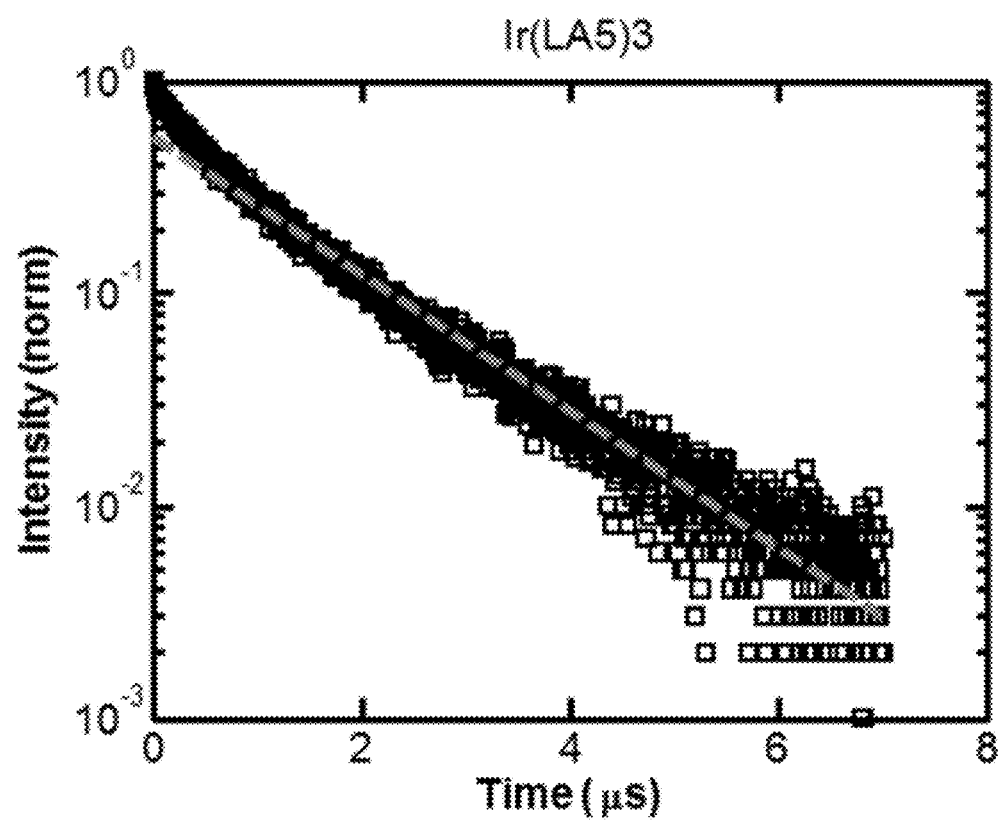
FIG. 8 shows the PL transient data of Ir(LA5)3 in PMMA measured in an inert atmosphere.
Figure 9:
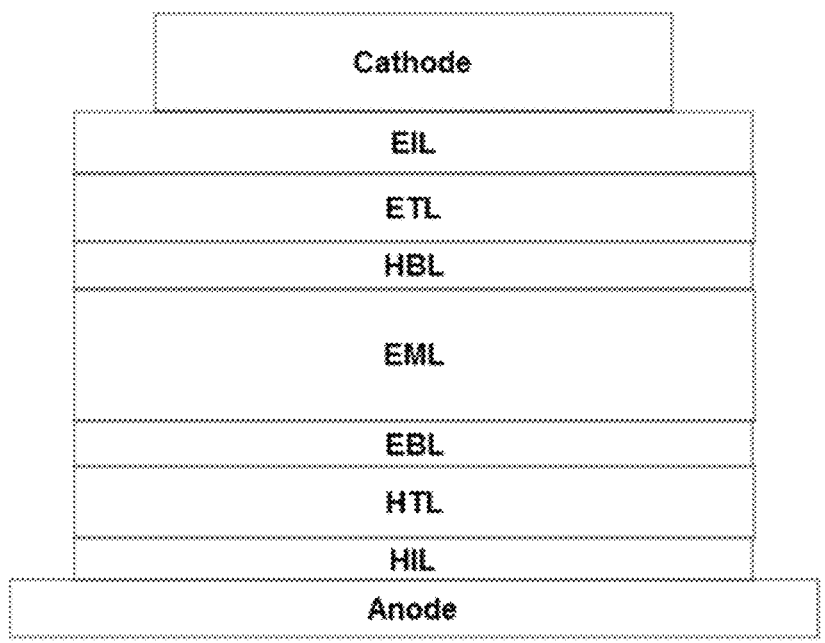
FIG. 9 shows a typical bottom emitting device architecture.
Figure 10:
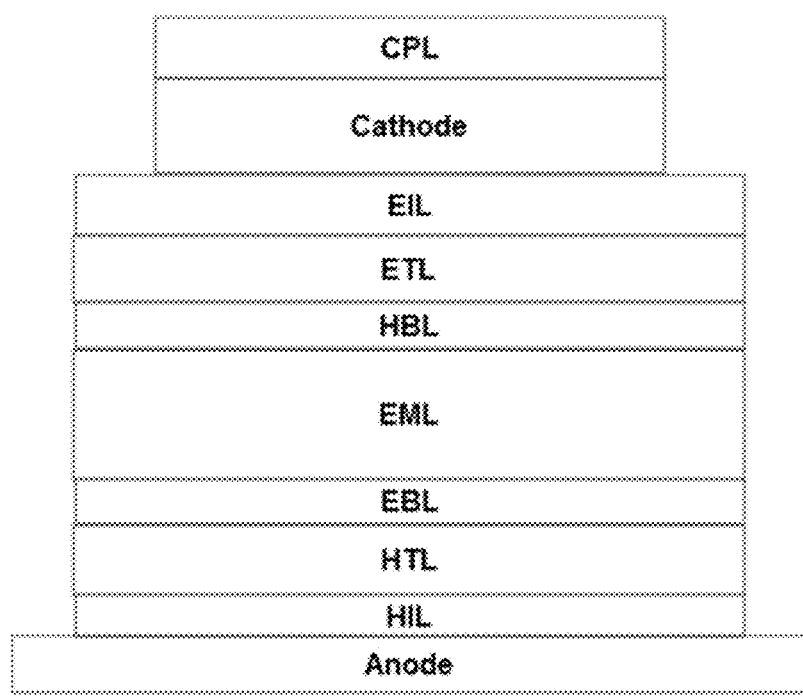
FIG. 10 shows a typical top emitting device architecture.
Figure 11:
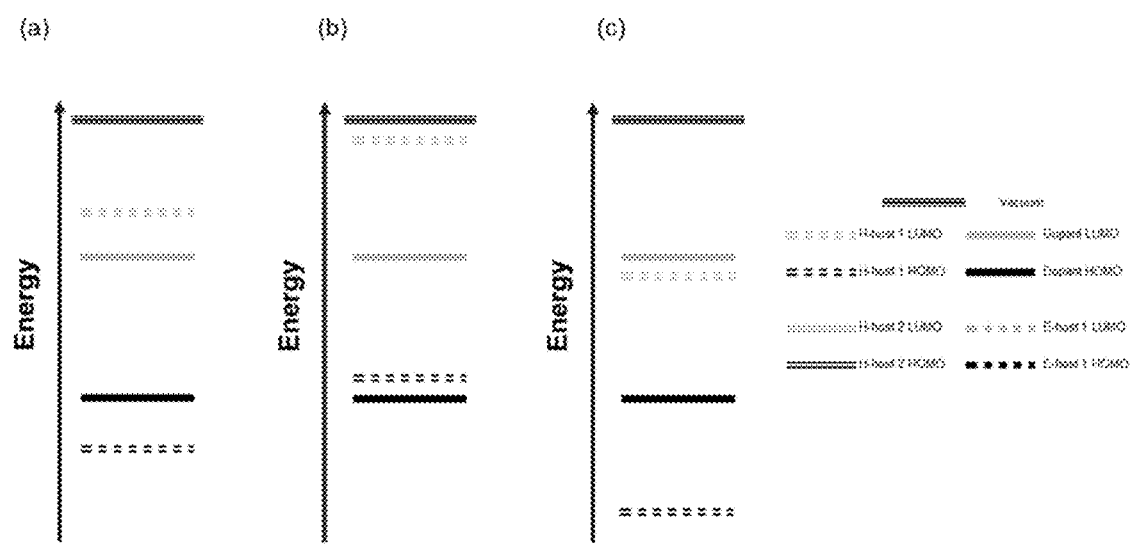
FIG. 11 shows a preferred embodiment of the emitting layer energy match between emitter and host(s). In configuration (a) the dopant's HOMO and LUMO are lower in energy than the hole host (h-host). This results in the dopant being both an electron and hole trap. In configuration (b) the HOMO level of the h-host is greater than the HOMO of the dopant. This results in the dopant being an electron trap and hole transport occurring on the host. In configuration (c) the LUMO of dopant is greater than that of the h-host resulting in the dopant being a hole trap and the h-host is the thermodynamically preferred material for electron transport.
Figure 12:
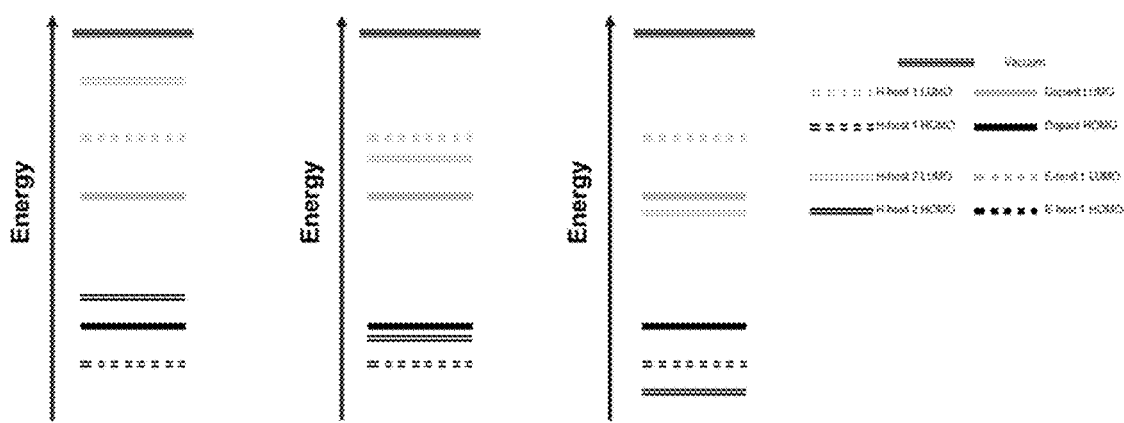
FIG. 12 shows another preferred embodiment of the emitting layer energy match between emitter and host(s). In all configurations two h-hosts are used in the emissive layer. This allows for better tuning of the relative energy levels of the dopant to the host. In configuration (a) the HOMO level of one h-host is higher than the dopant while HOMO level of the other is lower. The LUMO of both h-hosts is greater than the dopant. This configuration allows for good hole transport and a low operating voltage device. In configuration (b) the HOMO of the dopant is greater than the HOMO of either h-host while the LUMO is smaller than either h-host. In this configuration the dopant is a hole and electron trap. The small energy difference between the HOMO of either host and the HOMO of the dopant enables a low operating voltage device. In configuration (c) the HOMO level of the dopant is greater than HOMO level of either h-host while the LUMO is greater than only 1 h-host. In this configuration the dopant is only a hole trap and the h-host with the larger LUMO is the thermodynamically preferred material for electron transport.
Figure 13:
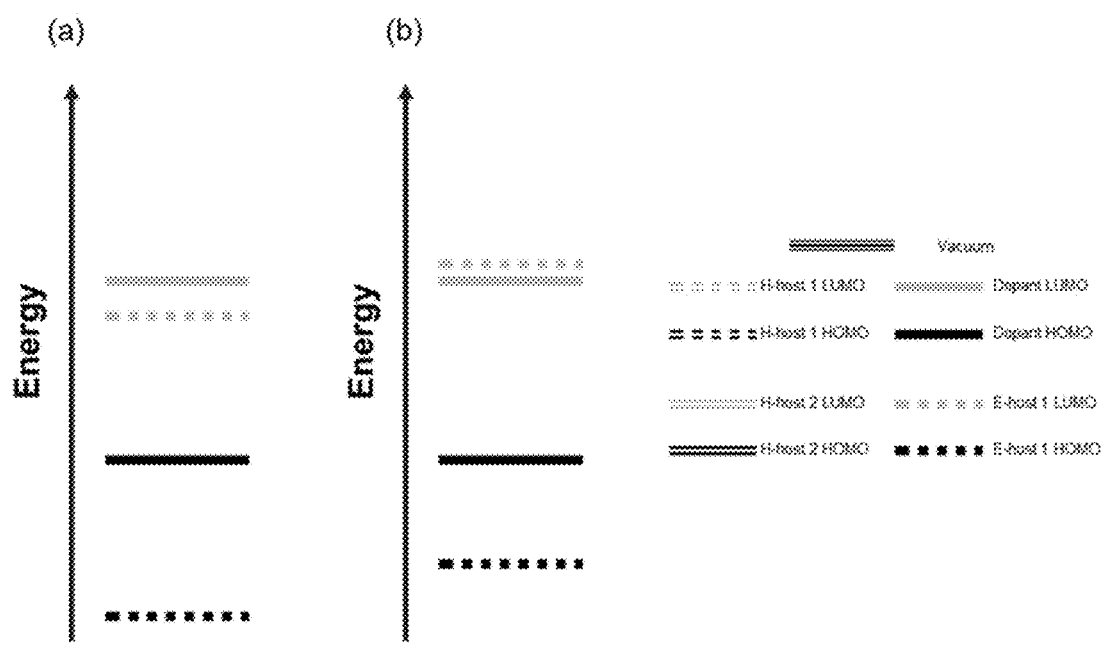
FIG. 13 shows another preferred embodiment of the emitting layer energy match between emitter and host(s). In configuration (a) the dopant's HOMO and LUMO levels are both greater than that of the electron host (e-host). The dopant is a hole trap while the e-host is the thermodynamically preferred material for electron transport. In configuration (b) the dopant's HOMO is greater than the e-host while the LUMO is smaller than the LUMO of the host. The dopant is a hole and electron trap.
Figure 14:
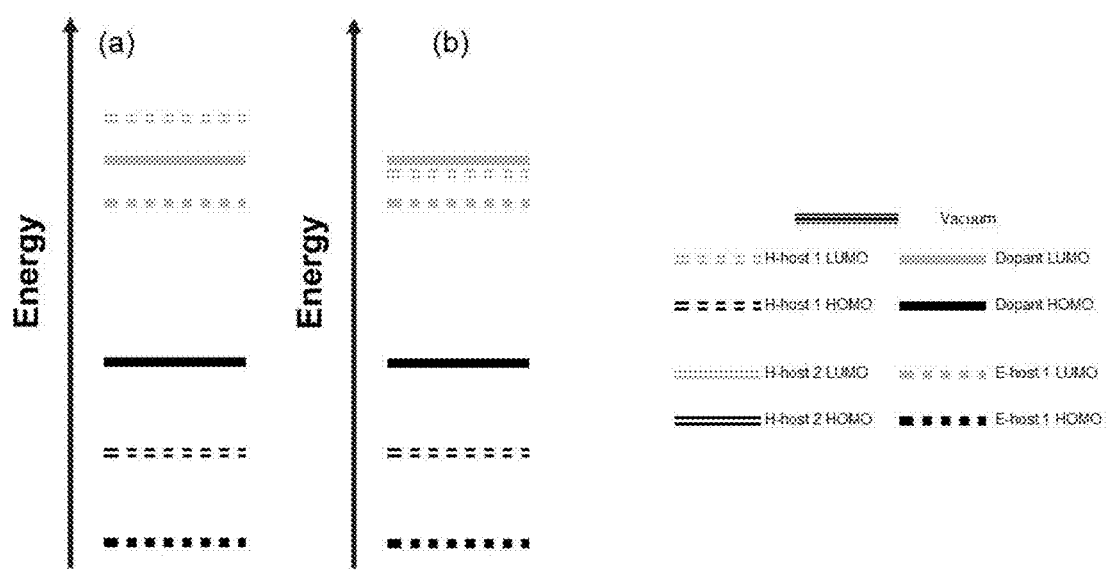
FIG. 14 shows another preferred embodiment of the emitting layer energy match between emitter and host(s). In configuration both configurations the dopant's HOMO and LUMO levels are both greater than that of the h-host. The dopant is a hole trap. The LUMO of the e-host is smaller than that of both the h-host and the dopant making the e-host the thermodynamically preferred material for electron transport. In configuration (a) the dopant's LUMO is smaller than the h-host's LUMO while in configuration (b) the dopants LUMO is greater than the h-host's LUMO.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve outcoupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processibility than those having symmetric structures, because asymmetric materials may have a lower tendency to recrystallize. Dendrimer substituents may be used to enhance the ability of small molecules to undergo solution processing.

Devices fabricated in accordance with embodiments of the present invention may further optionally comprise a barrier layer. One purpose of the barrier layer is to protect the electrodes and organic layers from damaging exposure to harmful species in the environment including moisture, vapor and/or gases, etc. The barrier layer may be deposited over, under or next to a substrate, an electrode, or over any other parts of a device including an edge. The barrier layer may comprise a single layer, or multiple layers. The barrier layer may be formed by various known chemical vapor deposition techniques and may include compositions having a single phase as well as compositions having multiple phases. Any suitable material or combination of materials may be used for the barrier layer. The barrier layer may incorporate an inorganic or an organic compound or both. The preferred barrier layer comprises a mixture of a polymeric material and a non-polymeric material as described in U.S. Pat. No. 7,968,146, PCT Pat. Application Nos. PCT/US2007/023098 and PCT/US2009/042829, which are herein incorporated by reference in their entireties. To be considered a "mixture", the aforesaid polymeric and non-polymeric materials comprising the barrier layer should be deposited under the same reaction conditions and/or at the same time. The weight ratio of polymeric to non-polymeric material may be in the range of 95:5 to 5:95. The polymeric material and the non-polymeric material may be created from the same precursor material. In one example, the mixture of a polymeric material and a non-polymeric material consists essentially of polymeric silicon and inorganic silicon.

Devices fabricated in accordance with embodiments of the invention can be incorporated into a wide variety of electronic component modules (or units) that can be incorporated into a variety of electronic products or intermediate components. Examples of such electronic products or intermediate components include display screens, lighting devices such as discrete light source devices or lighting panels, etc. that can be utilized by the end-user product manufacturers. Such electronic component modules can optionally include the driving electronics and/or power source(s). Devices fabricated in accordance with embodiments of the invention can be incorporated into a wide variety of consumer products that have one or more of the electronic component modules (or units) incorporated therein. Such consumer products would include any kind of products that include one or more light source(s) and/or one or more of some type of visual displays. Some examples of such consumer products include flat panel displays, computer monitors, medical monitors, televisions, billboards, lights for interior or exterior illumination and/or signaling, heads-up displays, fully or partially transparent displays, flexible displays, laser printers, telephones, cell phones, tablets, phablets, personal digital assistants (PDAs), wearable devices, laptop computers, digital cameras, camcorders, viewfinders, micro-displays, 3-D displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.), but could be used outside this temperature range, for example, from −40 degree C. to +80 degree C.

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The term "halo," "halogen," or "halide" as used herein includes fluorine, chlorine, bromine, and iodine.

The term "alkyl" as used herein means a straight or branched chain saturated acyclic hydrocarbon radical, which may optionally be substituted with any suitable substituent. Accordingly, an alkyl radical in accordance with the present invention can comprise any combination of primary, secondary, tertiary and quaternary carbon atoms. Exemplary alkyl radicals include, but are not limited to, $C_1$-$C_{20}$-alkyl, $C_1$-$C_{18}$-alkyl, $C_1$-$C_{16}$-alkyl, $C_1$-$C_{14}$-alkyl, $C_1$-$C_{12}$-alkyl, $C_1$-$C_{10}$-alkyl, $C_1$-$C_8$-alkyl, $C_1$-$C_6$-alkyl, $C_1$-$C_4$-alkyl, $C_1$-$C_3$-alkyl, and $C_2$-alkyl. Specific examples include methyl, ethyl, 1-propyl, 2-propyl, 2-methyl-1-propyl, 1-butyl, 2-butyl, t-butyl, n-octyl, n-decyl, and n-hexadecyl.

As used herein, the term "heteroalkyl" refers to an alkyl group as described herein in which one or more carbon atoms is replaced by a heteroatom. Suitable heteroatoms include oxygen, sulfur, nitrogen, phosphorus, and the like. Examples of heteroalkyl groups include, but are not limited to, alkoxy, amino, thioester, poly(ethylene glycol), and alkyl-substituted amino.

The term "cycloalkyl" as used herein contemplates cyclic alkyl radicals. Preferred cycloalkyl groups are those containing 3 to 7 carbon atoms and includes cyclopropyl, cyclopentyl, cyclohexyl, and the like. Additionally, the cycloalkyl group may be optionally substituted.

As used herein, the term "alkenyl" means acyclic branched or unbranched hydrocarbon radical having one or more carbon-carbon double bonds. Exemplary alkenyl radicals include, but are not limited to, $C_1$-$C_{20}$-alkenyl radical, $C_2$-$C_{18}$-alkenyl radical, $C_2$-$C_{16}$-alkenyl radical, $C_2$-$C_{14}$-alkenyl radical, $C_2$-$C_{12}$-alkenyl radical, $C_2$-$C_{10}$-alkenyl radical, $C_2$-$C_8$-alkenyl radical, $C_2$-$C_6$-alkenyl radical, $C_2$-$C_4$-alkenyl radical, $C_2$-$C_3$-alkenyl radical, and $C_2$-alkenyl radical. Specific examples include, but are not limited to, ethylenyl, propylenyl, 1-butenyl, 2-butenyl, isobutylenyl, 1-pentenyl, 2-pentenyl, 3-methyl-1-butenyl, 2-methyl-2-butenyl, and 2,3-dimethyl-2-butenyl.

As used herein, the term "alkylene" means an optionally substituted saturated straight or branched chain hydrocarbon radical. Exemplary alkylene radicals include, but are not limited to, $C_1$-$C_{20}$-alkylene, $C_2$-$C_{18}$-alkylene, $C_2$-$C_{16}$-alkylene, $C_2$-$C_{14}$-alkylene, $C_2$-$C_{12}$-alkylene, $C_2$-$C_{10}$-alkylene, $C_2$-$C_8$-alkylene, $C_2$-$C_6$-alkylene, $C_2$-$C_4$-alkylene, $C_2$-$C_3$-alkylene, and $C_2$-alkylene. Specific examples of alkylene include, but are not limited to, methylene, dimethylene, and trimethylene.

As used herein, the term "alkynyl" means an acyclic branched or unbranched hydrocarbon having at least one carbon-carbon triple bond. Exemplary alkylene radicals include, but are not limited to, $C_1$-$C_{20}$-alkynyl radical, $C_2$-$C_{18}$-alkynyl radical, $C_2$-$C_{16}$-alkynyl radical, $C_2$-$C_{14}$-alkynyl radical, $C_2$-$C_{12}$-alkynyl radical, $C_2$-$C_{10}$-alkynyl radical, $C_2$-$C_8$-alkynyl radical, $C_2$-$C_6$-alkynyl radical, $C_2$-$C_4$-alkynyl radical, $C_2$-$C_3$-alkynyl radical, and $C_2$-alkynyl radical. Specific examples of alkynyl include, but are not limited to, propargyl, and 3-pentynyl, acetylenyl, propynyl, 1-butynyl, 2-butynyl, 1-pentynyl, 2-pentynyl, and 3-methyl-1-butynyl.

As used herein, the term "aralkyl" means one or more aryl radicals as defined herein attached through an alkyl bridge (e.g., -alkyl-(aryl), wherein j is 1, 2 or 3). Specific examples of aralkyl include, but are not limited to, benzyl (—CH$_2$-phenyl, i.e., Bn), diphenyl methyl (—CH$_2$-(phenyl)$_2$) and trityl (—C-(phenyl)$_3$). Additionally, the aralkyl group may be optionally substituted.

Unless stated otherwise, as used herein, the term "heterocycle" and variants of the term, including "heterocyclic group" and "heterocyclyl," means an optionally substituted monocyclic or polycyclic ring system having as ring members atoms of at least two different elements and wherein the monocyclic or polycyclic ring system is either saturated, unsaturated or aromatic. In some embodiments, heterocycle comprises carbon atoms and at least one heteroatom. In some embodiments, heterocyle comprises carbon atoms and at least one heteroatom selected from nitrogen, oxygen, silicon, selenium, and sulfur, and wherein the nitrogen, oxygen, silicon, selenium, and sulfur heteroatoms may be optionally oxidized, and the nitrogen heteroatom may be optionally quaternized. Examples of heterocycle include, but are not limited to, furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl. Thus, in addition to the aromatic heteroaryls listed above, heterocycles also include (but are not limited to) morpholinyl, pyrrolidinonyl, pyrrolidinyl, piperizinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, and tetrahydrothiopyranyl.

As used herein, the term "aryl" means an optionally substitued monoyclic or polycyclic aromatic hydrocarbon. Specific examples of aryl include, but are not limited to, phenyl, phenyl, 4-methylphenyl, 2,6-dimethylphenyl, naphthyl, anthracenyl, and phenanthrenyl. The term "aryl" or "aromatic group" as used herein contemplates single-ring groups and polycyclic ring systems. The polycyclic rings may have two or more rings in which two carbons are common to two adjoining rings (the rings are "fused") wherein at least one of the rings is aromatic, e.g., the other rings can be cycloalkyls, cycloalkenyls, aryl, heterocycles, and/or heteroaryls. Additionally, the aryl group may be optionally substituted.

As used herein, the term "heteroaryl" means an optionally substituted monoyclic or polycyclic aromatic hydrocarbon having at least one heteroatom and at least one carbon atom. In some embodiments, the at least one heteroatom is selected from nitrogen, oxygen, silicon, selenium, and sulfur. Specific examples of heteroaryl include, but are not limited to, furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl.

The alkyl, cycloalkyl, alkenyl, alkynyl, aralkyl, heterocyclic group, aryl, and heteroaryl may be optionally substituted with one or more substituents selected from the group consisting of hydrogen, deuterium, halogen, alkyl, cycloalkyl, heteroalkyl, arylalkyl, alkoxy, aryloxy, amino, cyclic amino, silyl, alkenyl, cycloalkenyl, heteroalkenyl, alkynyl, aryl, heteroaryl, acyl, carbonyl, carboxylic acid, ether, ester, nitrile, isonitrile, sulfanyl, sulfinyl, sulfonyl, phosphino, and combinations thereof.

As used herein, "substituted" indicates that a substituent other than H is bonded to the relevant position, such as carbon. Thus, for example, where $R^1$ is mono-substituted, then one $R^1$ must be other than H. Similarly, where $R^1$ is di-substituted, then two of $R^1$ must be other than H. Similarly, where $R^1$ is unsubstituted, $R^1$ is hydrogen for all available positions.

The "aza" designation in the fragments described herein, i.e. aza-dibenzofuran, aza-dibenzothiophene, etc. means that one or more of the C—H groups in the respective fragment can be replaced by a nitrogen atom, for example, and without any limitation, azatriphenylene encompasses both dibenzo[f,h]quinoxaline and dibenzo[f,h]quinoline. One of ordinary skill in the art can readily envision other nitrogen analogs of the aza-derivatives described above, and all such analogs are intended to be encompassed by the terms as set forth herein.

It is to be understood that when a molecular fragment is described as being a substituent or otherwise attached to another moiety, its name may be written as if it were a fragment (e.g. phenyl, phenylene, naphthyl, dibenzofuryl) or as if it were the whole molecule (e.g. benzene, naphthalene, dibenzofuran). As used herein, these different ways of designating a substituent or attached fragment are considered to be equivalent.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, the term "triplet energy" refers to an energy corresponding to the highest energy feature discernable in the phosphorescence spectrum of a given material. The highest energy feature is not necessarily the peak having the greatest intensity in the phosphorescence spectrum, and could, for example, be a local maximum of a clear shoulder on the high energy side of such a peak.

According to an aspect of the present disclosure, An organic light emitting device (OLED) is provided. The OLED comprises an anode, a cathode, and an emission layer, disposed between the anode and the cathode, comprising a first emitting compound; wherein the first emitting compound is capable of functioning as a blue phosphorescent emitter in the OLED at room temperature; wherein the first emitting compound has PLQY of less than 90% at room temperature; wherein the OLED has an external quantum efficiency of between 8% and 20% at 1 mA/cm$^2$.

In one embodiment, the first emitting compound is capable of emitting light from a triplet excited state to a ground singlet state at room temperature. In another embodiment, the first emitting compound is a metal coordination complex having a metal-carbon bond. In another embodiment, the metal is selected from the group consisting of Ir, Rh, Re, Ru, Os, Pt, Au, and Cu. In another embodiment, the metal is Ir. In yet another embodiment, the metal is Pt.

In one aspect, the first emitting compound has the formula of $M(L^1)_x(L^2)_y(L^3)_z$;

wherein $L^1$, $L^2$ and $L^3$ can be the same or different;

wherein x is 1, 2, or 3;

wherein y is 0, 1, or 2;

wherein z is 0, 1, or 2;

wherein x+y+z is the oxidation state of the metal M;

wherein $L^1$, $L^2$ and $L^3$ are each independently selected from the group consisting of;

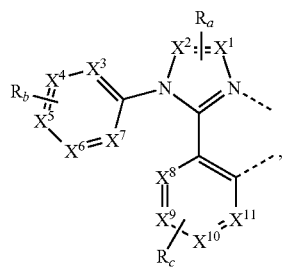

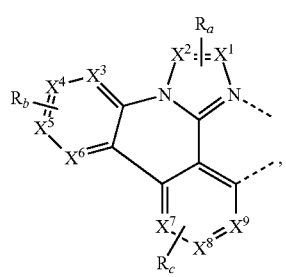

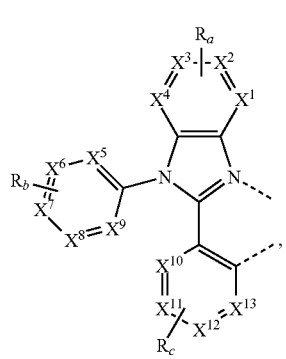

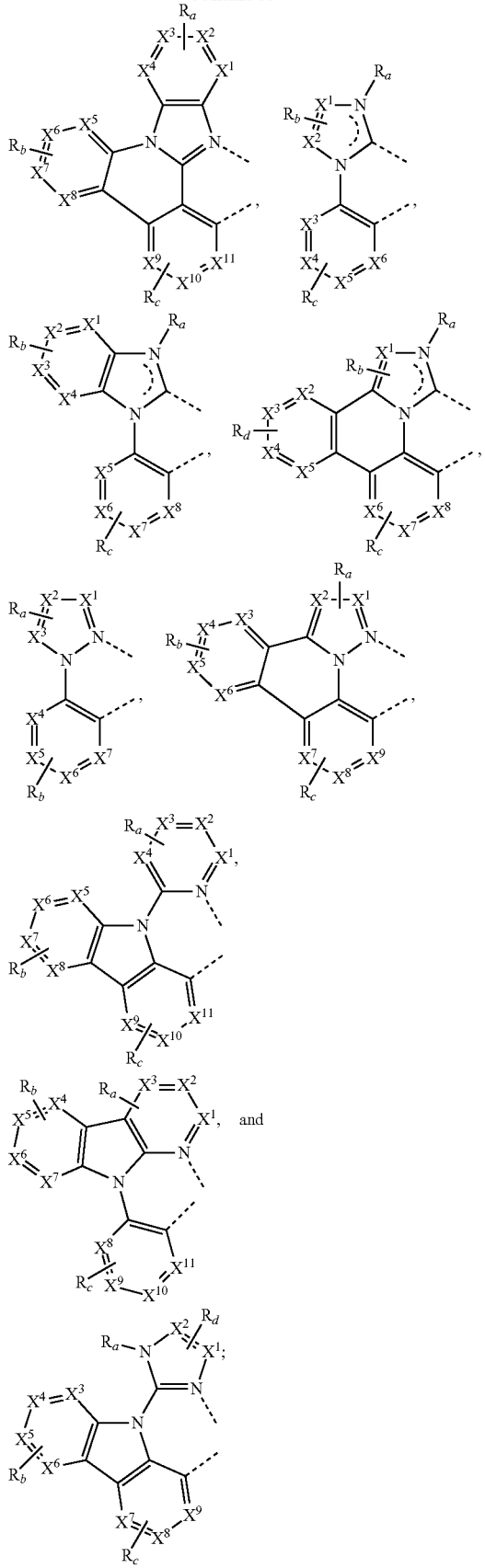

wherein each $X^1$ to $X^{13}$ are independently selected from the group consisting of carbon and nitrogen;

wherein X is selected from the group consisting of BR', NR', PR', O, S, Se, C=O, S=O, $SO_2$, CR'R", SiR'R", and GeR'R";

wherein R' and R" are optionally fused or joined to form a ring;

wherein each $R_a$, $R_b$, $R_c$, and $R_d$ may represent from mono substitution to the possible maximum number of substitution, or no substitution;

wherein R', R", $R_a$, $R_b$, $R_c$, and $R_d$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein any two adjacent substitutents of $R_a$, $R_b$, $R_c$, and $R_d$ are optionally fused or joined to form a ring or form a multidentate ligand.

In one aspect, the OLED has a performance lifetime of at least 30 hours under a constant current of 20 mA/cm² to 80% of the initial luminance at room temperature. In one embodiment, the OLED has a performance lifetime of at least 100 hours under a constant current of 20 mA/cm² to 80% of the initial luminance at room temperature. In one embodiment, the OLED has a performance lifetime of at least 150 hours under a constant current of 20 mA/cm² to 80% of the initial luminance at room temperature. In one embodiment, the OLED has a performance lifetime of at least 200 hours under a constant current of 20 mA/cm² to 80% of the initial luminance at room temperature. In one embodiment, the OLED has a performance lifetime of at least 300 hours under a constant current of 20 mA/cm² to 80% of the initial luminance at room temperature. In one embodiment, the OLED has a performance lifetime of at least 500 hours under a constant current of 20 mA/cm² to 80% of the initial luminance at room temperature. In one embodiment, the OLED has a performance lifetime of at least 1,000 hours under a constant current of 20 mA/cm2 to 80% of the initial luminance at room temperature. In one embodiment, the OLED has a performance lifetime of at least 2,000 hours under a constant current of 20 mA/cm2 to 80% of the initial luminance at room temperature.

In one aspect, the first emitting compound has a first triplet energy less than 500 nanometers. It is to be noted that smaller nanometer implies a higher triplet energy. In one embodiment, the first emitting compound has a first triplet energy less than 480 nanometers. In one embodiment, the first emitting compound has a first triplet energy less than 470 nanometers. In one embodiment, the first emitting compound has a first triplet energy less than 460 nanometers. In one embodiment, the first emitting compound has a first triplet energy less than 450 nanometers.

In one aspect, the first emitting compound emits light having a CIE x-coordinate less than 0.25 and a CIE y-coordinate less than 0.4. In one embodiment, the first emitting compound emits light having a CIE x-coordinate less than 0.25 and a CIE y-coordinate less than 0.3. In one embodiment, the first emitting compound emits light having a CIE x-coordinate less than 0.25 and a CIE y-coordinate less than 0.2. In one embodiment, the first emitting compound emits light having a CIE x-coordinate less than 0.2 and a CIE y-coordinate less than 0.15.

In one aspect, the first emitting compound has less than 2 microsecond of the fastest component of its photoluminescence transient that fits to a multiple exponential function at room temperature under inert atmosphere. In one embodiment, the first emitting compound has less than 1 microsecond of the fastest component of its photoluminescence transient that fits to a multiple exponential function at room temperature under inert atmosphere. In one embodiment, the first emitting compound has less than 0.5 microsecond of the fastest component of its photoluminescence transient that fits to a multiple exponential function at room temperature under inert atmosphere.

In one aspect, the first emitting compound has PLQY of less than 80% at room temperature. In one embodiment, the first emitting compound has PLQY of less than 70% at room temperature. In one embodiment, the first emitting compound has PLQY of less than 60% at room temperature. In one embodiment, the first emitting compound has PLQY of less than 50% at room temperature. In one embodiment, the first emitting compound has PLQY of less than 40% at room temperature.

In one aspect, the OLED has an external quantum efficiency of between 8% and 18% at 1 mA/cm². In one embodiment, the OLED has an external quantum efficiency of between 8% and 15% at 1 mA/cm². In one embodiment, the OLED has an external quantum efficiency of between 8% and 13% at 1 mA/cm². In one embodiment, the OLED has an external quantum efficiency of between 8% and 11% at 1 mA/cm². In one embodiment, the OLED has an external quantum efficiency of between 8% and 10% at 1 mA/cm².

In one aspect, the M is selected from the group consisting of Ir, Rh, Re, Ru, Os, Pt, Au, and Cu. In one embodiment, the M is Ir. In one embodiment, the M is Pt.

In one aspect, the first emitting compound has the formula of $Ir(L^1)_2(L^2)$. In one embodiment, the first emitting compound has the formula of $Ir(L^1)_3$. In one embodiment, the first emitting compound has the formula of $Ir(L^1)(L^2)(L^3)$. In one embodiment, $L^1$, $L^2$ and $L^3$ are each independently selected from the group consisting of:

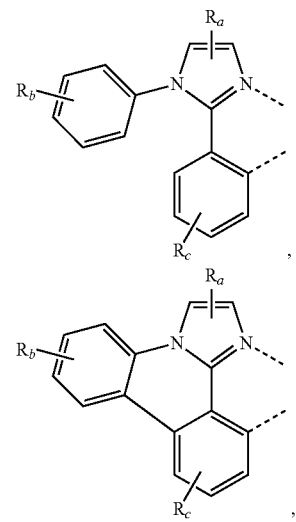

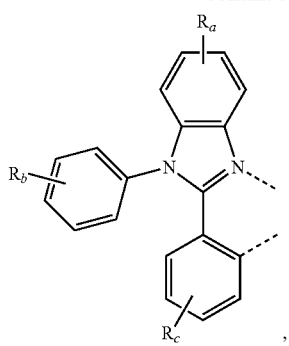
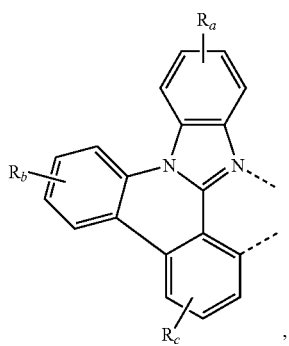
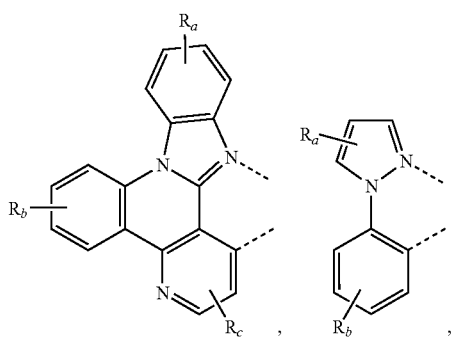
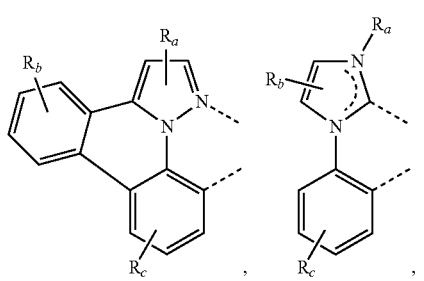
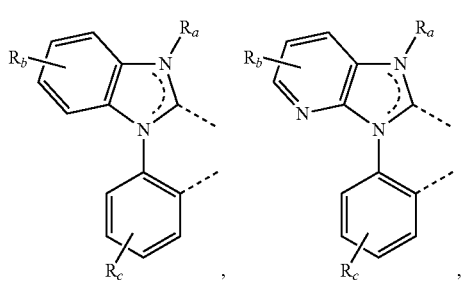
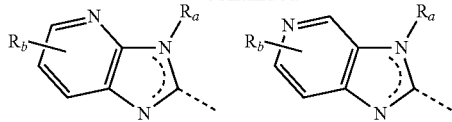
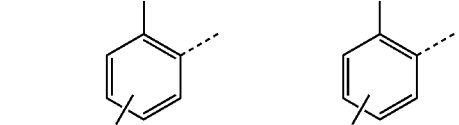
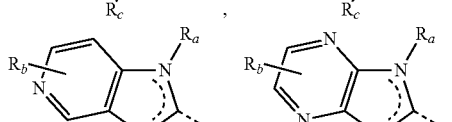
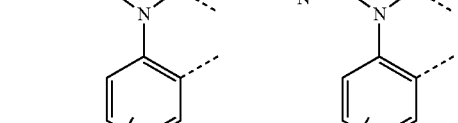
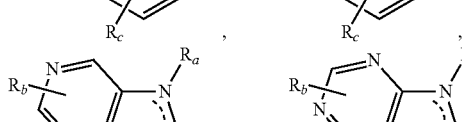
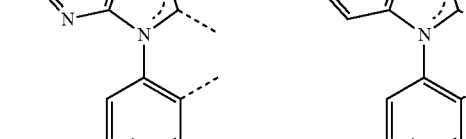
, and .
In one embodiment, the first emitting compound has the formula of $Pt(L^1)_2$ or $Pt(L^1)(L^2)$.
In one embodiment, at least one of $L^1$, $L^2$ and $L^3$ is:
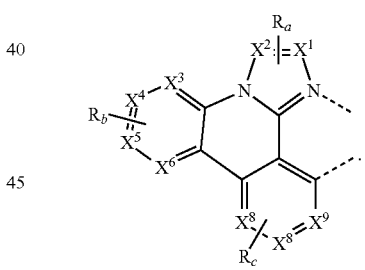
In another embodiment, at least one of $L^1$, $L^2$ and $L^3$ is:
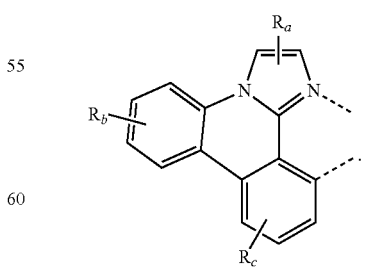
In one aspect, the first emitting compound has a structure $(L_A)_n ML_m$ according to Formula 1 shown below is disclosed.

Formula 1

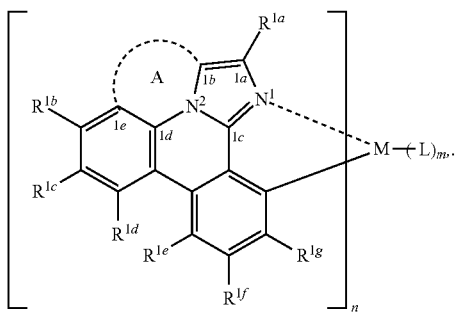

In Formula I, M is a metal having an atomic weight greater than 40, n has a value of at least 1 and m+n is the maxiumn number of ligands that may be attached to the metal; wherein A is a linking group having two to three linking atoms, wherein the linking atoms are each independently selected from the group consisting of C, Si, O, S, N, B or combinations thereof;

wherein $R^{1a}$ to $R^{1g}$ are each independently selected from the group consisting of hydrogen, deuterium, alkyl, cycloalkyl, heteroalkyl, alkoxy, aryloxy, amino, silyl, alkenyl, cycloalkenyl, heteroalkenyl, alkynyl, aralkyl, CN, $CF_3$, $CO_2R$, $C(O)R$, $C(O)NR_2$, $NR_2$, $NO_2$, OR, SR, $SO_2$, SOR, $SO_3R$, halo, aryl, heteroaryl, a heterocyclic group, and combinations thereof;

wherein each R is independently selected from the group consisting of hydrogen, deuterium, halo, alkyl, cycloalkyl, heteroalkyl, alkoxy, aryloxy, amino, silyl, alkenyl, cycloalkenyl, heteroalkenyl, alkynyl, aralkyl, aryl, heteroaryl, and combinations thereof;

wherein any one of the ring atoms to which $R^{1b}$ to $R^{1g}$ are attached may be replaced with a nitrogen atom, wherein when the ring atom is replaced with a nitrogen atom the corresponding R group is not present; and wherein L is a substituted or unsubstituted cyclometallated ligand.

In some embodiments of the compound of Formula 1, the linking atoms form at least one single bond between two linking atoms.

In some embodiments of the compound of Formula 1, one of the ring atoms to which $R^{1b}$ to $R^{1g}$ are attached is a nitrogen atom. In some embodiments, the ring atom to which $R^{1e}$ is attached a nitrogen atom.

In one embodiment, the compound has a triplet excited state and wherein the linking group A stabilizes the bond between $N^2$ and $C^{1b}$ from cleavage when the compound is in the triplet excited state.

In one embodiment, the compound has a peak emissive wavelength less than 500 nm. In another embodiment, the compound has a peak emissive wavelength less than 480 nm. In yet another embodiment, the compound has a peak emissive wavelength ranging from 400 nm to 500 nm.

In some embodiments of the compound of Formula 1, the linking group A is a saturated group.

In one embodiment of the compound of Formula 1, the linking group A is independently selected from the group consisting of —$CR^1R^2$—$CR^3R^4$—, —$CR^1R^2$—$CR^3R^4$—$CR^5R^6$—, —$CR^1R^2$—$NR^3$—, —$CR^1$=$CR^2CR^3R^4$—, —O—$SiR^1R^2$—, —$CR^1R^2$—O—, and —C—$SiR^1R^2$—, wherein the substituents $R^1$ to $R^6$ can be same or different, and are independently selected from the group consisting of hydrogen, deuterium, alkyl, cycloalkyl, aryl, heteroaryl, and combinations thereof; wherein any adjacent $R^1$ to $R^6$ are optionally connected to form a saturated five membered ring or a saturated six membered ring. Any adjacent substituents refers to any two of substituents that are possible to form the ring. The two adjacent substituents can be on the same atom, or on different atoms. The linking group A can be selected from the group consisting of:

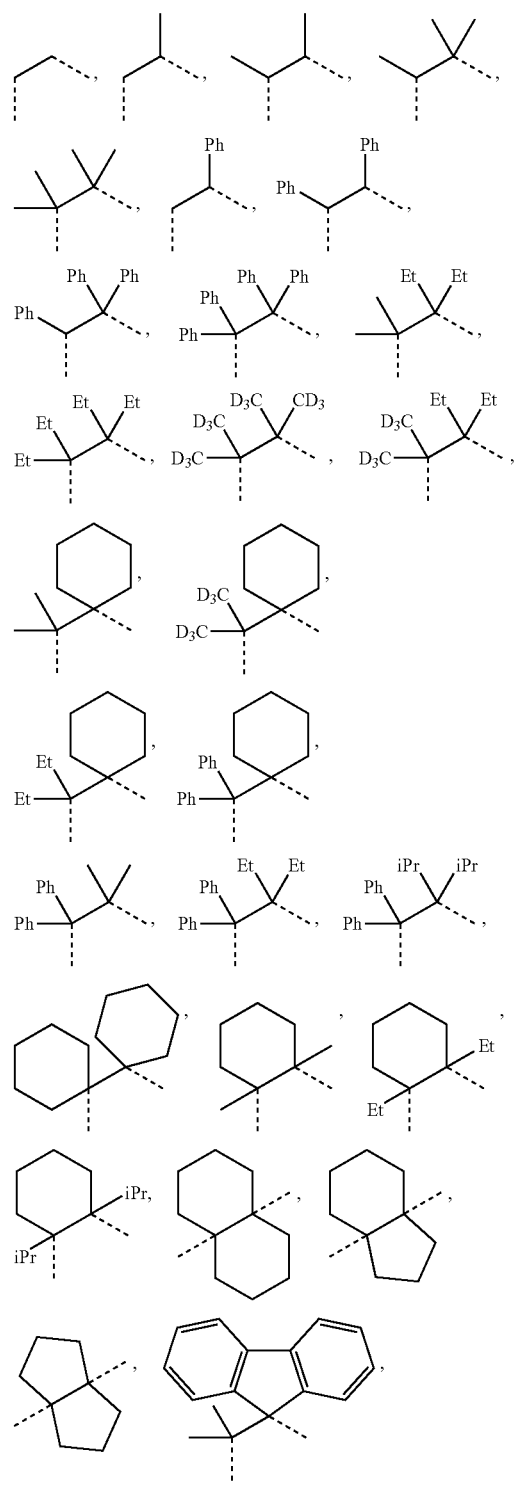

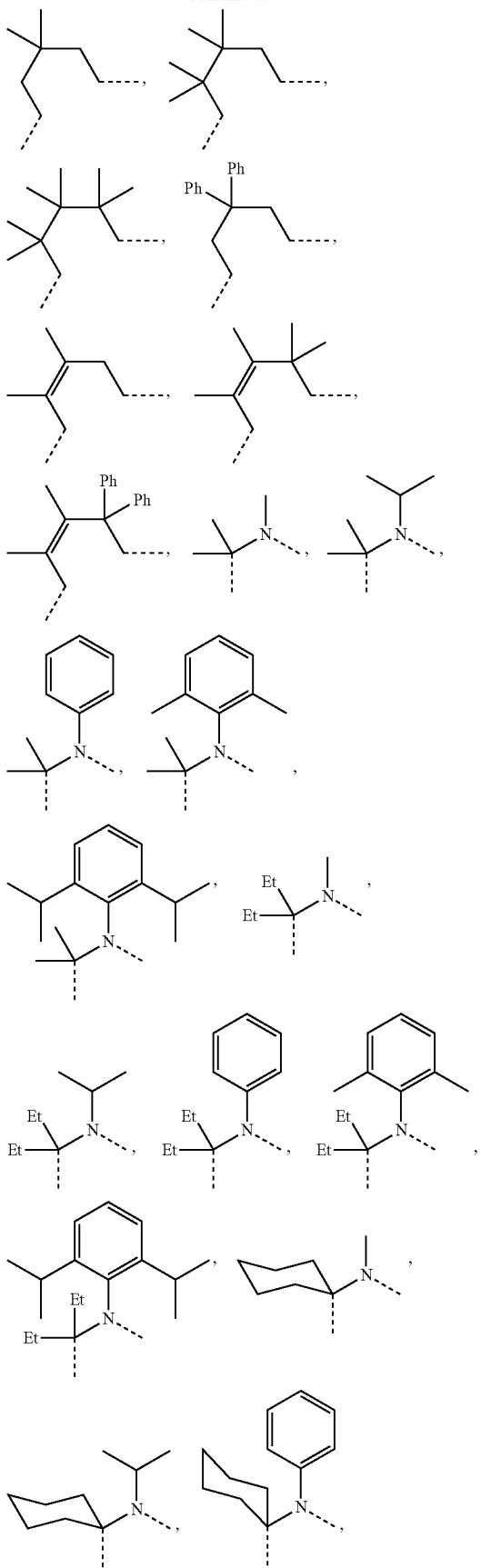
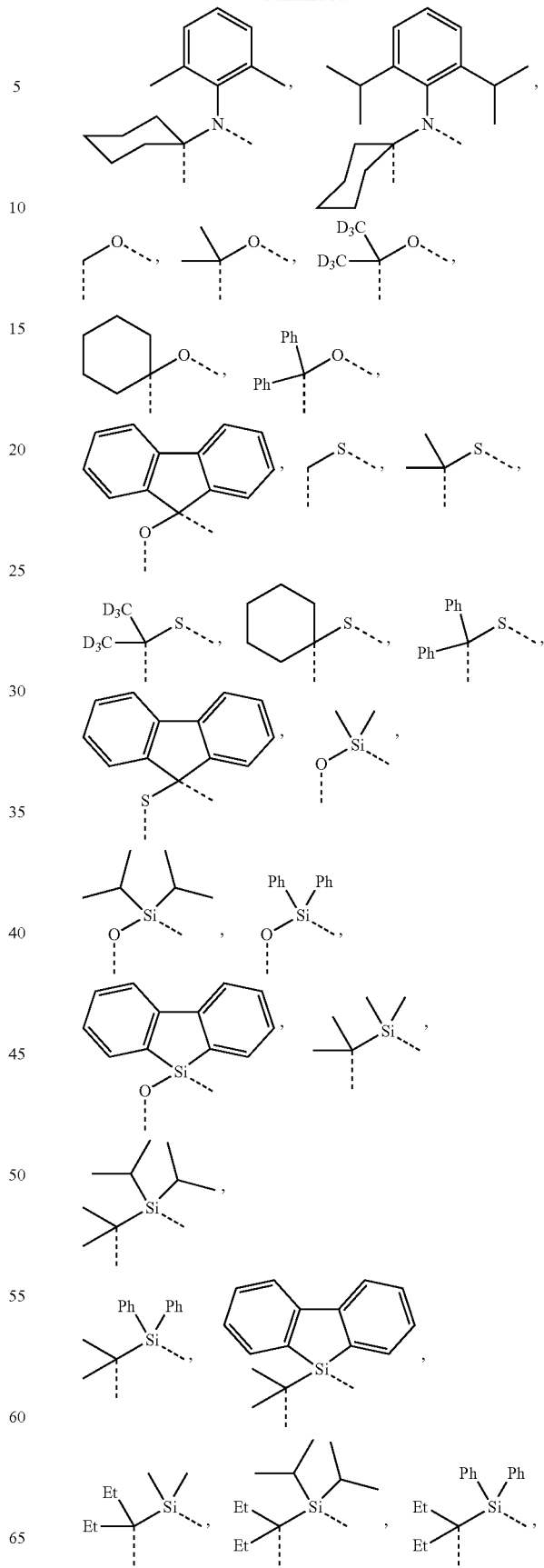

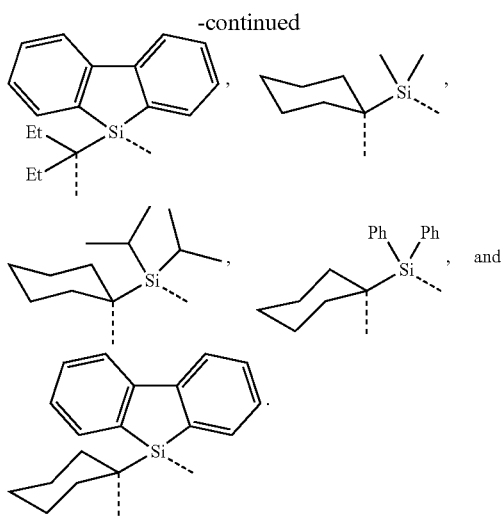

In some embodiments where the linking group A is independently selected from the group consisting of —CR$^1$R$^2$—CR$^3$R$^4$—, —CR$^1$R$^2$—CR$^3$R$^4$—CR$^5$R$^6$—, —CR$^1$R$^2$—NR$^3$—, —CR$^1$=CR$^2$—CR$^3$R$^4$—, —O—SiR$^1$R$^2$—, —CR$^1$R$^2$—S—, —CR$^1$R$^2$—O—, and —C—SiR$^1$R$^2$—, wherein the substituents R$^1$ to R$^6$ can be same or different, and are independently selected from the group consisting of hydrogen, deuterium, alkyl, cycloalkyl, aryl, heteroaryl, and combinations thereof; at least one adjacent R$^1$ to R$^6$ are connected to form a saturated five membered ring or a saturated six membered ring. In some embodiments, at least two adjacent R$^1$ to R$^6$, if present, are connected to form a saturated five membered ring or a saturated six membered ring. In some embodiments, each R$^1$ to R$^6$ are independently selected from the group consisting of alkyl, cycloalkyl, aryl, heteroaryl, partially or fully deuterated variants thereof, and combinations thereof; wherein any adjacent R$^1$ to R$^6$ are optionally connected to form a saturated five membered ring or a saturated six membered ring.

In some embodiments where the linking group A is independently selected from the group consisting of —CR$^1$R$^2$—CR$^3$R$^4$—, —CR$^1$R$^2$—CR$^3$R$^4$—CR$^5$R$^6$—, —CR$^1$R$^2$—NR$^3$—, —CR$^1$=CR$^2$—CR$^3$R$^4$—, —O—SiR$^1$R$^2$—, —CR$^1$R$^2$—S—, —CR$^1$R$^2$—O—, and —C—SiR$^1$R$^2$—, wherein the substituents R$^1$ to R$^6$ can be same or different, and are independently selected from the group consisting of hydrogen, deuterium, alkyl, cycloalkyl, aryl, heteroaryl, and combinations thereof; each R$^1$ to R$^6$ are independently selected from the group consisting of methyl, ethyl, propyl, 1-methylethyl, butyl, 1-methylpropyl, 2-methylpropyl, pentyl, 1-methylbutyl, 2-methylbutyl, 3-methylbutyl, 1,1-dimethylpropyl, 1,2-dimethylpropyl, 2,2-dimethylpropyl, cyclopentyl, cyclohexyl, phenyl, 2,6-dimethylphenyl, 2,4,6-trimethylphenyl, 2,6-diisopropylphenyl, partially or fully deuterated variants thereof and combinations thereof. In some embodiments, each R$^1$ to R$^6$ are independently selected from the group consisting of alkyl, partially or fully deuterated variants thereof, and combinations thereof; wherein any adjacent R$^1$ to R$^6$ are optionally connected to form a saturated five membered ring or a saturated six membered ring.

In some embodiments of the compound of Formula 1, at least one of R$^{1a}$ to R$^{1g}$ is selected from the group consisting of alkyl, cycloalkyl, aryl, heteroaryl, partially or fully deuterated variants thereof, and combinations thereof. In other embodiments, at least one of R$^{1b}$, R$^{1d}$ and R$^{1e}$ is selected from the group consisting of alkyl, cycloalkyl, aryl, heteroaryl, partially or fully deuterated variants thereof, and combinations thereof. In other embodiments, R$^{1d}$ is selected from the group consisting of alkyl, cycloalkyl, aryl, heteroaryl, partially or fully deuterated variants thereof, and combinations thereof. In other embodiments, R$^{1a}$ is selected from the group consisting of alkyl, cycloalkyl, aryl, heteroaryl, partially or fully deuterated variants thereof, and combinations thereof.

In some embodiments of the compound of Formula 1, the metal M is selected from the group consisting of Re, Ru, Os, Rh, Ir, Pd, Pt, and Au. In some embodiments, the metal M is selected from the group consisting of Ir and Pt.

In some embodiments of the compound of Formula 1, the compound is (L$_A$)$_3$Ir, or (L$_A$)Ir(L)$_2$ or (L$_A$)$_2$Ir(L).

In some embodiments of the compound of Formula 1, the compound has a structure of Formula 2:

Formula 2

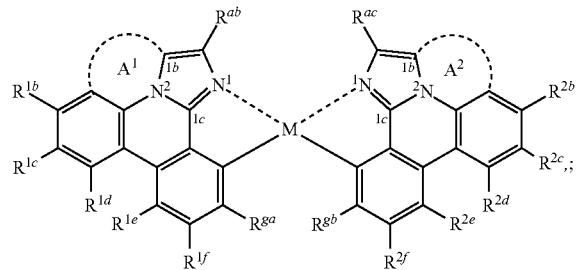

wherein M is Pt;

wherein A$^1$ and A$^2$ are each independently a first linking group having two to three linking atoms, wherein the linking atoms are each independently selected from the group consisting of C, Si, O, S, N, B or combinations thereof;

wherein R$^{1b}$ to R$^{1f}$ and R$^{2b}$ to R$^{2f}$ are each independently selected from the group consisting of hydrogen, deuterium, alkyl, cycloalkyl, heteroalkyl, alkoxy, aryloxy, amino, silyl, alkenyl, cycloalkenyl, heteroalkenyl, alkynyl, aralkyl, CN, CF$_3$, CO$_2$R, C(O)R, C(O)NR$_2$, NR$_2$, NO$_2$, OR, SR, SO$_2$, SOR, SO$_3$R, halo, aryl, heteroaryl, a heterocyclic group, and combinations thereof;

wherein each R is independently selected from the group consisting of hydrogen, deuterium, halo, alkyl, cycloalkyl, heteroalkyl, alkoxy, aryloxy, amino, silyl, alkenyl, cycloalkenyl, heteroalkenyl, alkynyl, aralkyl, aryl, heteroaryl, and combinations thereof;

wherein any one of the ring atoms to which R$^{1b}$ to R$^{1f}$ and R$^{2b}$ to R$^{2f}$ are attached may be replaced with a nitrogen atom, wherein when the ring atom is replaced with a nitrogen atom the corresponding R group is not present; and wherein R$^{ab}$ and R$^{ac}$ and/or R$^{ga}$ and R$^{gb}$ may bond to form a second linking group having one to three linking atoms each independently selected from the group consisting of B, N, P, O, S, Se, C, Si, Ge or combinations thereof.

In some embodiments of the compound of Formula 2, each of the first linking groups A$^1$ and A$^2$ is independently selected from the group consisting of —CR$^1$R$^2$—CR$^3$R$^4$—, —CR$^1$R$^2$—CR$^3$R$^4$—CR$^5$R$^6$—, —CR$^1$R$^2$—NR$^3$—, —CR$^1$=CR$^2$—CR$^3$R$^4$—, —O—SiR$^1$R$^2$—, —CR$^1$R$^2$—S—, —CR$^1$R$^2$—O—, and —C—SiR$^1$R$^2$—, wherein each R$^1$ to R$^6$ can be same or different, and are independently selected from the group consisting of hydrogen, deuterium, alkyl, cycloalkyl, aryl, heteroaryl, and combinations thereof; and wherein any adjacent $R^1$ to $R^6$ are optionally connected to form a saturated five membered ring or a saturated six membered ring.

In some embodiments of the compound of Formula 2, the compound has a triplet excited state and wherein the linking group stabilizes the bond between $N^2$ and $C^{1b}$ from cleavage when the compound is in the triplet excited state.

In some embodiments of the compound of Formula 2, the compound has a peak emissive wavelength less than 500 nm. In some embodiments, the compound has a peak emissive wavelength less than 480 nm. In some embodiments, the compound has a peak emissive wavelength ranging from 400 nm to 500 nm.

In some embodiments of the compound of Formula 2, each of the first linking groups $A^1$ and $A^2$ is independently selected from the Linker Group consisting of:

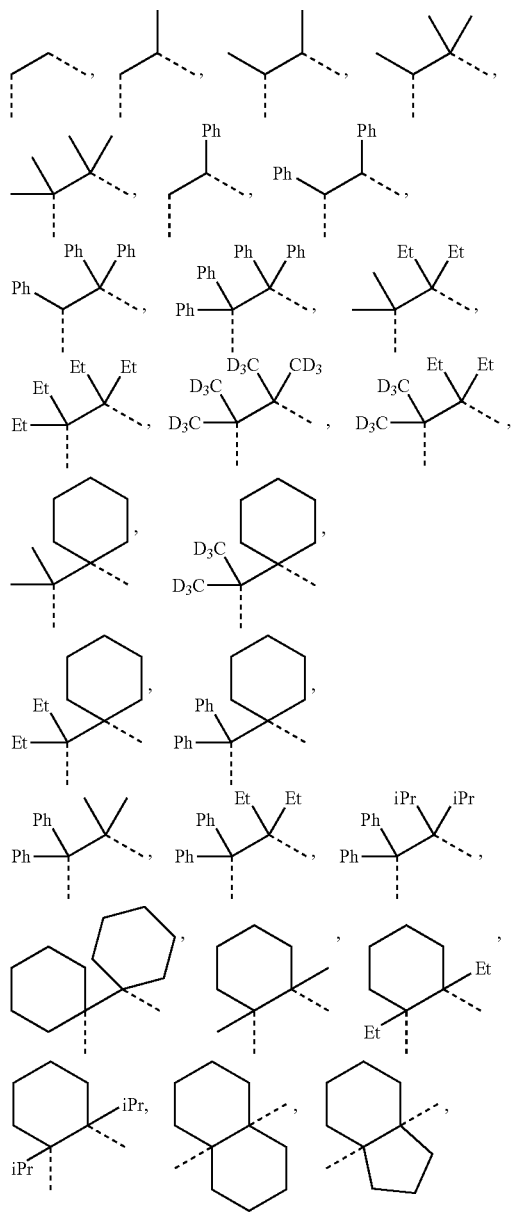

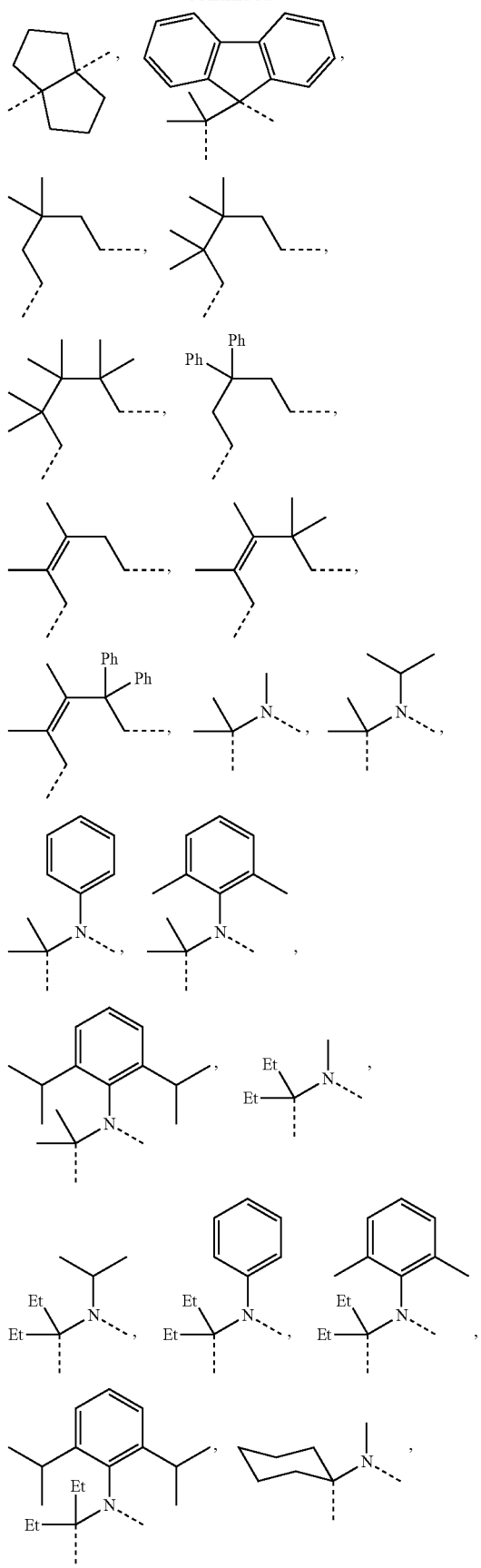

-continued

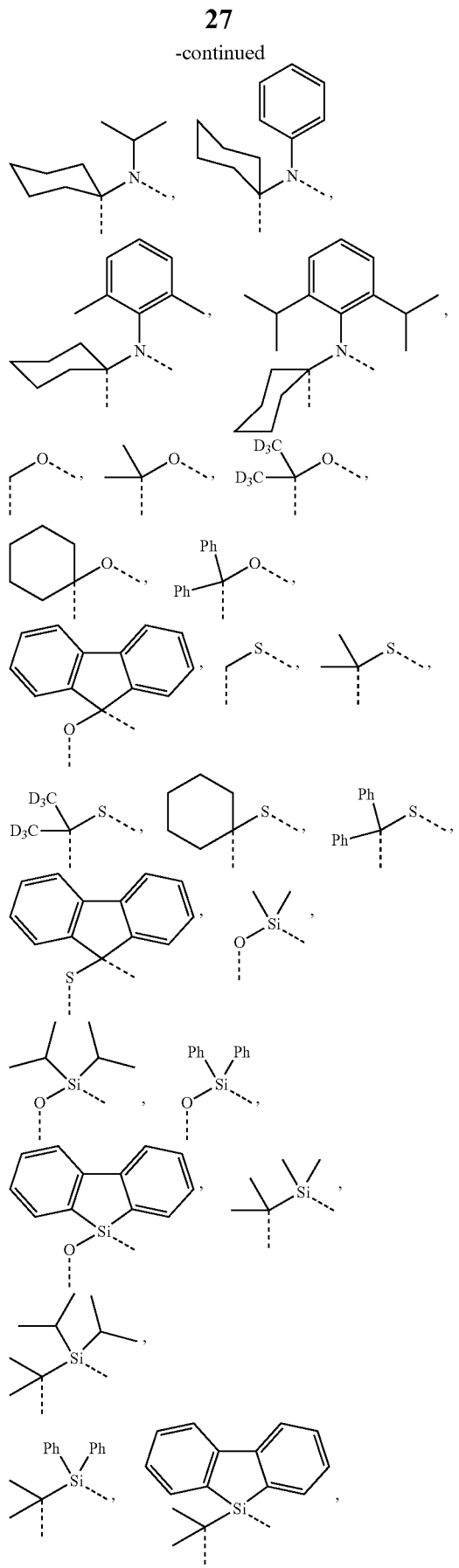

-continued

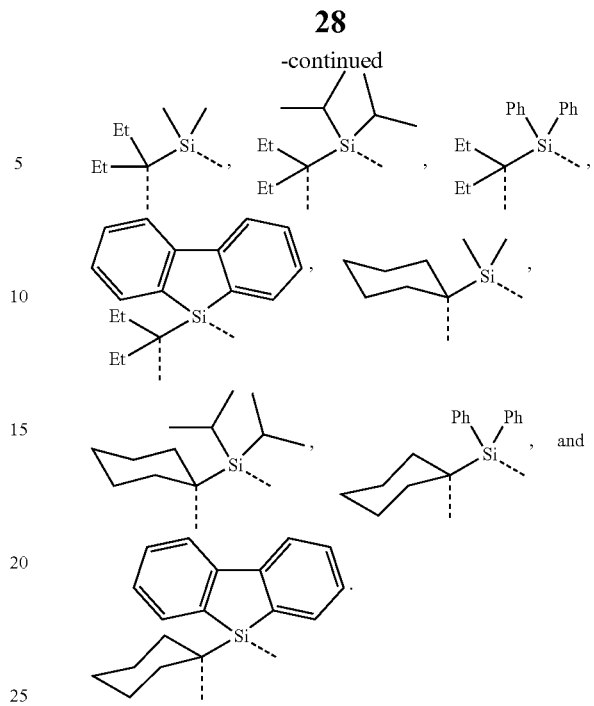

In some embodiments of the compound of Formula 2, the second linking group is independently selected from the group consisting of: $BR^1$, $NR^1$, $PR^1$, O, S, Se, C=O, S=O, $SO_2$, $CR^1R^2$, —$CR^1R^2$—$CR^3R^4$—, —$CR^1R^2$—$CR^3R^4$—$CR^5R^6$—, —$CR^1R^2$—$NR^3$—, —$CR^1$=$CR^2$—$CR^3R^4$—, —O—$SiR^1R^2$—, —$CR^1R^2$—S—, —$CR^1R^2$—O—, —C—$SiR^1R^2$—, $SiR^1R^2$, and $GeR^1R^2$, wherein each $R^1$ to $R^6$ can be same or different, and are independently selected from the group consisting of hydrogen, deuterium, alkyl, cycloalkyl, alkenyl, alkenyl, alkynyl, heteroalkyl, aralkyl, aryl, heteroaryl, and combinations thereof; and wherein any adjacent $R^1$ to $R^6$ are optionally connected to form a saturated five membered ring or a saturated six membered ring.

In some embodiments of the compound of Formula 1, the compound has Formula 3:

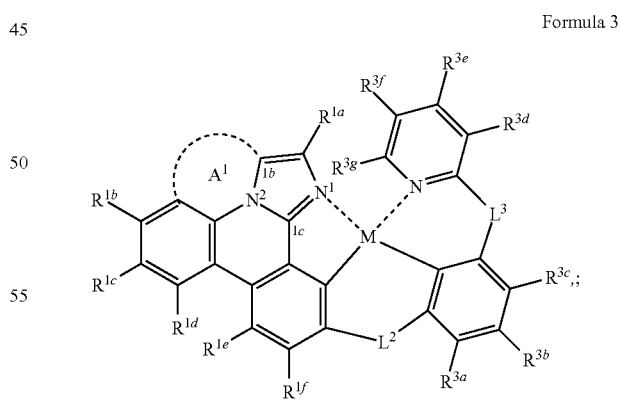

Formula 3 wherein M is Pt;
wherein $L^2$ and $L^3$ are each independently selected from the group consisting of a single bond, BR, NR, PR, O, S, Se, C—O, S—O, $SO_2$, $CR^1R^2$, $SiR^1R^2$, and $GeR^1R^2$;
wherein $R^{3a}$ to $R^{3f}$, are each independently selected from the group consisting of hydrogen, deuterium, alkyl, cycloalkyl, heteroalkyl, alkoxy, aryloxy, amino, silyl, alkenyl, cycloalkenyl, heteroalkenyl, alkynyl, aralkyl, CN, $CF_3$, $CO_2R$, $C(O)R$, $C(O)NR_2$, $NR_2$, $NO_2$, OR, SR, $SO_2$, SOR, $SO_3R$, halo, aryl, heteroaryl, a heterocyclic group, and combinations thereof;

wherein each R is independently selected from the group consisting of hydrogen, deuterium, halo, alkyl, cycloalkyl, heteroalkyl, alkoxy, aryloxy, amino, silyl, alkenyl, cycloalkenyl, heteroalkenyl, alkynyl, aralkyl, aryl, heteroaryl, and combinations thereof;

wherein any two adjacent $R^{1f}$, $R^{3a}$, $R^{3c}$, $R^{3d}$, $R^1$ and $R^2$ are optionally joined to form a ring; wherein $L^2$ and $R^{1f}$, $L^2$ and $R^{3a}$, or $L^2$ and both $R^{1f}$ and $R^{3a}$ are optionally joined to form one or more rings; and wherein $L^3$ and $R^{3c}$, $L^3$ and $R^{3d}$, or $L^3$ and both $R^{3c}$ and $R^{3d}$ are optionally joined to form one or more rings.

In some embodiments of the compound of Formula 3, $L^2$ and $L^3$ are each indpendently selected from the group consisting of $BR^1$, $NR^1$, $PR^1$, O, S, Se, C=O, S=O, $SO_2$, $CR^1R^2$, $SiR^1R^2$, and $GeR^1R^2$. In some embodiments of the compound of Formula 3, $R^{1f}$ or $R^{3a}$ and $R^1$ or $R^2$ are joined to form a ring. In some embodiments of the compound of Formula 3, $R^{3c}$ or $R^{3d}$ and $R^1$ or $R^2$ are joined to forma ring.

In some embodiments of the OLED, the OLED is incorporated into a device selected from the group consisting of a consumer product, an electronic component module, and a lighting panel.

Generally, an organic layer suitable for use in the organic electroluminescence device of the present may have any suitable configuration of layer depending, for example, on application and purpose of the organic electroluminescence device. Accordingly, in some embodiments of the organic electroluminescence device, the organic layer is formed on a transparent electrode or a semitransparent electrode. In some such embodiments, the organic layer is formed on a top surface or any suitable surface of the transparent electrode or the semitransparent electrode. Also, suitable shape, size and/or thickness of the organic layer may be employed depending, for example, on application and the purpose of the organic electroluminescence device. Specific examples of configurations of an organic electroluminescence device of the present invention, having a substrate, a cathode, an anode and an organic layer include, but are not limited to, the following:

(A) Anode/hole transporting layer/light emitting layer/electron transporting layer/cathode;

(B) Anode/hole transporting layer/light emitting layer/block layer/electron transporting layer/cathode;

(C) Anode/hole transporting layer/light emitting layer/block layer/electron transporting layer/electron injection layer/cathode;

(D) Anode/hole injection layer/hole transporting layer/light emitting layer/block layer/electron transporting layer/cathode; and (E) Anode/hole injection layer/hole transporting layer/light emitting layer/block layer/electron transporting layer/electron injection layer/cathode.

(F) Anode/hole injection layer/electron blocking layer/hole transporting layer/light emitting layer/block layer/electron transporting layer/electron injection layer/cathode.

Additional device configuration, including substrate, cathode and anode of an organic electroluminescence device, is described in Japanese Patent Publication No. 2008-270736.

<Substrate>

A suitable substrate usable in an organic electroluminescence device of the present invention is preferably a substrate which does not scatter or decrease light emitted from an organic layer when used for display applications. When used for lighting or certain display applications, substrates that scatter light are acceptable. In some embodiments, the substrate preferably is composed of an organic material which exhibits superior heat resistance, dimensional stability, solvent resistance, electrical insulating property and/or processability.

The substrate suitable for use in the present invention is preferably one which does not scatter or attenuate light emitted from the organic compound layer. Specific examples of materials for the substrate, include but are not limited to, inorganic materials such as zirconia-stabilized yttrium (YSZ) and glass; polyesters such as polyethylene terephthalate, polybutylene phthalate, and polyethylene naphthalate; and organic materials such as polystyrene, polycarbonate, polyethersulfone, polyarylate, polyimide, polycycloolefin, norbornene resin, polychlorotrifluoroethylene, and the like.

In some embodiments, when glass is used as the substrate, alkali free glass is preferably used. Specific examples of suitable alkali free glass are found in US patent application publication no. 2013/0237401 by Takahiro Kawaguchi, which published Sep. 12, 2013. In some embodiments, when soda-lime glass is used as the substrate, it is preferred to use glass on which a barrier coat of silica or the like has been applied. In some embodiments, when an organic material is used as the substrate, it is preferred to use a material having one or more of the attributes: excellent in heat resistance, dimensional stability, solvent resistance, electric insulation performance, and workability.

Generally, there is no particular limitation as to the shape, the structure, the size or the like of the substrate, but any of these attributes may be suitably selected according to the application, purposes and the like of the light-emitting element. n general, a plate-like substrate is preferred as the shape of the substrate. A structure of the substrate may be a monolayer structure or a laminate structure. Furthermore, the substrate may be formed from a single member or two or more members.

Although the substrate may be transparent and colorless, or transparent and colored, it is preferred that the substrate is transparent and colorless from the viewpoint that the substrate does not scatter or attenuate light emitted from the organic light-emitting layer. In some embodiments, a moisture permeation preventive layer (gas barrier layer) may be provided on the top surface or the bottom surface of the substrate. Examples of a material of the moisture permeation preventive layer (gas barrier layer), include, but are not limited to, inorganic substances such as silicon nitride and silicon oxide. The moisture permeation preventive layer (gas barrier layer) may be formed in accordance with, for example, a high-frequency sputtering method or the like.

In the case of applying a thermoplastic substrate, a hard-coat layer or an under-coat layer may be further provided as needed.

<Anode>

Any anode may be used in an organic electroluminescence device of the present invention so long as it serves as an electrode supplying holes into an organic layer. In some embodiments of the organic electroluminescence device of the present invention, any suitable shape, structure and/or size of known electrode material may be used depending, for example, on the application and purpose of the organic electroluminescence device. In some embodiments, a transparent anode is preferred.

The anode may generally be any material as long as it has a function as an electrode for supplying holes to the organic compound layer, and there is no particular limitation as to the shape, the structure, the size or the like. However, it may be suitably selected from among well-known electrode materials according to the application and purpose of the light-emitting element. In some embodiments, the anode is provided as a transparent anode.

Materials for the anode preferably include, for example, metals, alloys, metal oxides, electric conductive compounds, and mixtures thereof. Materials having a work function of 4.0 eV or more are preferable. Specific examples of the anode materials include electric conductive metal oxides such as tin oxides doped with antimony, fluorine or the like (ATO and FTO), tin oxide, zinc oxide, indium oxide, indium tin oxide (ITO), and indium zinc oxide (IZO); metals such as gold, silver, chromium, aluminum, copper, and nickel; mixtures or laminates of these metals and the electric conductive metal oxides; inorganic electric conductive materials such as copper iodide and copper sulfide; organic electric conductive materials such as polyaniline, polythiophene, and polypyrrole; and laminates of these inorganic or organic electron-conductive materials with ITO. Among these, the electric conductive metal oxides are preferred, and particularly, ITO is preferable in view of productivity, high electric conductivity, transparency and the like.

The anode may be formed on the substrate in accordance with a method which is appropriately selected from among wet methods such as printing methods, coating methods and the like; physical methods such as vacuum deposition methods, sputtering methods, ion plating methods and the like; and chemical methods such as CVD (chemical vapor deposition) and plasma CVD methods and the like, in consideration of the suitability to a material constituting the anode. For instance, when ITO is selected as a material for the anode, the anode may be formed in accordance with a DC or high-frequency sputtering method, a vacuum deposition method, an ion plating method or the like.

In the organic electroluminescence element of the present invention, a position at which the anode is to be formed is not particularly limited, but it may be suitably selected according to the application and purpose of the light-emitting element. The anode may be formed on either the whole surface or a part of the surface on either side of the substrate.

For patterning to form the anode, a chemical etching method such as photolithography, a physical etching method such as etching by laser, a method of vacuum deposition or sputtering through superposing masks, or a lift-off method or a printing method may be applied.

A thickness of the anode may be suitably selected according to the material constituting the anode and is therefore not definitely decided, but it is usually in a range of from 10 nm to 50 µm, and preferably from 50 nm to 20 µm. The thickness of the anode layer may be properly controlled depending on the material used therefor. The resistance of the anode is preferably $10^2$ Ω/square or less, and more preferably 30 Ω/square or less. In the case where the anode is transparent, it may be either transparent and colorless, or transparent and colored. For extracting luminescence from the transparent anode side, it is preferred that a light transmittance of the anode is 60% or higher, and more preferably 70% or higher. A detailed description of transparent anodes can be found in "TOUMEI DENNKYOKU-MAKU NO SHINTENKAI (Novel Developments in Transparent Electrode Films)" edited by Yutaka Sawada, published by C.M.C. in 1999.

In the case where a plastic substrate having a low heat resistance is used in the present invention, it is preferred that ITO or IZO is used to obtain a transparent anode prepared by forming the film at a low temperature of 150° C. or lower.

<Cathode>

Any cathode may be used in an organic electroluminescence device of the present invention so long as it serves as an electrode supplying electrons into the organic layer. In some embodiments of the organic electroluminescence device of the present invention, any suitable shape, structure and/or size of known electrode material may be used depending, for example, on the application and purpose of the organic electroluminescence device. In some embodiments, a transparent cathode is preferred.

The cathode may generally be any material as long as it has a function as an electrode for injecting electrons to the organic compound layer, and there is no particular limitation as to the shape, the structure, the size or the like. However it may be suitably selected from among well-known electrode materials according to the application and purpose of the light-emitting element.

Materials constituting the cathode include, for example, metals, alloys, metal oxides, electric conductive compounds, and mixtures thereof. Materials having a work function of 4.0 eV or more are preferable. Specific examples thereof include alkali metals (e.g., Li, Na, K, Cs or the like), alkaline earth metals (e.g., Mg, Ca or the like), gold, silver, lead, aluminum, sodium-potassium alloys, lithium-aluminum alloys, magnesium-silver alloys, rare earth metals such as indium, and ytterbium, and the like. They may be used alone, but it is preferred that two or more of them are used in combination from the viewpoint of satisfying both stability and electron injectability.

In some embodiments, as the materials for constituting the cathode, alkaline metals or alkaline earth metals are preferred in view of electron injectability, and materials containing aluminum as a major component are preferred in view of excellent preservation stability.

The term "material containing aluminum as a major component" refers to a material constituted by aluminum alone; alloys comprising aluminum and 0.01% by weight to 10% by weight of an alkaline metal or an alkaline earth metal; or mixtures thereof (e.g., lithium-aluminum alloys, magnesium-aluminum alloys and the like). Exemplary materials for the cathode are described in detail in JP-A Nos. 2-15595 and 5-121172.

A method for forming the cathode is not particularly limited, but it may be formed in accordance with a well-known method. For instance, the cathode may be formed in accordance with a method which is appropriately selected from among wet methods such as printing methods, coating methods and the like; physical methods such as vacuum deposition methods, sputtering methods, ion plating methods and the like; and chemical methods such as CVD and plasma CVD methods and the like, in consideration of the suitability to a material constituting the cathode. For example, when a metal (or metals) is (are) selected as a material (or materials) for the cathode, one or two or more of them may be applied at the same time or sequentially in accordance with a sputtering method or the like.

For patterning to form the cathode, a chemical etching method such as photolithography, a physical etching method such as etching by laser, a method of vacuum deposition or sputtering through superposing masks, or a lift-off method or a printing method may be applied.

In the present invention, a position at which the cathode is to be formed is not particularly limited, and it may be formed on either the whole or a part of the organic compound layer.

Furthermore, a dielectric material layer made of fluorides, oxides or the like of an alkaline metal or an alkaline earth metal may be inserted between the cathode and the organic compound layer with a thickness of from 0.1 nm to 5 nm. The dielectric material layer may be considered to be a kind of electron injection layer. The dielectric material layer may be formed in accordance with, for example, a vacuum deposition method, a sputtering method, an ionplating method or the like.

A thickness of the cathode may be suitably selected according to materials for constituting the cathode and is therefore not definitely decided, but it is usually in a range of from 10 nm to 5 µm, and preferably from 50 nm to 1 µm.

Moreover, the cathode may be transparent or opaque. A transparent cathode may be formed by preparing a material for the cathode with a small thickness of from 1 nm to 10 nm, and further laminating a transparent electric conductive material such as ITO or IZO thereon.

<Protective Layer>

A whole body of the organic EL element of the present invention may be protected by a protective layer. Any materials may be applied in the protective layer as long as the materials have a function to protect a penetration of ingredients such as moisture, oxygen or the like which accelerates deterioration of the element into the element. Specific examples of materials for the protective layer include metals such as In, Sn, Pb, Au, Cu, Ag, Al, Ti, Ni and the like; metal oxides such as MgO, SiO, $SiO_2$, $Al_2O_3$, GeO, NiO, CaO, BaO, $Fe_2O_3$, $Y_2O_3$, $TiO_2$ and the like; metal nitrides such as $SiN_x$, $SiN_xO_y$, and the like; metal fluorides such as $MgF_2$, LiF, $AlF_3$, $CaF_2$ and the like; polyethylene; polypropylene; polymethyl methacrylate; polyimide; polyurea; polytetrafluoroethylene; polychlorotrifluoroethylene; polydichlorodifluoroethylene; a copolymer of chlorotrifluoroethylene and dichlorodifluoroethylene; copolymers obtained by copolymerizing a monomer mixture containing tetrafluoroethylene and at least one comonomer; fluorine-containing copolymers each having a cyclic structure in the copolymerization main chain; water-absorbing materials each having a coefficient of water absorption of 1% or more; moisture permeation preventive substances each having a coefficient of water absorption of 0.1% or less; and the like.

There is no particular limitation as to a method for forming the protective layer. For instance, a vacuum deposition method, a sputtering method, a reactive sputtering method, an MBE (molecular beam epitaxial) method, a cluster ion beam method, an ion plating method, a plasma polymerization method (high-frequency excitation ion plating method), a plasma CVD method, a laser CVD method, a thermal CVD method, a gas source CVD method, a coating method, a printing method, or a transfer method may be applied.

<Sealing>

The whole organic electroluminescence element of the present invention may be sealed with a sealing cap. Furthermore, a moisture absorbent or an inert liquid may be used to seal a space defined between the sealing cap and the light-emitting element. Although the moisture absorbent is not particularly limited, specific examples thereof include barium oxide, sodium oxide, potassium oxide, calcium oxide, sodium sulfate, calcium sulfate, magnesium sulfate, phosphorus pentaoxide, calcium chloride, magnesium chloride, copper chloride, cesium fluoride, niobium fluoride, calcium bromide, vanadium bromide, molecular sieve, zeolite, magnesium oxide and the like. Although the inert liquid is not particularly limited, specific examples thereof include paraffins; liquid paraffins; fluorine-based solvents such as perfluoroalkanes, perfluoroamines, perfluoroethers and the like;

chlorine-based solvents; silicone oils; and the like.

<Driving>

In the organic electroluminescence element of the present invention, when a DC (AC components may be contained as needed) voltage (usually 2 volts to 15 volts) or DC is applied across the anode and the cathode, luminescence can be obtained. For the driving method of the organic electroluminescence element of the present invention, driving methods described in JP-A Nos. 2-148687, 6-301355, 5-29080, 7-134558, 8-234685, and 8-241047; Japanese Patent No. 2784615, U.S. Pat. Nos. 5,828,429 and 6,023,308 are applicable.

<Applications>

Devices fabricated in accordance with embodiments of the inventions described herein may be incorporated into a wide variety of consumer products, including but not limited to flat panel displays, computer monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign.

<Organic Layer>

An organic layer suitable for use in an organic electroluminescence device of the present invention may comprise a plurality of layers, including, for example, light emitting layer, host material, electric charge transporting layer, hole injection layer, and hole transporting layer. Blocking layers may also be included e.g. hole (and or exciton) blocking layers (HBL) or electron (and or exciton) blocking layers (EBL). In some embodiments of an organic electroluminescence device of the present invention, each organic layer may be formed by a dry-type film formation method such as a deposition method or a sputtering method, or a solution coating process such as a transfer method, a printing method, a spin coating method, or a bar coating method. In some embodiments of an organic electroluminescence device of the present invention, at least one layer of the organic layer is preferably formed by a solution coating process.

A. Light Emitting Layer

Light Emitting Material:

A light emitting material in accordance with the present invention preferably includes at least one metal complex having the structure of Formula 1, Formula 2, or Formula 3. Some embodiments of an organic electroluminescence device of the present invention comprises the light emitting material in an amount of about 0.1% by mass to about 50% by mass with respect to the total mass of the compound constituting the light emitting layer. In some embodiments, an organic electroluminescence device of the present invention comprises the light emitting material in an amount of about 1% by mass to about 50% by mass with respect to the total mass of the compound constituting the light emitting layer. In some embodiments, an organic electroluminescence device of the present invention comprises the light emitting material in an amount of about 2% by mass to about 40% by mass with respect to the total mass of the compound constituting the light emitting layer. In some embodiments, a total amount of the light-emitting materials in the light-emitting layer is preferably from about 0.1% by weight to about 30% by weight with respect to the entire amount of compounds contained in the light-emitting layer. In some embodiments, a total amount of the light-emitting materials in the light-emitting layer is preferably from about 1% by weight to about 20% by weight in view of durability and external quantum efficiency. In some embodiments, a total amount of the host materials in the light-emitting layer is preferably from about 70% by weight to about 99.9% by weight. In some embodiments, a total amount of the host materials in the light-emitting layer is preferably from about 80% by weight to 99% by weight in view of durability and external quantum efficiency. In some embodiments, graded light emitting layers or graded interfaces within the light emitting layer may be used. Grading may be formed, for example, by mixing two or more distinct materials in a fashion that an abrupt change from one layer to another is not formed. Graded light emitting layers and or interfaces have been shown to improve device lifetime and this device architecture may be beneficial to improving PHOLED lifetime and general performance. In this instance the the light emitting material may be present in an amount of about 0% by mass to about 100% by mass at any given position within the light emitting layer.

In some embodiments, a light-emitting layer in the present invention may include the light-emitting materials and a host material contained in the light-emitting layer as a combination of a fluorescent light-emitting material which emits light (fluorescence) through a singlet exciton and a host material, or a combination of a phosphorescent light-emitting material which emits light (phosphorescence) through a triplet exciton and a host material. In some embodiments, a light-emitting layer in the present invention may include the light-emitting materials and a host material contained in the light-emitting layer as a combination of a phosphorescent light-emitting material and a host material.

In some embodiments, the first compound can be an emissive dopant. In some embodiments, the compound can produce emissions via phosphorescence, fluorescence, thermally activated delayed fluorescence, i.e., TADF (also referred to as E-type delayed fluorescence), triplet-triplet annihilation, or combinations of these processes.

Emitters should be capable of being sublimed from a heat source under high vacuum conditions. The sublimation temperature of the emitter should be less than about 375 .degree. C. when the distance from the heated source to the OLED substrate exceeds about 50 cm and the film thickness is formed at less than about 0.3 nm/s. In a further embodiment the sublimation temperature of the emitter should be less than about 300 .degree. C. In a further embodiment the sublimation temperature of the emitter should be less than about 280 .degree. C. In a further embodiment the sublimation temperature of the emitter should be less than about 260 .degree. C. Decomposition of the source material during sublimation is undesirable. Decomposed source material typically forms residue, which cannot be sublimed below about 350 .degree. C. The residue may consist of fragments of the original molecule or impurities such as halides and other materials used in the synthesis of the source material.

In order or tune the deposition temperature to the desired temperature range a number of strategies can be used. For example, use of heteroleptic emitters where the 'non-emitting' ligands can be designed to have a low molecular weight in order to reduce the total molecular weight of the emitting molecule. Certain appending groups may also be added that are designed to reduce the deposition temperature e.g. —F, —$CF_3$ etc.

In yet a further embodiment, devices are provided that may be fabricated by sublimation of the emissive dopant. In such cases, in order to achieve long device lifetimes, it is important that the dopant sublime cleanly. Therefore, the dopant may be designed to have sufficient stability towards sublimation as to give an HPLC assay of at least about 98% and leave a residue corresponding to less than about 5 wt % of the original charge in the sublimation crucible. Less than 5 wt % remains after the original charge is fully discharged, i.e., where there is no more appreciable deposition form the crucible when the deposition apparatus is operated under normal conditions. This criteria does not require that the crucible is fully discharged when it is used to make devices. Rather, the criteria is that the source material has sufficient stability under normal deposition conditions, that, if the crucible is fully discharged the residue is less than about 5 wt % of the original charge.

Additionally, the source material used to fabricate an OLED may have a purity that is greater than about 99.5% as determined from high pressure liquid chromatography. This level of purity may be accomplished by performing at least two re-crystallizations and at least two sublimation purifications of the source material. Additionally, the concentration of halide and metal impurities should be less than about 100 ppm. Impurities may have many adverse effects on device operational lifetime. Halide, ligand or metal impurities may affect the conductivity of the organic layers and this could create unfavorable charge balance characteristics. The impurities may be chemically reactive and may destroy emissive molecules to create non-emissive species, or the impurities may trap charge and act as quenching sites that simultaneously contribute to the increase in the operating voltage of devices.

B. Host Material

A suitable host material for use in the present invention, may be a hole transporting host material (sometimes referred to as a hole transporting host), and/or an electron transporting host material (sometimes referred to as an electron transporting host).

The organic layer can also include a host. In some embodiments, two or more hosts are preferred. In some embodiments, the hosts used maybe a) bipolar, b) electron transporting, c) hole transporting or d) wide band gap materials that play little role in charge transport. In some embodiments, the host can include a metal complex. The host can be a triphenylene containing benzo-fused thiophene or benzo-fused furan. Any substituent in the host can be an unfused substituent independently selected from the group consisting of $C_nH_{2n+1}$, $OC_nH_{2n+1}$, $OAr_1$, $N(C_nH_{2n+1})_2$, $N(Ar_1)(Ar_2)$, CH=CH—$C_nH_{2n+1}$, C≡C—$C_nH_{2n+1}$, $Ar_1$, $Ar_1$—$Ar_2$, and $C_nH_{2n}$—$Ar_1$, or no substitution. In the preceding substituents n can range from 1 to 10; and $Ar_1$ and $Ar_2$ can be independently selected from the group consisting of benzene, biphenyl, naphthalene, triphenylene, carbazole, and heteroaromatic analogs thereof. In some embodiment, the host can also be an inorganic compound. For example a Zn containing inorganic material, e.g. ZnS.

The host can be a compound comprising at least one chemical group selected from the group consisting of triphenylene, carbazole, dibenzothiophene, dibenzofuran, dibenzoselenophene, azatriphenylene, azacarbazole, aza-dibenzothiophene, aza-dibenzofuran, and aza-dibenzoselenophene. The host can include a metal complex. The host can be a specific compound selected from the group consisting of:

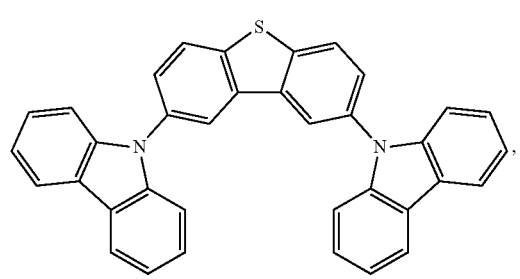
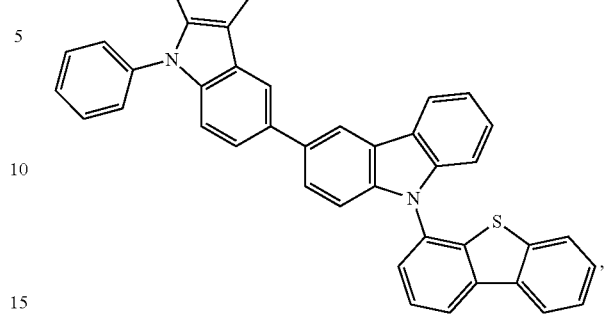
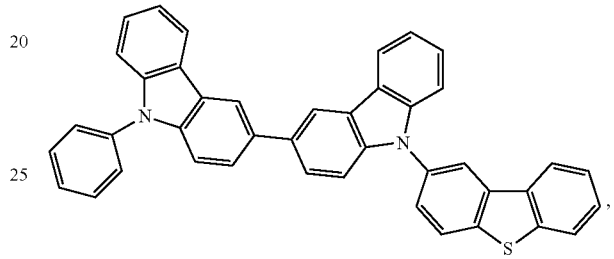
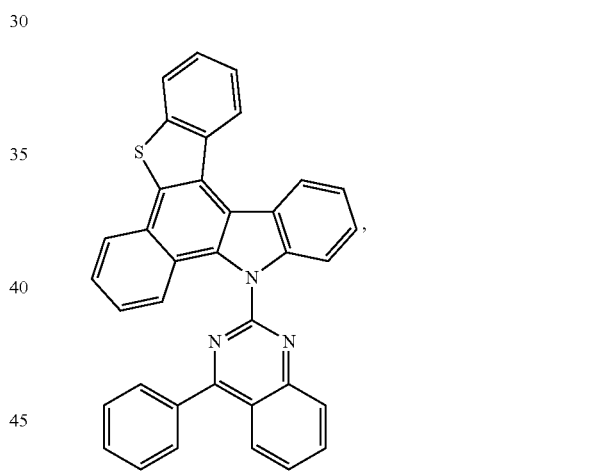
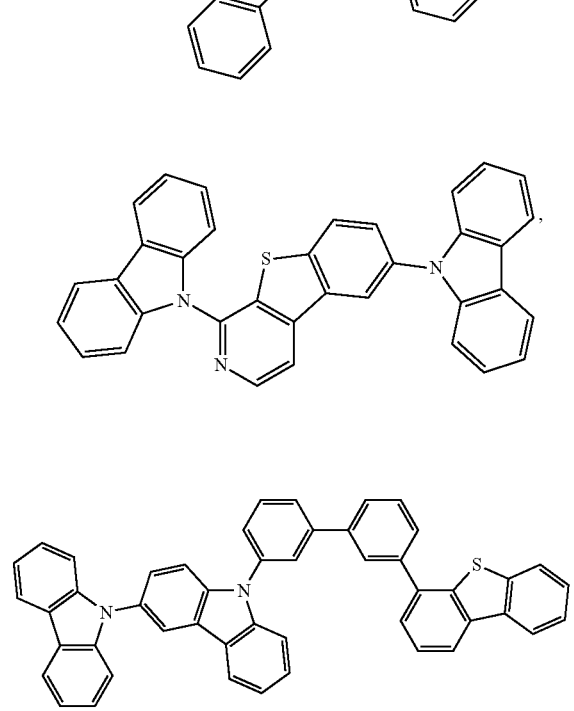
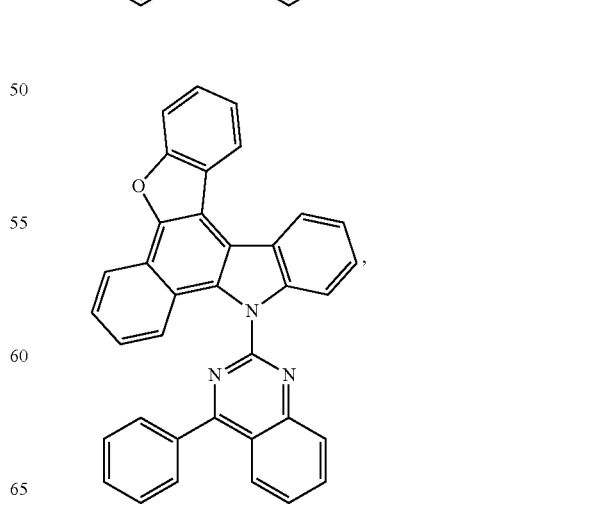

-continued
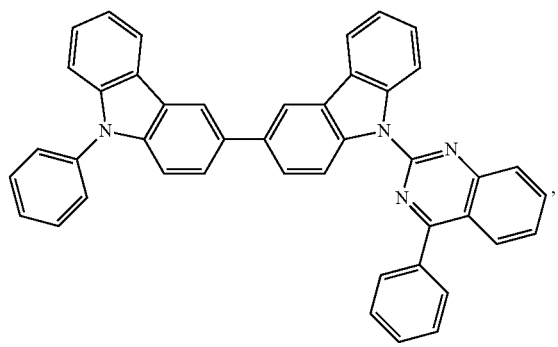
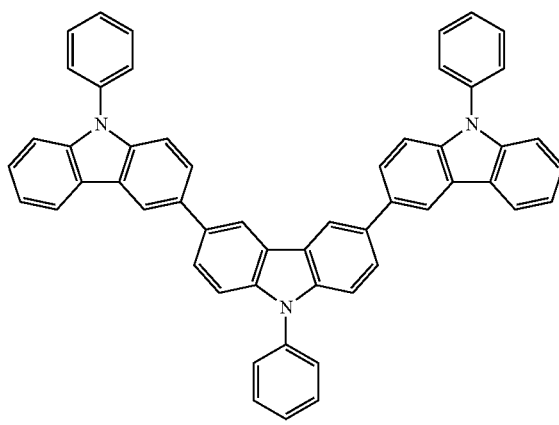
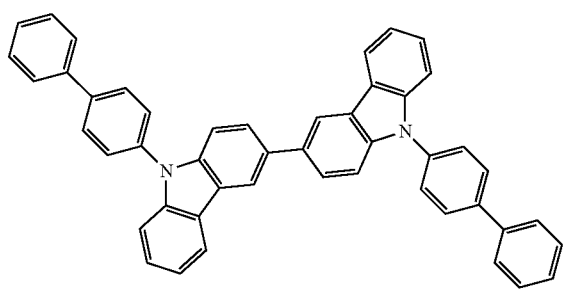
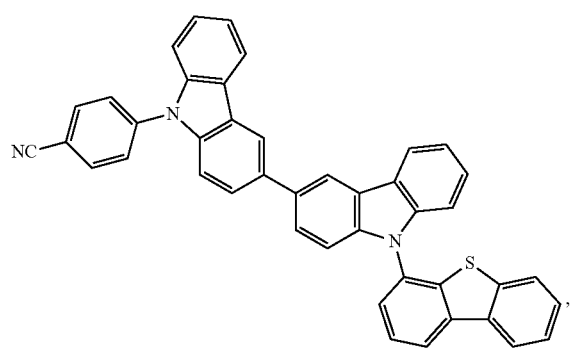
-continued
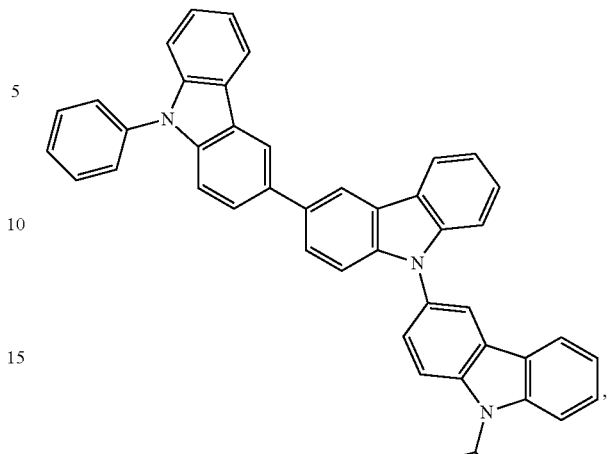
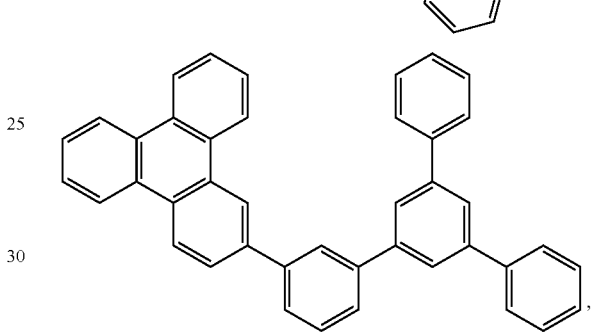
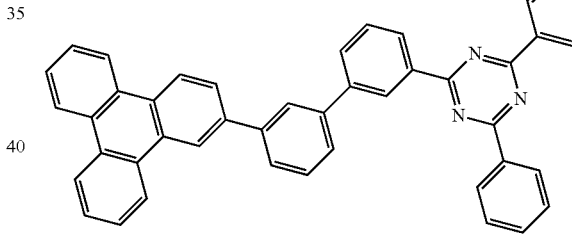
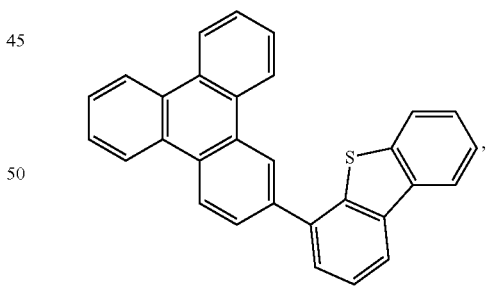
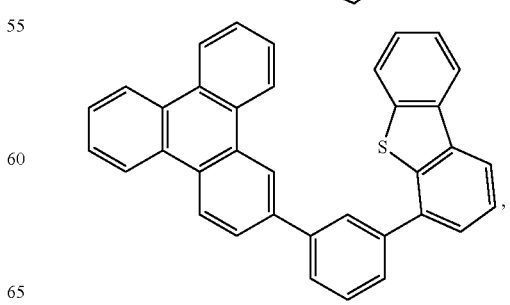

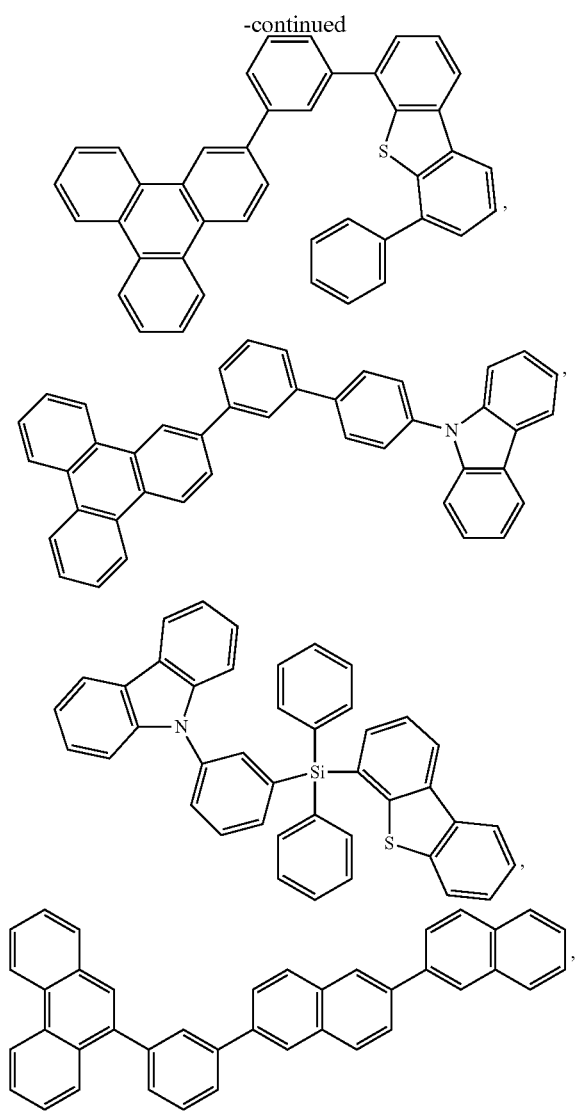

and combinations thereof.

Hole Transporting Host Material

Specific examples of the hole transporting host materials include, but are not limited to pyrrole, carbazole, azacarbazole, pyrazole, indole, azaindole, imidazole, polyarylalkane, pyrazoline, pyrazolone, phenylenediamine, arylamine, amino-substituted chalcone, styrylanthracene, fluorenone, hydrazone, stilbene, silazane, aromatic tertiary amine compounds, styrylamine compounds, aromatic dimethylidine compounds, porphyrin compounds, polysilane compounds, poly(N-vinylcarbazole), aniline copolymers, electric conductive high-molecular oligomers such as thiophene oligomers, polythiophenes and the like, organic silanes, carbon films, derivatives thereof, and the like. Some preferred host materials include carbazole derivatives, indole derivatives, imidazole derivatives, aromatic tertiary amine compounds, and thiophene derivatives.

Specific examples of the electron transporting host materials include, but are not limited to pyridine, pyrimidine, triazine, imidazole, pyrazole, triazole, oxazole, oxadiazole, fluorenone, anthraquinonedimethane, anthrone, diphenylquinone, thiopyrandioxide, carbodiimide, fluorenylidenemethane, distyrylpyrazine, fluorine-substituted aromatic compounds, aromacyclic tetracarboxylic anhydrides of naphthalene, perylene or the like, phthalocyanine, derivatives thereof, including a variety of metal complexes represented by metal complexes of 8-quinolinol derivatives, metal phthalocyanine, and metal complexes having benzoxazole or benzothiazole as the ligand.

Preferable electron transporting hosts are metal complexes, azole derivatives (benzimidazole derivatives, imidazopyridine derivatives and the like), and azine derivatives (pyridine derivatives, pyrimidine derivatives, triazine derivatives and the like).

C. Film Thickness

In some embodiments, the film thickness of the light-emitting layer is preferably from about 10 nm to about 500 nm. In some embodiments, the film thickness of the light-emitting layer is preferably from about 20 nm to about 100 nm depending, for example, on desired brightness uniformity, driving voltage and brightness. In some embodiments, the light-emitting layer is configured to have a thickness that optimizes passage of charges from the light-emitting layer to adjacent layers without lowering light-emission efficiency. In some embodiments, the light-emitting layer is configured to have a thickness that maintains minimum driving voltage maximum light-emission efficiency.

D. Layer Configuration

The light-emitting layer may be composed of a single layer or two or more layers, and the respective layers may cause light emission in different light-emitting colors. Also, in the case where the light-emitting layer has a laminate structure, though the film thickness of each of the layers configuring the laminate structure is not particularly limited, it is preferable that a total film thickness of each of the light-emitting layers falls within the foregoing range. In some embodiments, graded layers or graded interfaces within the layers may be used.

E. Hole Injection Layer and Hole Transport Layer

The hole injection layer and hole transport layer are layers functioning to receive holes from an anode or from an anode side and to transport the holes to the emitting layer. Materials to be introduced into a hole injection layer or a hole transport layer is not particularly limited, but either of a low molecular compound or a high molecular compound may be used.

Specific examples of the material contained in the hole injection layer and the hole transport layer include, but are not limited to, pyrrole derivatives, carbazole derivatives, azacarbazole derivatives, indole derivatives, azaindole derivatives, imidazole derivatives, polyarylalkane derivatives, pyrazoline derivatives, pyrazolone derivatives, phenylenediamine derivatives, arylamine derivatives, amino-substituted chalcone derivatives, styrylanthracene derivatives, fluorenone derivatives, hydrazone derivatives, stilbene derivatives, silazane derivatives, aromatic tertiary amine compounds, styrylamine compounds, aromatic dimethylidine compounds, phthalocyanine compounds, porphyrin compounds, organosilane derivatives, carbon, and the like.

An electron-accepting dopant may be introduced into the hole injection layer or the hole transport layer in the organic EL element of the present invention. As the electron-accepting dopant to be introduced into the hole injection layer or the hole transport layer, either of an inorganic compound or an organic compound may be used as long as the compound has electron accepting property and a function for oxidizing an organic compound.

Specifically, the inorganic compound includes metal halides such as ferric chloride, aluminum chloride, gallium chloride, indium chloride, antimony pentachloride and the like, and metal oxides such as vanadium pentaoxide, molybdenum trioxide and the like.

In case of employing the organic compounds, compounds having a substituent such as a nitro group, a halogen, a cyano group, a trifluoromethyl group or the like; quinone compounds; acid anhydride compounds; fullerenes; and the like may be preferably applied.

Specific examples hole injection and hole transport materials include compounds described in patent documents such as JP-A Nos. 6-212153, 11-111463, 11-251067, 2000-196140, 2000-286054, 2000-315580, 2001-102175, 2001-160493, 2002-252085, 2002-56985, 2003-157981, 2003-217862, 2003-229278, 2004-342614, 2005-72012, 2005-166637, 2005-209643 and the like.

Specific examples of hole injection and hole transport materials include the organic compounds: hexacyanobutadiene, hexacyanobenzene, tetracyanoethylene, tetracyanoquinodimethane, tetrafluorotetracyanoquinodimethane, p-fluoranil, p-chloranil, p-bromanil, p-benzoquinone, 2,6-dichlorobenzoquinone, 2,5-dichlorobenzoquinone, 1,2,4,5-tetracyanobenzene, 1,4-dicyanotetrafluorobenzene, 2,3-dichloro-5,6-dicyanobenzoquinone, p-dinitrobenzene, m-dinitrobenzene, o-dinitrobenzene, 1,4-naphthoquinone, 2,3-dichloronaphthoquinone, 1,3-dinitronaphthalene, 1,5-dinitronaphthalene, 9,10-anthraquinone, 1,3,6,8-tetranitrocarbazole, 2,4,7-trinitro-9-fluorenone, 2,3,5,6-tetracyanopyridine and fullerene C60. Among these, hexacyanobutadiene, hexacyanobenzene, tetracyanoethylene, tetracyanoquinodimethane, tetrafluorotetracyanoquinodimethane, p-fluoranil, p-chloranil, p-bromanil, 2,6-dichlorobenzoquinone, 2,5-dichlorobenzoquinone, 2,3-dichloronaphthoquinone, 1,2,4,5-tetracyanobenzene, 2,3-dichloro-5,6-dicyanobenzoquinone and 2,3,5,6-tetracyanopyridine are more preferable, and tetrafluorotetracyanoquinodimethane.

As one or more electron-accepting dopants may be introduced into the hole injection layer or the hole transport layer in the organic EL element of the present invention, these electron-accepting dopants may be used alone or in combinations of two or more. Although precise amount of these electron-accepting dopants used will depend on the type of material, about 0.01% by weight to about 50% by weight of the total weight of the hole transport layer or the hole injection layer is preferred. In some embodiments, the amount of these electron-accepting dopants range from about 0.05% by weight to about 20% by weight of the total weight of the hole transport layer or the hole injection layer. In some embodiments, the amount of these electron-accepting dopants range from about 0.1% by weight to about 10% by weight of the total weight of the hole transport layer or the hole injection layer.

In some embodiments, a thickness of the hole injection layer and a thickness of the hole transport layer are each preferably about 500 nm or less in view of decreasing driving voltage or optimizing for optical outcoupling. In some embodiments, the thickness of the hole transport layer is preferably from about 1 nm to about 500 nm. In some embodiments, the thickness of the hole transport layer is preferably from about 5 nm to about 50 nm. In some embodiments, the thickness of the hole transport layer is preferably from about 10 nm to about 40 nm. In some embodiments, the thickness of the hole injection layer is preferably from about 0.1 nm to about 500 nm. In some embodiments, the thickness of the hole injection layer is preferably from about 0.5 nm to about 300 nm. In some embodiments, the thickness of the hole injection layer is preferably from about 1 nm to about 200 nm.

The hole injection layer and the hole transport layer may be composed of a monolayer structure comprising one or two or more of the above-mentioned materials, or a multilayer structure composed of plural layers of a homogeneous composition or a heterogeneous composition.

F. Electron Injection Layer and Electron Transport Layer

The electron injection layer and the electron transport layer are layers having functions for receiving electrons from a cathode or a cathode side, and transporting electrons to the light emitting layer. An electron injection material or an electron transporting material used for these layers may be a low molecular compound or a high molecular compound. Specific examples of the materials suitable for use in electron injection and electron transport layers include, but are not limited to, pyridine derivatives, quinoline derivatives, pyrimidine derivatives, pyrazine derivatives, phthalazine derivatives, phenanthroline derivatives, triazine derivatives, triazole derivatives, oxazole derivatives, oxadiazole derivatives, imidazole derivatives, fluorenone derivatives, anthraquinodimethane derivatives, anthrone derivatives, diphenylquinone derivatives, thiopyrandioxide derivatives, carbodiimide derivatives, fluorenylidenemethane derivatives, distyrylpyrazine derivatives, aromacyclic tetracarboxylic anhydrides of perylene, naphthalene or the like, phthalocyanine derivatives, metal complexes represented by metal complexes of 8-quinolinol derivatives, metal phthalocyanine, and metal complexes containing benzoxazole, or benzothiazole as the ligand, organic silane derivatives exemplified by silole, and the like.

The electron injection layer or the electron transport layer may contain an electron donating dopant. Suitable electron donating dopant for use in the electron injection layer or the electron transport layer, include any suitable material that may be used as long as it has an electron-donating property and a property for reducing an organic compound. Specific examples of electron donating dopants include an alkaline metal such as Li, an alkaline earth metal such as Mg, a transition metal including a rare-earth metal, and a reducing organic compound. Other examples of metal donating dopants include, metals having a work function of 4.2 V or less, for example, Li, Na, K, Be, Mg, Ca, Sr, Ba, Y, Cs, La, Sm, Gd, Yb, and the like. Specific examples of the reducing organic compounds include nitrogen-containing compounds, sulfur-containing compounds, phosphorus-containing compounds, and the like.

The electron donating dopants may be used alone or in combinations of two or more. In some embodiments, an electron donating dopant is contained in the electron injection layer or the electron transport layer in an amount ranging from about 0.1% by weight to about 99% by weight of the total weight of the electron transport layer material or the electron injecting layer mater. In some embodiments, an electron donating dopant is contained in the electron injection layer or the electron transport layer in an amount ranging from about 1.0% by weight to about 80% by weight of the total weight of the electron transport layer material or the electron injecting layer material. In some embodiments, an electron donating dopant is contained in the electron injection layer or the electron transport layer in an amount ranging from about 2.0% by weight to about 70% by weight of the total weight of the electron transport layer material or the electron injecting layer material.

A thickness of the electron injection layer and a thickness of the electron transport layer are each preferably 500 nm or less in view of decrease in driving voltage. The thickness of the electron transport layer is preferably from 1 nm to 500 nm, more preferably from 5 nm to 200 nm, and even more preferably from 10 nm to 100 nm. A thickness of the electron injection layer is preferably from 0.1 nm to 200 nm, more preferably from 0.2 nm to 100 nm, and even more preferably from 0.5 nm to 50 nm.

The electron injection layer and the electron-transport may be composed of a monolayer structure comprising one or two or more of the above-mentioned materials, or a multilayer structure composed of plural layers of a homogeneous composition or a heterogeneous composition.

According to an embodiment, an OLED comprising: an anode; a cathode; and an emission layer, disposed between the anode and the cathode, comprising a first emitting compound; wherein the first emitting compound is capable of functioning as a blue phosphorescent emitter in the OLED at room temperature; wherein the first emitting compound has PLQY of less than 90% at room temperature; wherein the OLED has an external quantum efficiency of between 8% and 20% at 1 mA/cm².

In some embodiments of the OLED, the first emitting compound is capable of emitting light from a triplet excited state to a ground singlet state at room temperature. In some embodiments of the OLED, the first emitting compound is a metal coordination complex having a metal-carbon bond.

In some embodiments of the OLED, the metal in the metal coordination complex is selected from the group consisting of Ir, Rh, Re, Ru, Os, Pt, Au, and Cu. In some embodiments, the metal is Ir. In some embodiments, the metal is Pt.

In some embodiments of the OLED, the first emitting compound has the formula of $M(L^1)_x(L^2)_y(L^3)_z$; wherein $L^1$, $L^2$ and $L^3$ can be the same or different; wherein x is 1, 2, or 3; wherein y is 0, 1, or 2; wherein z is 0, 1, or 2; wherein x+y+z is the oxidation state of the metal M; wherein $L^1$, $L^2$ and $L^3$ are each independently selected from the group consisting of;

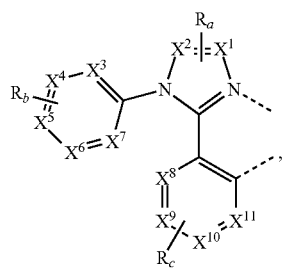

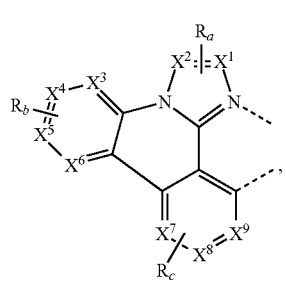

-continued

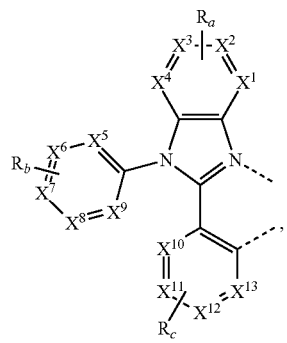

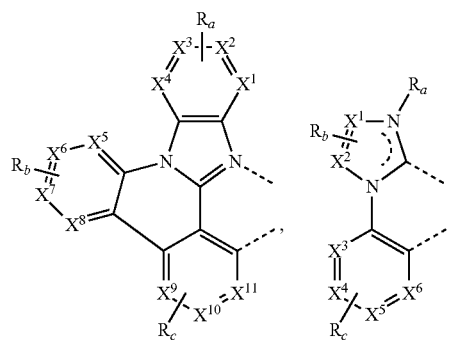

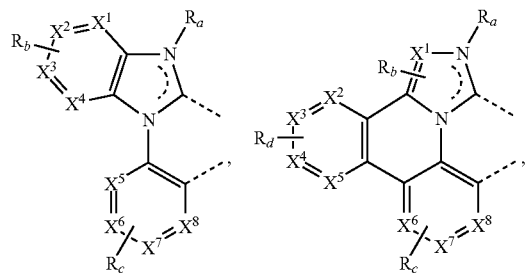

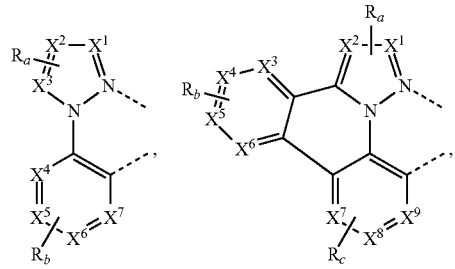

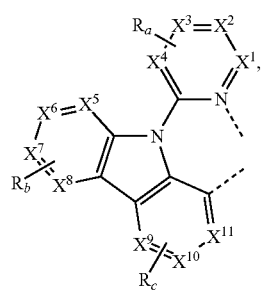

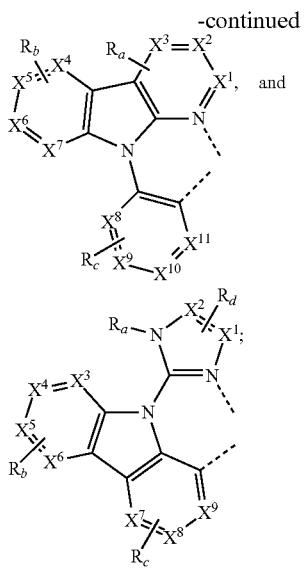

wherein each $X^1$ to $X^{13}$ are independently selected from the group consisting of carbon and nitrogen; wherein X is selected from the group consisting of BR', NR', PR', O, S, Se, C=O, S=O, $SO_2$, CR'R", SiR'R", and GeR'R"; wherein R' and R" are optionally fused or joined to form a ring; wherein each $R_a$, $R_b$, $R_c$, and $R_d$ may represent from mono substitution to the possible maximum number of substitution, or no substitution; wherein R', R", $R_a$, $R_b$, $R_c$, and $R_d$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein any two adjacent substitutents of $R_a$, $R_b$, $R_c$, and $R_d$ are optionally fused or joined to form a ring or form a multidentate ligand.

In some embodiments of the OLED, the OLED has a performance lifetime of at least 30 hours to 80% of the initial luminance at room temperature under a constant driving current of 20 $mA/cm^2$.

In some embodiments of the OLED, the OLED has a performance lifetime of at least 100 hours to 80% of the initial luminance at room temperature under a constant driving current of 20 $mA/cm^2$.

In some embodiments of the OLED, the OLED has a performance lifetime of at least 150 hours to 80% of the initial luminance at room temperature under a constant driving current of 20 $mA/cm^2$.

In some embodiments of the OLED, the OLED has a performance lifetime of at least 200 hours to 80% of the initial luminance at room temperature under a constant driving current of 20 $mA/cm^2$.

In some embodiments of the OLED, the OLED has a performance lifetime of at least 300 hours to 80% of the initial luminance at room temperature under a constant driving current of 20 $mA/cm^2$.

In some embodiments of the OLED, the OLED has a performance lifetime of at least 500 hours to 80% of the initial luminance at room temperature under a constant driving current of 20 $mA/cm^2$.

In some embodiments of the OLED, the OLED has a performance lifetime of at least 1,000 hours to 80% of the initial luminance at room temperature under a constant driving current of 20 $mA/cm^2$.

In some embodiments of the OLED, the OLED has a performance lifetime of at least 2,000 hours to 80% of the initial luminance at room temperature under a constant driving current of 20 $mA/cm^2$.

In some embodiments of the OLED, the first emitting compound has a first triplet energy less than 500 nanometers. In some embodiments of the OLED, the first emitting compound has a first triplet energy less than 480 nanometers. In some embodiments of the OLED, the first emitting compound has a first triplet energy less than 470 nanometers. In some embodiments of the OLED, the first emitting compound has a first triplet energy less than 460 nanometers. In some embodiments of the OLED, the first emitting compound has a first triplet energy less than 450 nanometers.

In some embodiments of the OLED, the first emitting compound emits light having a CIE x-coordinate less than 0.25 and a CIE y-coordinate less than 0.4. In some embodiments of the OLED, the first emitting compound emits light having a CIE x-coordinate less than 0.25 and a CIE y-coordinate less than 0.3. In some embodiments of the OLED, the first emitting compound emits light having a CIE x-coordinate less than 0.25 and a CIE y-coordinate less than 0.2. In some embodiments, the first emitting compound emits light having a CIE x-coordinate less than 0.2 and a CIE y-coordinate less than 0.15.

In some embodiments of the OLED, the first emitting compound has less than 2 microsecond of the fastest component of its photoluminescence transient that fits to a multiple exponential function at room temperature under an inert atmosphere. In some embodiments of the OLED, the first emitting compound has less than 1 microsecond of the fastest component of its photoluminescence transient that fits to a multiple exponential function at room temperature under an inert atmosphere. In some embodiments of the OLED, the first emitting compound has less than 0.5 microsecond of the fastest component of its photoluminescence transient that fits to a multiple exponential function at room temperature under an inert atmosphere.

In some embodiments of the OLED, the first emitting compound has PLQY of less than 80% at room temperature. In some embodiments of the OLED, the first emitting compound has PLQY of less than 70% at room temperature. In some embodiments of the OLED, the first emitting compound has PLQY of less than 60% at room temperature. In some embodiments of the OLED, the first emitting compound has PLQY of less than 50% at room temperature. In some embodiments of the OLED, the first emitting compound has PLQY of less than 40% at room temperature.

In some embodiments of the OLED, the OLED has an external quantum efficiency of between 8% and 18% at 1 $mA/cm^2$. In some embodiments of the OLED, the OLED has an external quantum efficiency of between 8% and 15% at 1 $mA/cm^2$. In some embodiments of the OLED, the OLED has an external quantum efficiency of between 8% and 13% at 1 $mA/cm^2$. In some embodiments of the OLED, the OLED has an external quantum efficiency of between 8% and 11% at 1 $mA/cm^2$. In some embodiments of the OLED, the OLED has an external quantum efficiency of between 8% and 10% at 1 $mA/cm^2$.

In some embodiments of the OLED, the M is selected from the group consisting of Ir, Rh, Re, Ru, Os, Pt, Au, and Cu. In some embodiments, the M is Ir. In some embodiments, the M is Pt.

In some embodiments of the OLED wherein the first emitting compound has the formula of $M(L^1)_x(L^2)_y(L^3)_z$ defined above; the first emitting compound has the formula of $Ir(L^1)_2(L^2)$. In some embodiments of the OLED, the first emitting compound has the formula of $Ir(L^1)_3$. In some embodiments of the OLED, the first emitting compound has the formula of $Ir(L^1)(L^2)(L^3)$. In these formulas for the first emitting compound, $L^1$, $L^2$ and $L^3$ are each independently selected from the group consisting of:

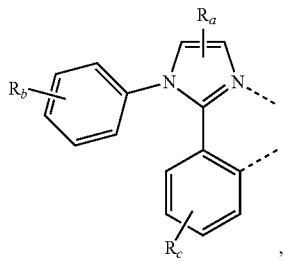

,

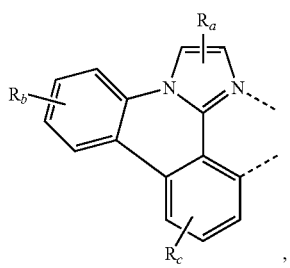

,

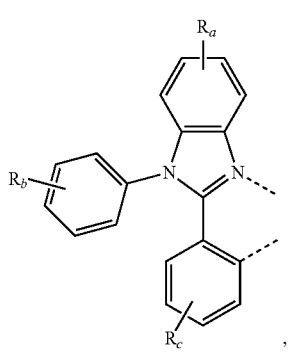

,

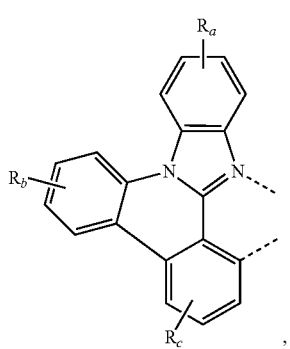

,

-continued

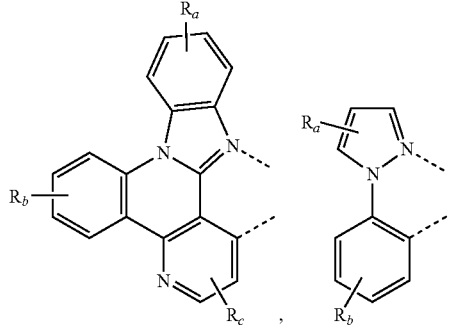

,

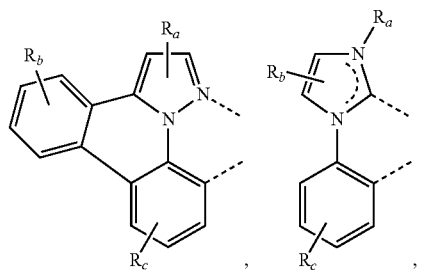

,

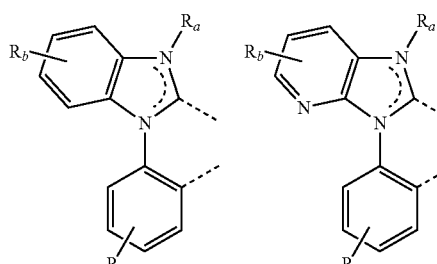

,

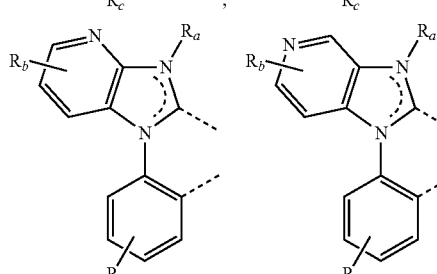

,

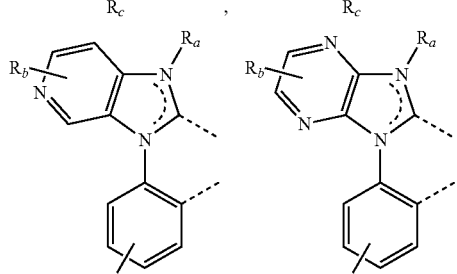

,

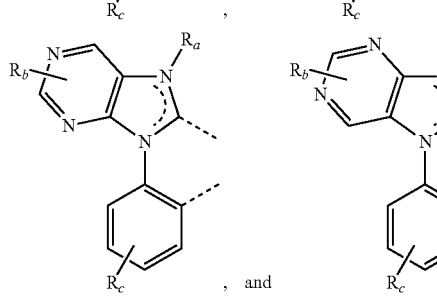

, and .

In some embodiments of the OLED, the first emitting compound has the formula of $Pt(L^1)_2$ or $Pt(L^1)(L^2)$.

In some embodiments of the OLED wherein the first emitting compound has the formula of $M(L^1)_x(L^2)_y(L^3)_z$ defined above, at least one of $L^1$, $L^2$ and $L^3$ is:

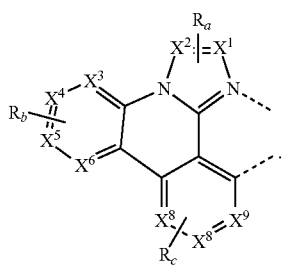

In some embodiments of the OLED wherein the first emitting compound has the formula of $M(L^1)_x(L^2)_y(L^3)_z$ defined above, at least one of $L^1$, $L^2$ and $L^3$ is:

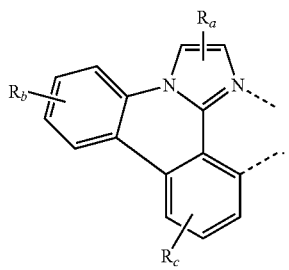

In some embodiments of the OLED wherein the first emitting compound has the formula of $M(L^1)_x(L^2)_y(L^3)_z$ defined above, the first emitting compound has a structure $(L_A)_nML_m$ according to Formula 1:

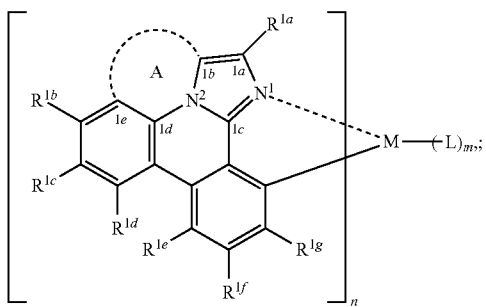

Formula 1 wherein M is a metal having an atomic weight greater than 40, n has a value of at least 1 and m+n is the maxiumn number of ligands that may be attached to the metal;
wherein A is a linking group having two to three linking atoms, wherein the linking atoms are each independently selected from the group consisting of C, Si, O, S, N, B or combinations thereof;
wherein $R^{1a}$ to $R^{1g}$ are each independently selected from the group consisting of hydrogen, deuterium, alkyl, cycloalkyl, heteroalkyl, alkoxy, aryloxy, amino, silyl, alkenyl, cycloalkenyl, heteroalkenyl, alkynyl, aralkyl, CN, $CF_3$, $CO_2R$, $C(O)R$, $C(O)NR_2$, $NR_2$, $NO_2$, OR, SR, $SO_2$, SOR, $SO_3R$, halo, aryl, heteroaryl, a heterocyclic group, and combinations thereof;
wherein each R is independently selected from the group consisting of hydrogen, deuterium, halo, alkyl, cycloalkyl, heteroalkyl, alkoxy, aryloxy, amino, silyl, alkenyl, cycloalkenyl, heteroalkenyl, alkynyl, aralkyl, aryl, heteroaryl, and combinations thereof;
wherein any one of the ring atoms to which $R^{1b}$ to $R^{1g}$ are attached may be replaced with a nitrogen atom, wherein when the ring atom is replaced with a nitrogen atom the corresponding R group is not present; and wherein L is a substituted or unsubstituted cyclometallated ligand.

In some embodiments of the OLED where the first emitting compound has a structure $(L_A)_nML_m$ according to Formula 1 defined above, the linking atoms in A form at least one single bond between two linking atoms.

In some embodiments of the OLED where the first emitting compound has a structure $(L_A)_nML_m$ according to Formula 1 defined above, the linking group A is independently selected from the group consisting of $-CR^1R^2-CR^3R^4-$, $-CR^1R^2-CR^3R^4-CR^5R^6-$, $-CR^1R^2-NR^3-$, $-CR^1=CR^2-CR^3R^4-$, $-O-SiR^1R^2-$, $-CR^1R^2-S-$, $-CR^1R^2-O-$, and $-C-SiR^1R^2-$, wherein each $R^1$ to $R^6$ can be same or different, and are independently selected from the group consisting of hydrogen, deuterium, alkyl, cycloalkyl, aryl, heteroaryl, and combinations thereof; wherein any adjacent $R^1$ to $R^6$ are optionally connected to form a saturated five membered ring or a saturated six membered ring. In some embodiments, at least one adjacent $R^1$ to $R^6$ are connected to form a saturated five membered ring or a saturated six membered ring. In some embodiments, each $R^1$ to $R^6$ are independently selected from the group consisting of alkyl, cycloalkyl, aryl, heteroaryl, partially or fully deuterated variants thereof, and combinations thereof; wherein any adjacent $R^1$ to $R^6$ are optionally connected to form a saturated five membered ring or a saturated six membered ring.

In some embodiments of the OLED where the first emitting compound has a structure $(L_A)_nML_m$ according to Formula 1 defined above, the compound has a triplet excited state and wherein the linking group stabilizes the bond between $N^2$ and $C^{1b}$ from cleavage when the compound is in the triplet excited state.

In some embodiments of the OLED where the first emitting compound has a structure $(L_A)_nML_m$ according to Formula 1 defined above, the linking group is selected from the group consisting of:

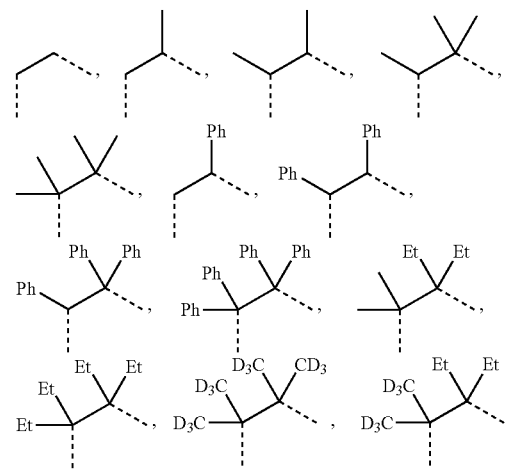

-continued
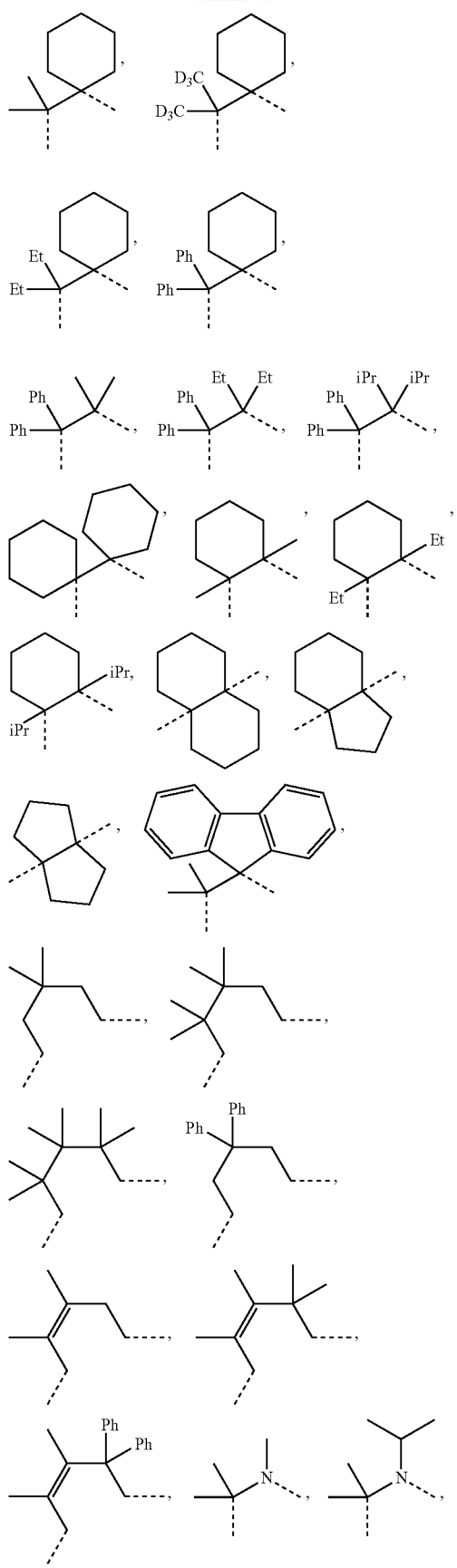
-continued
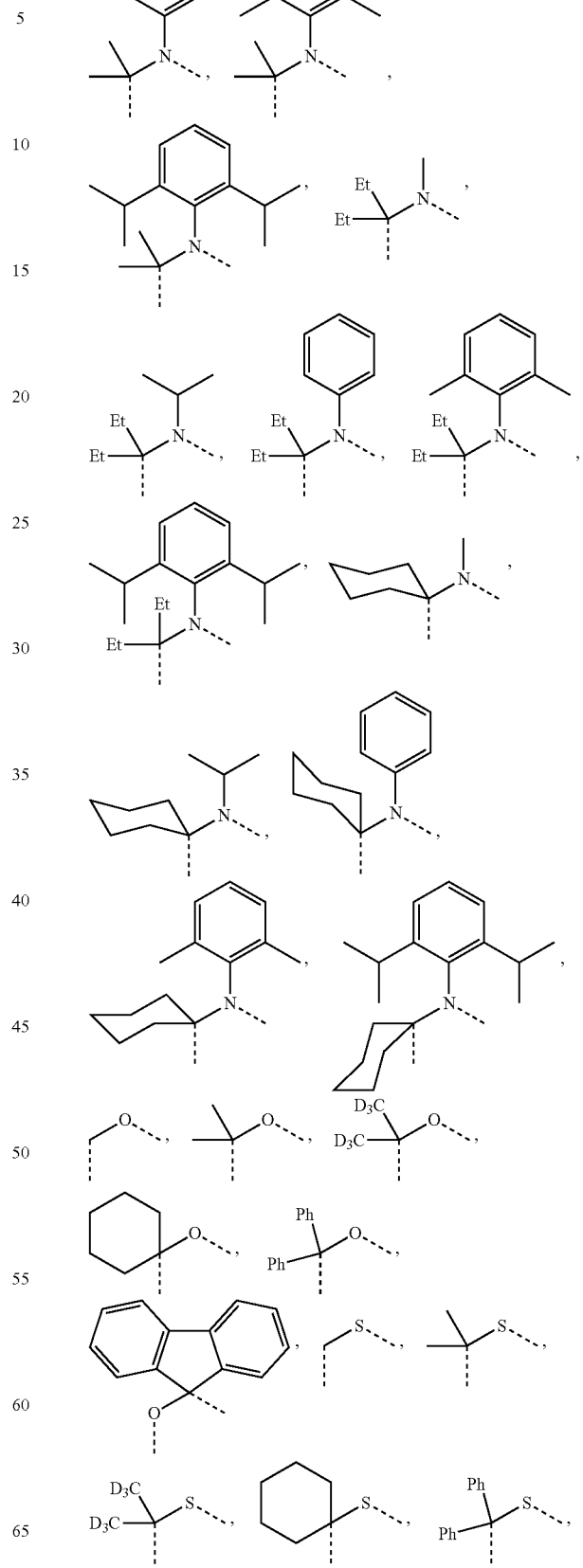

-continued

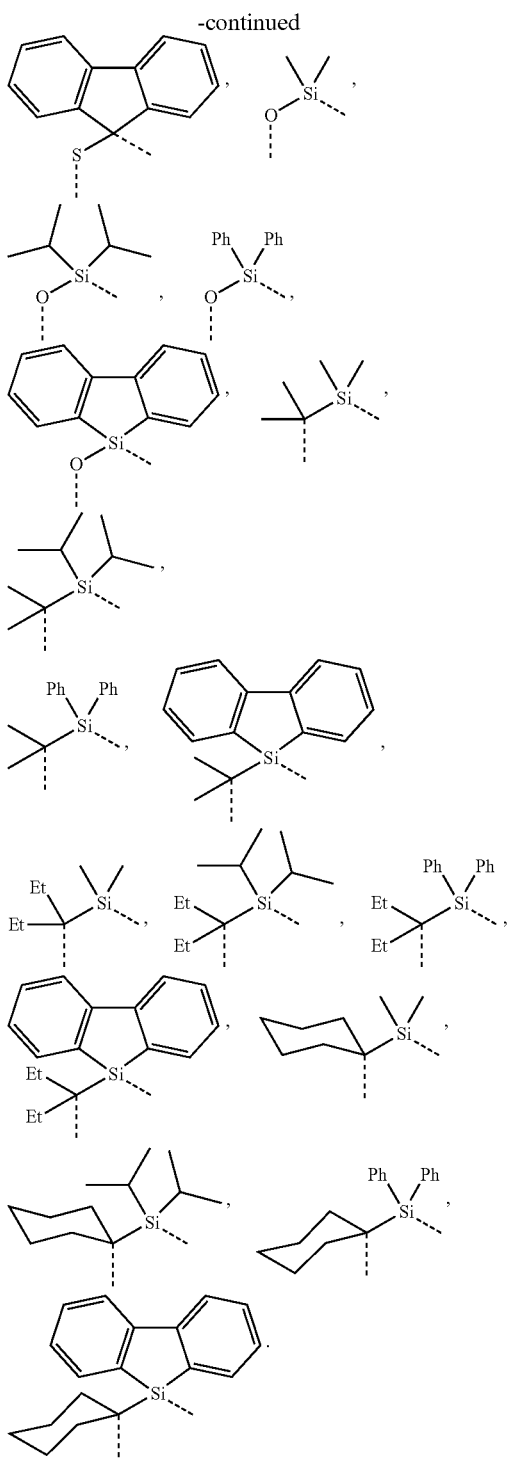

In some embodiments of the OLED where the first emitting compound has a structure $(L_A)_nML_m$ according to Formula 1 defined above, A is a saturated group.

In some embodiments of the OLED where the first emitting compound has a structure $(L_A)_nML_m$ according to Formula 1 defined above, at least one of $R^{1a}$ to $R^{1g}$ is selected from the group consisting of alkyl, cycloalkyl, aryl, heteroaryl, partially or fully deuterated variants thereof, and combinations thereof.

In some embodiments of the OLED where the first emitting compound has a structure $(L_A)_nML_m$ according to Formula 1 defined above, the metal is selected from the group consisting of Re, Ru, Os, Rh, Ir, Pd, Pt, and Au.

In some embodiments of the OLED where the first emitting compound has a structure $(L_A)_nML_m$ according to Formula 1 defined above, the metal is selected from the group consisting of Ir and Pt.

In some embodiments of the OLED where the first emitting compound has a structure $(L_A)_nML_m$ according to Formula 1 defined above, the first emitting compound is $(L_A)_3Ir$, $(L_A)Ir(L)_2$ or $(L_A)_2Ir(L)$.

In some embodiments of the OLED where the first emitting compound has a structure $(L_A)_nML_m$ according to Formula 1 defined above, the first emitting compound has a structure of Formula 2:

Formula 2

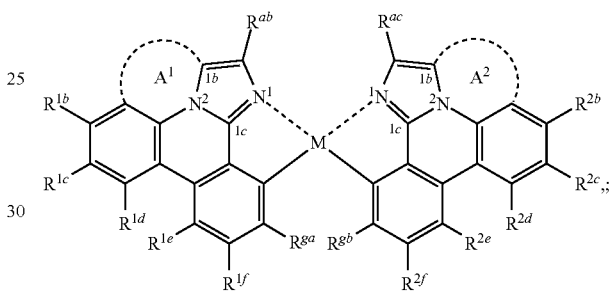

wherein M is Pt;
wherein $A^1$ and $A^2$ are each independently a firstlinking group having two to three linking atoms, wherein the linking atoms are each independently selected from the group consisting of C, Si, O, S, N, B or combinations thereof;
wherein $R^{1b}$ to $R^{1f}$ and $R^{2b}$ to $R^{2f}$ are each independently selected from the group consisting of hydrogen, deuterium, alkyl, cycloalkyl, heteroalkyl, alkoxy, aryloxy, amino, silyl, alkenyl, cycloalkenyl, heteroalkenyl, alkynyl, aralkyl, CN, $CF_3$, $CO_2R$, C(O)R, $C(O)NR_2$, $NR_2$, $NO_2$, OR, SR, $SO_2$, SOR, $SO_3R$, halo, aryl, heteroaryl, a heterocyclic group, and combinations thereof;
wherein any one of the ring atoms to which $R^{1b}$ to $R^{1f}$ and $R^{2b}$ to $R^{2f}$ are attached may be replaced with a nitrogen atom, wherein when the ring atom is replaced with a nitrogen atom the corresponding R group is not present; and
wherein $R^{ab}$ and $R^{ac}$ and/or $R^{ga}$ and $R^{gb}$ may bond to form a second linking group having one to three linking atoms each independently selected from the group consisting of B, N, P, O, S, Se, C, Si, Ge or combinations thereof.

In some embodiments of the OLED where the first emitting compound has a structure $(L_A)_nML_m$ according to Formula 1 defined above, $A^2$ has a same definition but can be same or different entity as $A^1$.

In some embodiments of the OLED where the first emitting compound has a structure $(L_A)_nML_m$ according to Formula 1 defined above, the first emitting compound has Formula 3:

Formula 3

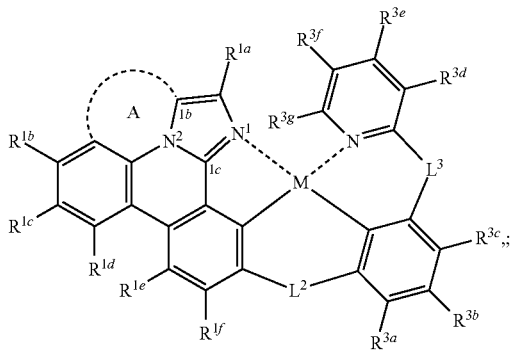

wherein M is Pt;
wherein $L^2$ and $L^3$ are each independently selected from the group consisting of a single bond, BR, NR, PR, O, S, Se, C—O, S—O, $SO_2$, $CR^1R^2$, $SiR^1R^2$, and $GeR^1R^2$;
wherein $R^{3a}$-$R^{3f}$, are each independently selected from the group consisting of hydrogen, deuterium, alkyl, cycloalkyl, heteroalkyl, alkoxy, aryloxy, amino, silyl, alkenyl, cycloalkenyl, heteroalkenyl, alkynyl, aralkyl, CN, $CF_3$, $CO_2R$, C(O)R, $C(O)NR_2$, $NR_2$, $NO_2$, OR, SR, $SO_2$, SOR, $SO_3R$, halo, aryl, heteroaryl, a heterocyclic group, and combinations thereof;
wherein any two adjacent $R^{1f}$, $R^{3a}$, $R^{3c}$, $R^{3d}$, $R^1$ and $R^2$ are optionally joined to form a ring; wherein $L^2$ and $R^{1f}$, $L^2$ and $R^{3a}$, or $L^2$ and both $R^{1f}$ and $R^{3a}$ are optionally joined to form one or more rings; and
wherein $L^3$ and $R^{3c}$, $L^3$ and $R^{3d}$, or $L^3$ and both $R^{3c}$ and $R^{3d}$ are optionally joined to form one or more rings.

According to an aspect of the present disclosure, the OLED disclosed herein is incorporated into a device selected from the group consisting of a consumer product, an electronic component module, and a lighting panel.

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

HIL/HTL:

A hole injecting/transporting material to be used in the present invention is not particularly limited, and any compound may be used as long as the compound is typically used as a hole injecting/transporting material. Examples of the material include, but are not limited to: a phthalocyanine or porphyrin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and silane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compound.

Examples of aromatic amine derivatives used in HIL or HTL include, but are not limited to the following general structures:

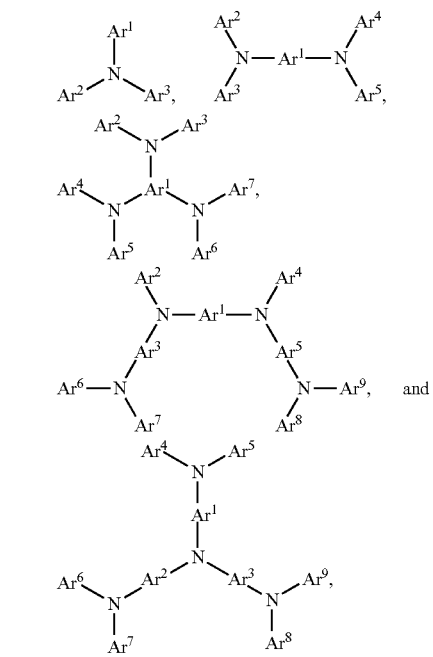

Each of $Ar^1$ to $Ar^9$ is selected from the group consisting of aromatic hydrocarbon cyclic compounds such as benzene, biphenyl, triphenyl, triphenylene, naphthalene, anthracene, phenalene, phenanthrene, fluorene, pyrene, chrysene, perylene, and azulene; the group consisting of aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and the group consisting of 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each Ar is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, Ar¹ to Ar⁹ is independently selected from the group consisting of:

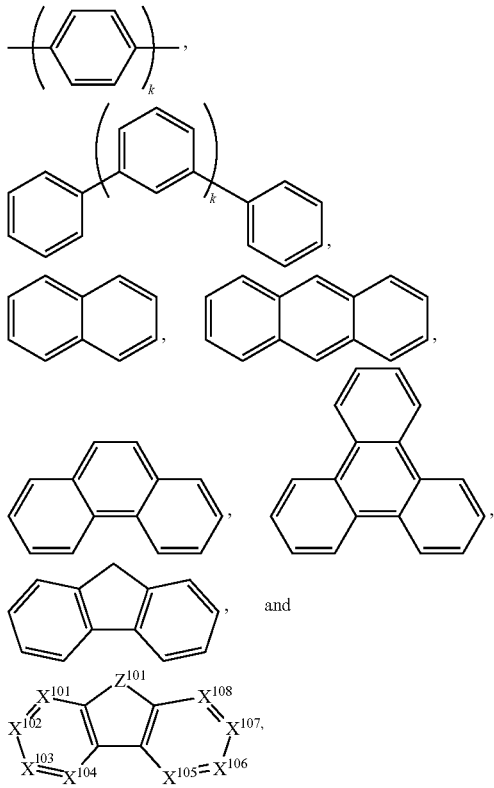

wherein k is an integer from 1 to 20; $X^{101}$ to $X^{108}$ is C (including CH) or N; $Z^{101}$ is $NAr^1$, O, or S; $Ar^1$ has the same group defined above.

Examples of metal complexes used in HIL or HTL include, but are not limited to the following general formula:

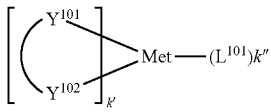

wherein Met is a metal, which can have an atomic weight greater than 40; $(Y^{101}\text{-}Y^{102})$ is a bidentate ligand, $Y^{101}$ and $Y^{102}$ are independently selected from C, N, O, P, and S; $L^{101}$ is an ancillary ligand; k' is an integer value from 1 to the maximum number of ligands that may be attached to the metal; and k'+k" is the maximum number of ligands that may be attached to the metal.

In one aspect, $(Y^{101}\text{-}Y^{102})$ is a 2-phenylpyridine derivative. In another aspect, $(Y^{101}\text{-}Y^{102})$ is a carbene ligand. In another aspect, Met is selected from Ir, Pt, Os, and Zn. In a further aspect, the metal complex has a smallest oxidation potential in solution vs. Fc⁺/Fc couple less than about 0.6 V.

EBL:

An electron blocking layer (EBL) may be used to reduce the number of electrons and/or excitons that leave the emissive layer. The presence of such a blocking layer in a device may result in substantially higher efficiencies, and or longer lifetime, as compared to a similar device lacking a blocking layer. Also, a blocking layer may be used to confine emission to a desired region of an OLED. In some embodiments, the EBL material has a higher LUMO (closer to the vacuum level) and or higher triplet energy than the emitter closest to the EBL interface. In some embodiments, the EBL material has a higher LUMO (closer to the vacuum level) and or higher triplet energy than one or more of the hosts closest to the EBL interface. In one aspect, compound used in EBL contains the same molecule or the same functional groups used as one of the hosts described below.

Host:

The light emitting layer of the organic EL device of the present invention preferably contains at least a metal complex as light emitting material, and may contain a host material using the metal complex as a dopant material. In some embodiments, two or more hosts are preferred. In some embodiments, the hosts used maybe a) bipolar, b) electron transporting, c) hole transporting or d) wide band gap materials that play little role in charge transport. Examples of the host material are not particularly limited, and any metal complexes or organic compounds may be used as long as the triplet energy of the host is larger than that of the dopant. While the Table below categorizes host materials as preferred for devices that emit various colors, any host material may be used with any dopant so long as the triplet criteria is satisfied.

Examples of metal complexes used as host are preferred to have the following general formula:

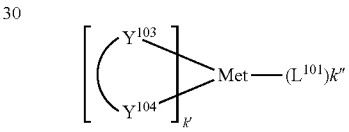

wherein Met is a metal; $(Y^{103}\text{-}Y^{104})$ is a bidentate ligand, $Y^{103}$ and $Y^{104}$ are independently selected from C, N, O, P, and S; $L^{101}$ is an another ligand; k' is an integer value from 1 to the maximum number of ligands that may be attached to the metal; and k'+k" is the maximum number of ligands that may be attached to the metal.

In one aspect, the metal complexes are:

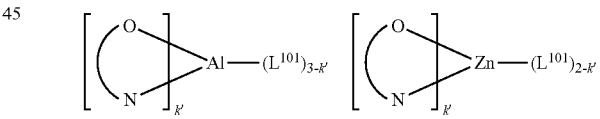

wherein (O—N) is a bidentate ligand, having metal coordinated to atoms O and N.

In another aspect, Met is selected from Ir and Pt. In a further aspect, $(Y^{103}Y^{104})$ is a carbene ligand.

Examples of organic compounds used as host are selected from the group consisting of aromatic hydrocarbon cyclic compounds such as benzene, biphenyl, triphenyl, triphenylene, naphthalene, anthracene, phenalene, phenanthrene, fluorene, pyrene, chrysene, perylene, and azulene; the group consisting of aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and the group consisting of 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each group is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, the host compound contains at least one of the following groups in the molecule:

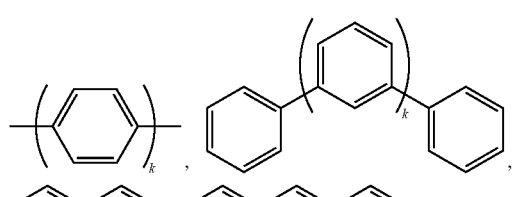
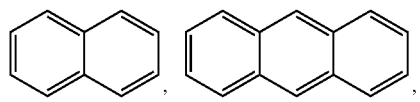
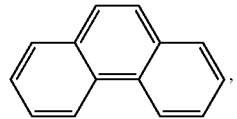
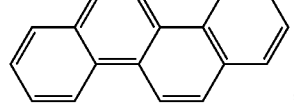
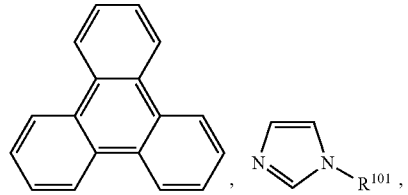
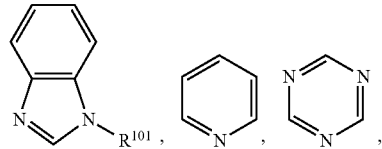
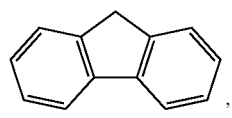
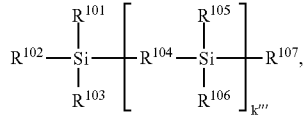

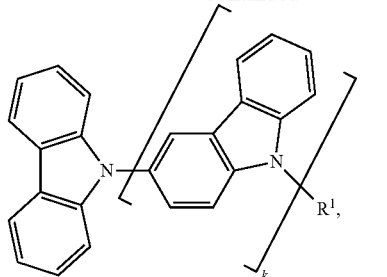
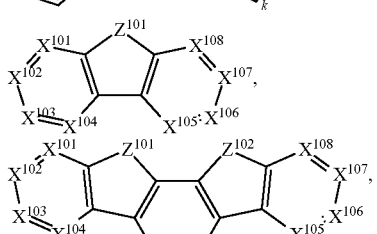
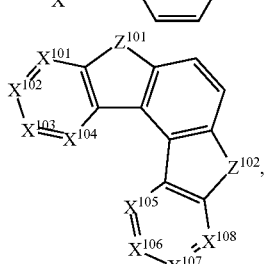
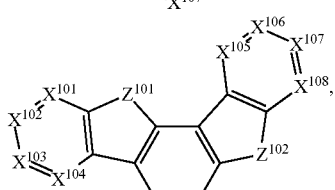
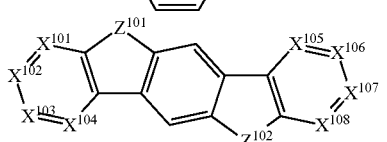
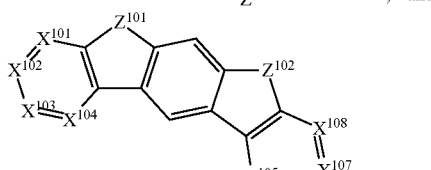

, and wherein $R^{101}$ to $R^{107}$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above. k is an integer from 0 to 20 or 1 to 20; k''' is an integer from 0 to 20. $X^{101}$ to $X^{108}$ is selected from C (including CH) or N.
$Z^{101}$ and $Z^{102}$ is selected from $NR^{101}$, O, or S.

HBL:

A hole blocking layer (HBL) may be used to reduce the number of holes and/or excitons that leave the emissive layer. The presence of such a blocking layer in a device may result in substantially higher efficiencies and/or lifetime as compared to a similar device lacking a blocking layer. Also, a blocking layer may be used to confine emission to a desired region of an OLED. In some embodiments, the HBL material has a lower HOMO and or higher triplet energy than the emitter closest to the HBL interface.

In one aspect, compound used in HBL contains the same molecule or the same functional groups used as host described above.

In another aspect, compound used in HBL contains at least one of the following groups in the molecule:

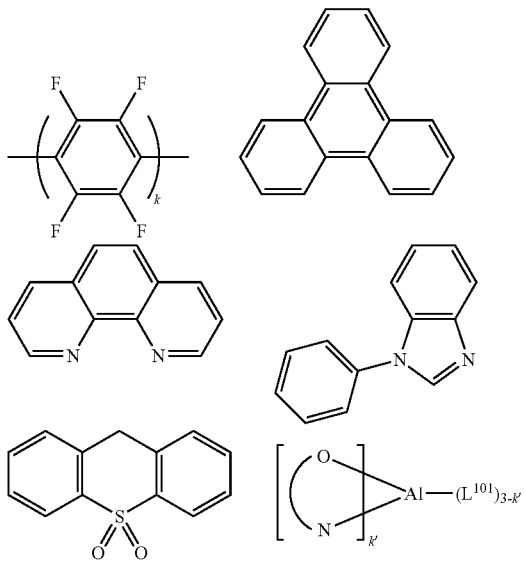

wherein k is an integer from 1 to 20; $L^{101}$ is an another ligand, k' is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

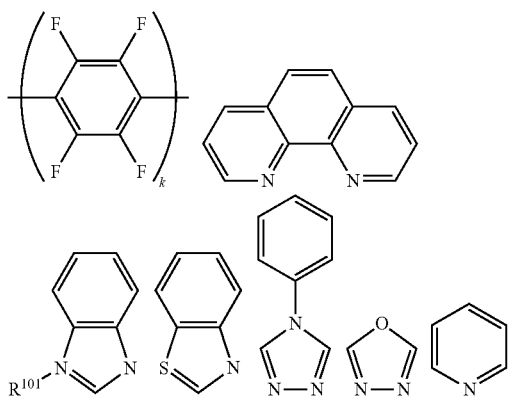

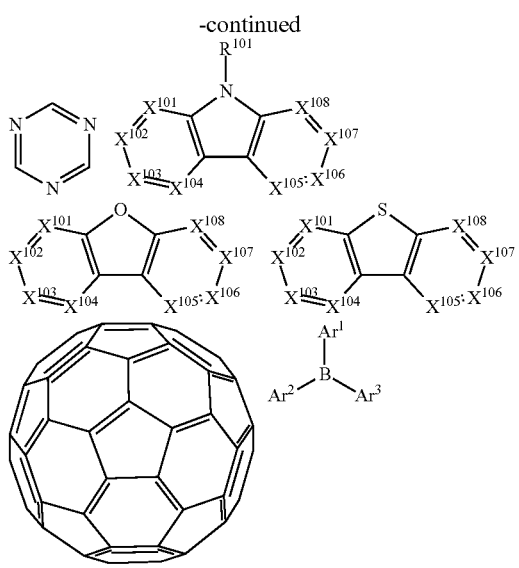

wherein $R^{101}$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above. $A^1$ to $Ar^3$ has the similar definition as Ar's mentioned above. k is an integer from 1 to 20. $X^{101}$ to $X^{108}$ is selected from C (including CH) or N.

In another aspect, the metal complexes used in ETL include, but are not limited to the following general formula:

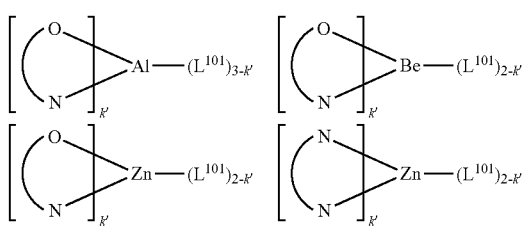

wherein (O—N) or (N—N) is a bidentate ligand, having metal coordinated to atoms O, N or N, N; $L^{101}$ is another ligand; k' is an integer value from 1 to the maximum number of ligands that may be attached to the metal.

Charge Generation Layer (CGL):

In tandem or stacked OLEDs, the CGL plays an essential role in the performance, which is composed of an n-doped layer and a p-doped layer for injection of electrons and holes, respectively. Electrons and holes are supplied from the CGL and electrodes. The consumed electrons and holes in the CGL are refilled by the electrons and holes injected from the cathode and anode, respectively; then, the bipolar currents reach a steady state gradually. Typical CGL materials include n and p conductivity dopants used in the transport layers.

In any above-mentioned compounds used in each layer of the OLED device, the hydrogen atoms can be partially or fully deuterated. Thus, any specifically listed substituent, such as, without limitation, methyl, phenyl, pyridyl, etc. encompasses undeuterated, partially deuterated, and fully deuterated versions thereof. Similarly, classes of substituents such as, without limitation, alkyl, aryl, cycloalkyl, heteroaryl, etc. also encompass undeuterated, partially deuterated, and fully deuterated versions thereof.

The invention is explained in greater detail by the following examples, without wishing to restrict it thereby. The person skilled in the art will be able to produce further electronic devices on the basis of the descriptions without inventive step and will thus be able to carry out the invention throughout the range claimed.

EXAMPLES

The devices in Tables 1 were fabricated in high vacuum (<$10^{-6}$ Torr) by thermal evaporation. The anode electrode was ~800 Å of indium tin oxide (ITO). 10 Å of LiF was used as the electron injection layer (EIL) followed by a cathode of 1,000 Å of Al. All devices were encapsulated with a glass lid sealed with an epoxy resin in a nitrogen glove box (<1 ppm of $H_2O$ and $O_2$,) immediately after fabrication, and a moisture getter was incorporated inside the package. The device examples had organic stacks consisting of, sequentially, from the ITO surface, 100 Å thick HAT-CN hole injection layer (HIL), 250 Å layer of Compound A (HTL), 300 Å of blue emissive layer (EML) using Compound B as the host doped with 20% of blue emitter. Each device also consisted of a 50 Å blocking layer of Compound C (BL) and ~400 Å of a tris-(8-hydroxyquinoline) aluminum ($Alq_3$) electron transporting layer (ETL).

The OLED device structures should be optimized for outcoupling the light emitted by the blue emitting compound. Maximizing the outcoupling requires the preferred HTL and ETL layer thicknesses. The preferred EML to anode or cathode distance is $\lambda/(2*n)*(m-\phi/\pi)$ where m is an integer. (m=1,2,3,4,5), n is the refractive index of the organic between the EML and the contact, $\lambda$ is the wavelength of the emitter in free space, and $\phi$ is the phase shift of reflections at the organic-contact interface. For typical OLED contact materials $\phi$~ranges between 1.8-2.8.

TABLE 1

Device Results.

| | 1931 CIE | | $\lambda$ max | FWHM | Voltage | At 10 mA/cm² | | calc* | calc* | Lo | At 20 mA/cm² | | | At 1 mA/cm² |
| | | | | | | | EQE | 95% | 80% | | $LT_{97\%}$ | $LT_{95\%}$ | $LT_{80\%}$ | EQE |
| Emitter | x | y | [nm] | [nm] | [V] | LE [cd/A] | [%] | [h] | [h] | [nits] | [h] | [h] | [h] | [%] |
|---|---|---|---|---|---|---|---|---|---|---|---|---|---|---|
| Comparative Compound 2 | 0.151 | 0.227 | 462 | 50 | 5.5 | 19.9 | 12.5 | 14 | 102 | 3,750 | 1 | 1 | 9 | 13.8 |
| Comparative Compound 1 | 0.153 | 0.217 | 460 | 53 | 6.2 | 5.2 | 3.4 | 3 | 31 | 1,002 | 2 | 3 | 31 | 3.6 |
| Comparative Compound 6 | 0.143 | 0.210 | 463 | 47 | 5.3 | 15.7 | 10.5 | 2 | 12 | 2,977 | 0 | 0 | 2 | 11.5 |
| Ir(LA5)3 | 0.148 | 0.247 | 466 | 48 | 5.3 | 10.7 | 6.4 | 31 | 341 | 2,090 | 3 | 8 | 90 | 6.7 |

TABLE 2

PLQY in PMMA, PL transient in frozen glass of phenanthradine emitter complexes, and single exponential fit to room temperature PL transient in PMMA

| Emitter | PLQY in PMMA (5%) [%] | Frozen glass transient (77 K) (μs) | Room temp. transient in PMMA (5%) Single exponential fit (μs) | Comments |
|---|---|---|---|---|
| Comparative Compound 2 | 67 | 3.12 | | Reference complex |
| Comparative Compound 1 | 31 | 5.64 | 2.38 | Reference complex |
| Comparative Compound 6 | 72 | 3.58 | 2.37 | Reference complex |
| Ir(LA5)3 | 33 | 2.81 | 1.34 | |
| Compound 49 | 62 | 2.87 | | |
| Ir[Compound (1-35)]3 | 31 | 2.84 | 1.72 | |
| Ir[Compound (1-137)][L14]2 | 61 | | | Heteroleptic |
| Ir(LA5)(L14)2 | 30 | 4.89 | | Heteroleptic |

TABLE 3
Names and molecular structures of compounds used in OLED structures.
Compound A
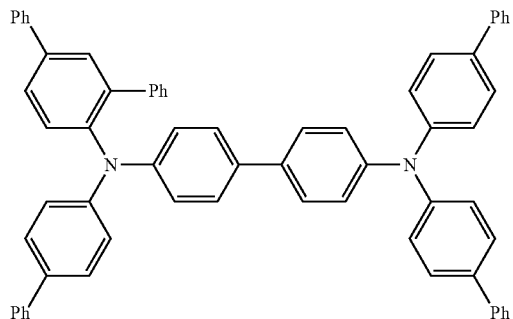 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5-c5ccccc5)cc4)cc3)cc2)cc1]
Compound B
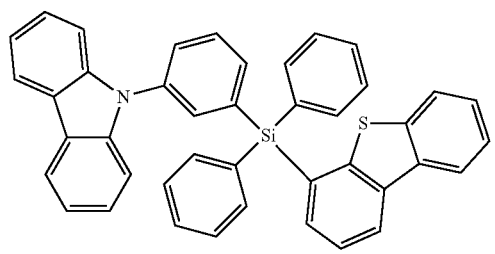 [SMILES: c1ccc([Si](c2ccccc2)(c2cccc(-n3c4ccccc4c4ccccc43)c2)c2cccc3c2sc2ccccc23)cc1]
Compound C
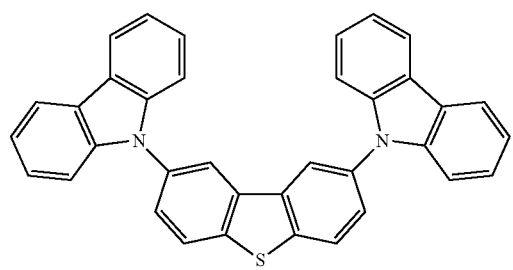 [SMILES: c1ccc2c(c1)c1ccccc1n2-c1ccc2sc3ccc(-n4c5ccccc5c5ccccc54)cc3c2c1]
Comparative Compound 1
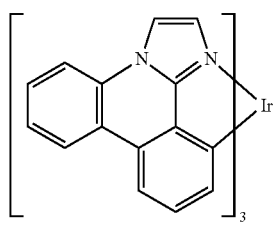
Comparative Compound 2
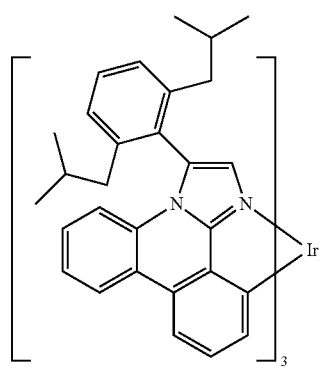

TABLE 3-continued
Names and molecular structures of compounds used in OLED structures.
Comparative Compound 6
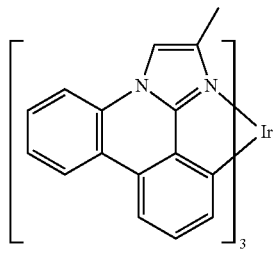
Ir(LA5)$_3$
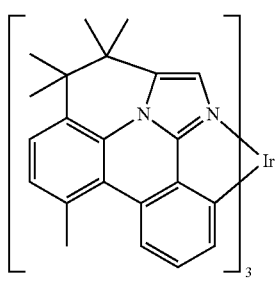
Compound 49
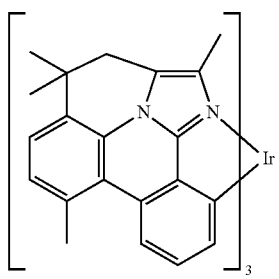
Ir[Compound (1-35)]$_3$
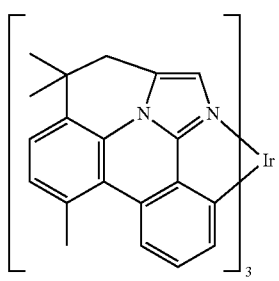
Ir[Compound (1-137)][L14]$_2$
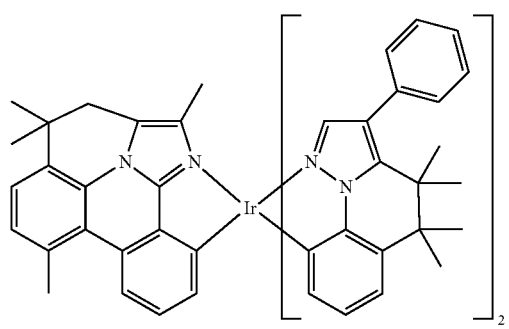

TABLE 3-continued

Names and molecular structures of compounds used in OLED structures.

Ir(LA5)(L14)$_2$

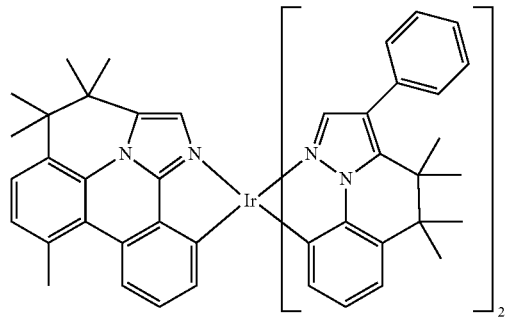

AlQ3

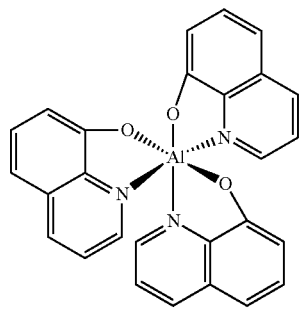

HAT-CN

When an electron and hole localize on the same molecule, an "exciton," which is a localized electron-hole pair having an excited energy state, is formed. Light is emitted when the exciton relaxes via a photoemissive mechanism. Non-radiative mechanisms which lower the PLQY of the emitter are generally considered undesirable. However, in this invention we use these generally undesirable non-radiative mechanisms to improve device lifetime at the expense of efficiency. A number of non-radiative mechanisms can be present for an emitter in an organic layer in an OLED device. They include but are not limited to thermal relaxation, self-quenching, and energy transfer to a non-emissive species.

Without being bound by theory, understanding the advantages of using an emitter with the typically undesirable non-radiative decay mechanisms begins with the decay rate constants of the light emitting material.

$$k_{observed} = k_{rad} + k_{non-rad} \quad (1)$$

where $k_{rad}$ is the sum of all the radiative processes and $k_{non-rad}$ is the sum of all the non-radiative processes. To be explict, $k_{non-rad}$ can be the sum of many different non-radiative decay processes. The observed rate constant is more typically reported as the transient time ($\tau_{observed}$) which is often called the photoluminescent transient (PL transient), where:

$$\tau_{observed} = \frac{1}{k_{observed}} = \frac{1}{k_{rad} + k_{non-rad}} \quad (2)$$

For any emitter the Quantum Yield (QY) of photons can be expressed as the ratio of the total radiative and total non-radiative decay rate constants and is explicitly defined as the number of photons emitted per excited state:

$$QY = \frac{k_{rad}}{k_{rad} + k_{non-rad}} \quad (3)$$

Using equations 1-3 we can outline three relevant regimes of operation. The first is when $k_{rad}$ is $\gg k_{non-rad}$. In this regime QY approaches 1 (100%) and $\tau_{observed} \approx 1/k_{rad} = \tau_0$ where $\tau_0$ is the intrinsic decay time of the emitter. The emitter has a quantum yield of unity and the observed decay rate is intrinsic to the molecule and equal to $\tau_0$. In a second regime of operation $k_{rad}$ is $\ll k_{non-rad}$. In this regime QY and $\tau_{observed}$ go to zero. In the third regime of operation $k_{rad}$ is $\sim k_{non-rad}$. In this regime $0.01 \ll QY < 1$ and an observed decay time less than $\tau_0$.

Conventional wisdom regarding designing OLED emitting molecules would be have the highest QY possible (or operating in regime 1). In this case the decay time of the emitter is $\tau_0$. However, if we were to increase the non-radiative decay rate constant to be exactly equal to the radative decay rate constant ($k_{rad} = k_{non-rad}$) then we would have a QY of 0.5 and an observed decay time $\tau = \tau_0/2$.

The loss in luminance of an OLED device can be attributed to the formation of quenchers from the emitting molecule. In a simple kinetic model for the formation of quenchers, the formation rate is proportional to the population of emitters in the excited state and the formation rate constant. From above, we know that the concentration of emitters in the excited state is exponentially dependent on $k_{observed}$ ($1/\tau$) and will be significantly reduced by having $k_{rad} = k_{non-rad}$. Thus, designing the non-radiative decay rate constant to be on the order of the radiative rate constant should decrease the rate of formation of quenchers and improve the stability of OLED devices. The increase in stability should occur even though the emitter will have a lower QY and the corresponding device will have a lower EQE. One knowledgable in the art would typically teach against lowering the EQE of an OLED device (through lowering the QY of an emitter) because the device will require more current to reach the same luminance. Driving an OLED device at higher current densities has been shown to increase the degradation of OLED devices. The degradation of an OLED device versus current density is a power law with a value between 1.0-2.0. However, by changing $k_{non-rad}$ the decrease in concentration due to increasing $k_{observed}$ is exponential. Thus, there can be net gain in stability for an OLED device through modification of the non-radative decay rate constant.

With inventative example Ir(LA5)3 we observe the effect of building the non-radiative decay mechanism directly into the molecule. Ir(LA5)3 has a lower PLQY than comparative compounds 1, 2 and 6, see Table 2. In the OLED devices this lower PLQY translate to lower EQE at 1 mA/cm², see Table 1. However, the LT80 at 20 mA/cm² and also LT80 @ 1,000 nits is significantly improved over comparative compounds 1, 2, and 6.

There are various phenomena that can contribute to $k_{non-rad}$. We outline several here. The first is thermal relaxation which is generally considered intrinsic to the emitter's chemical structure. A second non-radiative pathway in OLED devices is self quenching which occurs at high doping concentrations. In some embodiments the doping concentration should be between 0.1 to 40% by volume. In some embodiments the doping concentration should be between 5 to 40% by volume. In some embodiments the doping concentration should be between 15 to 40% by volume. A third method for increasing the non-radiative decay rate constant is to introduce a non-emissive species which accepts energy from the emitter molecule and lowers the QY of the emitter. In some embodiments the OLED device should have a non-emissive species which quenches the emitter molecule doped into the same layer as the emitter molecule at a concentration between 0.01 to 10% by volume. A fourth method for increasing the non-radiative decay rate constant is to design the EML to increase triplet-charge and triplet-triplet interactions which annihilate triplet excitons on the emitter molecule.

We note that this principal is general and applies to many classes of emitting molecules. However, this idea is most applicable to emitters where the triplet exciton is emitted as light as these emitters have the longest decay times. These systems include but are not limited to phosphors and TADF molecules. Some aspects of the rate limiting steps in TADF molecules are important. First, the rate limiting step in $k_{rad}$ is the reverse intersystem crossing time which typically is on the order of 1E6 1/s. Second, if $k_{non-rad}$ is increased for either the singlet or triplet state the QY will be lowered and the concentration of the respective species will be lowered (singlets for increase $k_{non-rad}$ for singlets and triplets for $k_{non-rad}$ of triplets). If we assume that triplet excitons of TADF molecules are the source of quenchers and increase the non-radiative decay rate constant for triplet excitons then the increase in stability is expect as outlined above. However, the observed decay time as measured by PL transient will not be decreased as the rate limiting step is reverse intersystem crossing and not affected by the increase in $k_{non-rad}$. However, if the decay of the triplet population were observed directly, as is possible with a technique like transient absorption spectroscopy, then the observed decay time would be increased and the steady state population would be decreased. If singlet excitons are the source of quenchers in TADF OLED devices, then the modification of $k_{non-rad}$ of the singlet exciton is required to achieve an increase in the stability of the OLED device. Again, the observed PL transient would not be increased as the rate limiting step is reverse intersystem crossing from the triplet state.

It will be appreciated by those skilled in the art that changes could be made to the exemplary embodiments shown and described above without departing from the broad inventive concept thereof. It is understood, therefore, that this invention is not limited to the exemplary embodiments shown and described, but it is intended to cover modifications within the spirit and scope of the present invention as defined by the claims. For example, specific features of the exemplary embodiments may or may not be part of the claimed invention and features of the disclosed embodiments may be combined. Unless specifically set forth herein, the terms "a", "an" and "the" are not limited to one element but instead should be read as meaning "at least one".

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Further, to the extent that any methods of the present invention do not rely on the particular order of steps set forth herein, the particular order of the steps should not be construed as limitation on the claims. The claims directed to such methods should not be limited to the performance of their steps in the order written, and one skilled in the art can readily appreciate that the steps may be varied and still remain within the spirit and scope of the present invention.

All references, including publications, patent applications, and patents, cited herein are hereby incorporated by reference to the same extent as if each reference were individually and specifically indicated to be incorporated by reference and were set forth in its entirety herein.

We claim:
1. An organic light emitting device (OLED) comprising:
an anode;
a cathode; and
an emission layer, disposed between the anode and the cathode, comprising a first emitting compound;
wherein the first emitting compound is capable of functioning as a blue phosphorescent emitter in the OLED at room temperature;
wherein the first emitting compound has PLQY of less than 90% at room temperature;
wherein the OLED has an external quantum efficiency of between 8% and 20% at 1 mA/cm²;

wherein the first emitting compound has a structure of M(L$^1$)$_x$(L$^2$)$_y$(L$^3$)$_z$, wherein L$^1$ has the structure

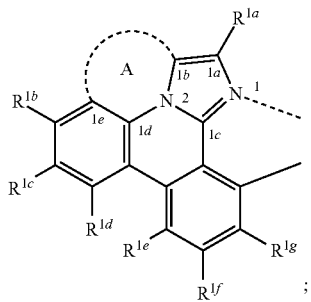

wherein L$^1$, L$^2$ and L$^3$ can be the same or different;

wherein x is 1, 2, or 3;

wherein y is 0, 1, or 2;

wherein z is 0, 1, or 2;

wherein x+y+z is the oxidation state of the metal M;

wherein M is a metal having an atomic weight greater than 40;

wherein A is a linking group selected from the group consisting of —CR'R"—CR'R"—, —CR'R'—CR"R"—, —CH$_2$—CH$_2$—, —CR'R'—CR'R'—CR'R'—, —CR'R"—NR'—, —CR'=CR'—CR'R'—, —O—SiR'R'—, —CR'R"—S—, —CR'R"—O—, and —CR'R"—SiR'R'—;

wherein each R' is independently selected from the group consisting of H, alkyl, phenyl and substituted phenyl;

wherein each R" is independently selected from the group consisting of alkyl, phenyl and substituted phenyl;

wherein R's and R"s are optionally connected to form a saturated five membered ring or a saturated six membered ring, and combinations thereof;

wherein R$^{1a}$ to R$^{1g}$ are each independently selected from the group consisting of hydrogen, deuterium, alkyl, cycloalkyl, heteroalkyl, alkoxy, aryloxy, amino, silyl, alkenyl, cycloalkenyl, heteroalkenyl, alkynyl, arylalkyl, CN, CF$_3$, CO$_2$R, C(O)R, C(O)NR$_2$, NR$_2$, NO$_2$, OR, SR, SO$_2$, SOR, SO$_3$R, halo, aryl, heteroaryl, a heterocyclic group, and combinations thereof;

wherein each R is independently selected from the group consisting of hydrogen, deuterium, halo, alkyl, cycloalkyl, heteroalkyl, alkoxy, aryloxy, amino, silyl, alkenyl, cycloalkenyl, heteroalkenyl, alkynyl, aralkyl, aryl, heteroaryl, and combinations thereof; and wherein any one of the ring atoms to which R$^{1b}$ to R$^{1g}$ are attached may be replaced with a nitrogen atom, wherein when the ring atom is replaced with a nitrogen atom the corresponding R group is not present.

2. The OLED of claim 1, wherein the first emitting compound is capable of emitting light from a triplet excited state to a ground singlet state at room temperature.

3. The OLED of claim 1, wherein the first emitting compound is a metal coordination complex having a metal-carbon bond.

4. The OLED of claim 3, wherein the metal is selected from the group consisting of Ir, Rh, Re, Ru, Os, Pt, Au, and Cu.

5. The OLED of claim 1, wherein L$^2$ and L$^3$ are each independently selected from the group consisting of;

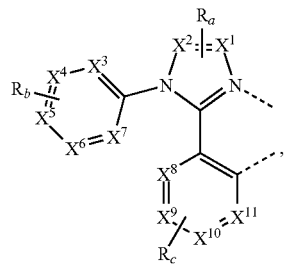

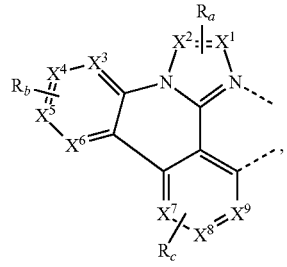

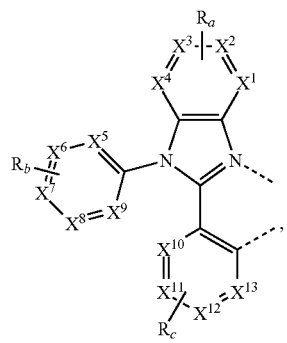

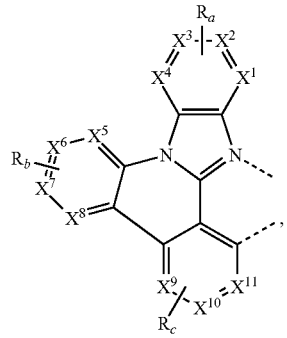

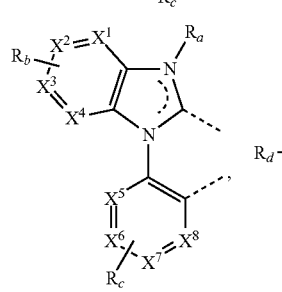

-continued

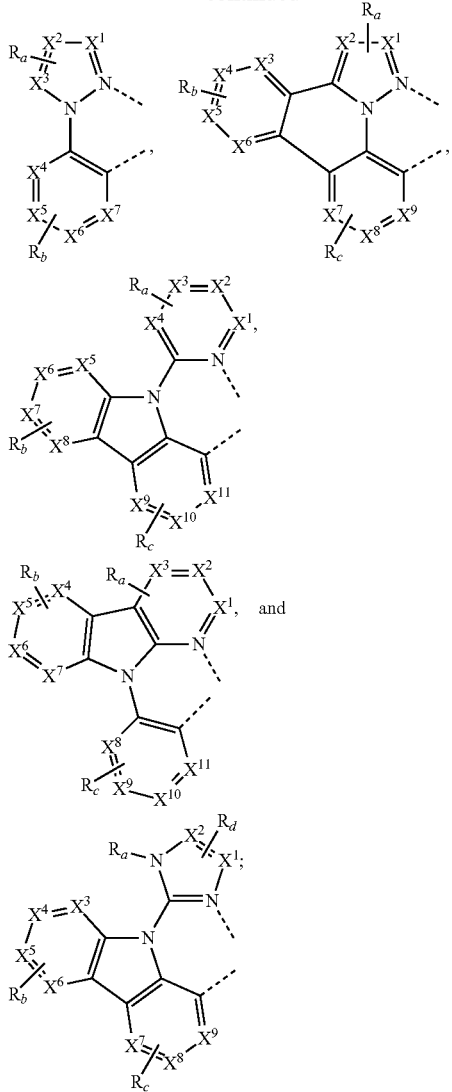

wherein each $X^1$ to $X^{13}$ are independently selected from the group consisting of carbon and nitrogen;
wherein X is selected from the group consisting of BR', NR', PR', O, S, Se, C=O, S=O, SO$_2$, CR'R", SiR'R", and GeR'R";
wherein R' and R" are optionally fused or joined to form a ring;
wherein each $R_a$, $R_b$, $R_c$, and $R_d$ may represent from mono substitution to the possible maximum number of substitution, or no substitution;
wherein R', R", $R_a$, $R_b$, $R_c$, and $R_d$ are each independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and
wherein any two adjacent substituents of $R_a$, $R_b$, $R_c$, and $R_d$ are optionally fused or joined to form a ring or form a multidentate ligand.

6. The OLED of claim 1, wherein the OLED has a performance lifetime of at least 30 hours to 80% of the initial luminance at room temperature under a constant driving current of 20 mA/cm$^2$.

7. The OLED of claim 1, wherein the first emitting compound has a first triplet energy less than 500 nanometers.

8. The OLED of claim 1, wherein the first emitting compound emits light having a CIE x-coordinate less than 0.25 and a CIE y-coordinate less than 0.4.

9. The OLED of claim 1, wherein the first emitting compound has less than 2 microsecond of the fastest component of its photoluminescence transient that fits to a multiple exponential function at room temperature under inert atmosphere.

10. The OLED of claim 1, wherein the first emitting compound has PLQY of less than 80% at room temperature.

11. The OLED of claim 1, wherein the OLED has an external quantum efficiency of between 8% and 18% at 1 mA/cm$^2$.

12. The OLED of claim 5, wherein the M is selected from the group consisting of Ir, Rh, Re, Ru, Os, Pt, Au, and Cu.

13. The OLED of claim/wherein $L^2$ and $L^3$ are each independently selected from the group consisting of:

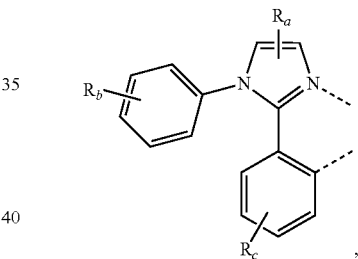

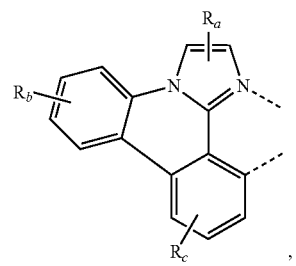

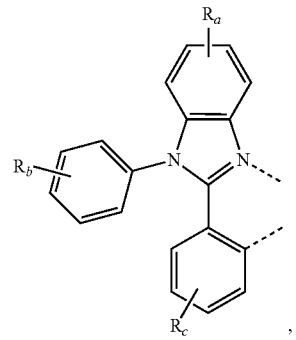

-continued

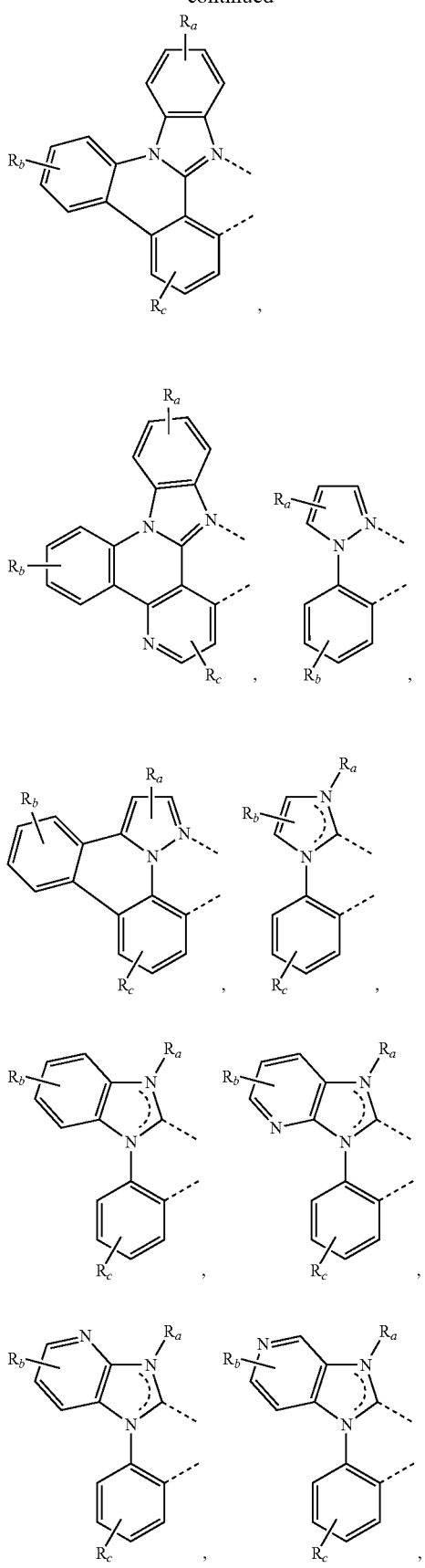

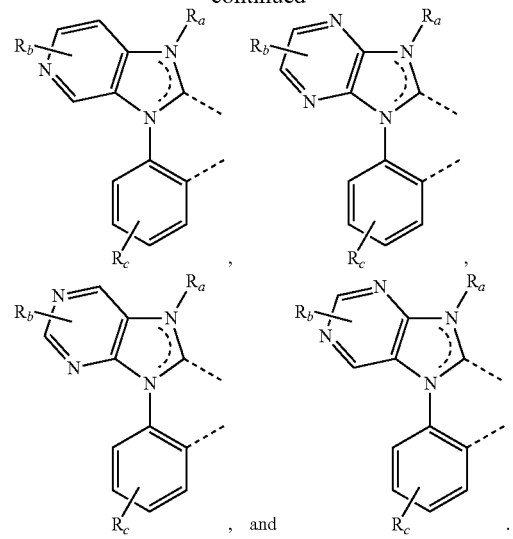

, and

14. The OLED of claim 5, wherein the first emitting compound has the formula of $Pt(L^1)_2$ or $Pt(L^1)(L^2)$.

15. The OLED of claim 1, wherein the first emitting compound has a structure of Formula 2:

Formula 2

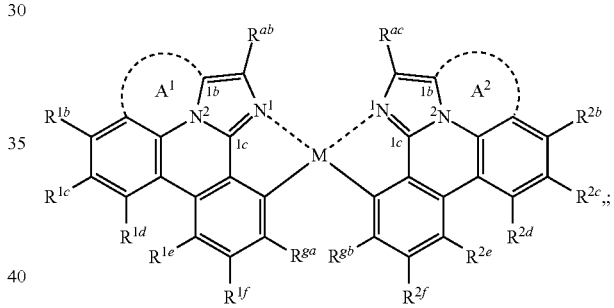

wherein M is Pt;
wherein $A^1$ and $A^2$ are each independently a first linking group independently selected from the group consisting of —CR'R"—CR'R"—, —CR'R'—CR"R"—, —CH$_2$—CH$_2$—, —CR'R'—CR'R'—CR'R'—, —CR'R"—NR'—, —CR'=CR'—CR'R'—, —O—SiR'R'—, —CR'R"—S—, —CR'R"—O—, and —CR'R"—SiR'R'—;
wherein each R' is independently selected from the group consisting of H, alkyl, phenyl and substituted phenyl;
wherein each R" is independently selected from the group consisting of alkyl, phenyl and substituted phenyl;
wherein R's and R"s are optionally connected to form a saturated five membered ring or a saturated six membered ring, and combinations thereof;
wherein $R^{1b}$ to $R^{1f}$ and $R^{2b}$ to $R^{2f}$ are each independently selected from the group consisting of hydrogen, deuterium, alkyl, cycloalkyl, heteroalkyl, alkoxy, aryloxy, amino, silyl, alkenyl, cycloalkenyl, heteroalkenyl, alkynyl, aralkyl, CN, CF$_3$, CO$_2$R, C(O)R, C(O)NR$_2$, NR$_2$, NO$_2$, OR, SR, SO$_2$, SOR, SO$_3$R, halo, aryl, heteroaryl, a heterocyclic group, and combinations thereof;
wherein any one of the ring atoms to which $R^{1b}$ to $R^{1f}$ and $R^{2b}$ to $R^{2f}$ are attached may be replaced with a nitrogen atom, wherein when the ring atom is replaced with a nitrogen atom the corresponding R group is not present; and wherein $R^{ab}$ and $R^{ac}$ and/or $R^{ga}$ and $R^{gb}$ may bond to form a second linking group having one to three linking atoms each independently selected from the group consisting of B, N, P, O, S, Se, C, Si, Ge or combinations thereof.

16. The OLED of claim 1, wherein the OLED is incorporated into a device selected from the group consisting of a consumer product, an electronic component module, and a lighting panel.

17. The OLED of claim 5, wherein the first emitting compound has a structure $(L_A)_nML_m$ according to Formula 1:

Formula 1

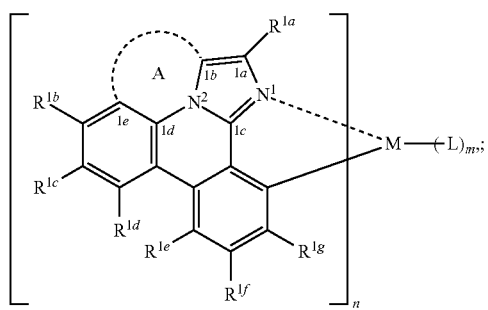

wherein $R^{1a}$ to $R^{1g}$ are each independently selected from the group consisting of hydrogen, deuterium, alkyl, cycloalkyl, heteroalkyl, alkoxy, aryloxy, amino, silyl, alkenyl, cycloalkenyl, heteroalkenyl, alkynyl, aralkyl, CN, $CF_3$, $CO_2R$, C(O)R, $C(O)NR_2$, $NR_2$, $NO_2$, OR, SR, $SO_2$, SOR, $SO_3R$, halo, aryl, heteroaryl, a heterocyclic group, and combinations thereof;

wherein each R is independently selected from the group consisting of hydrogen, deuterium, halo, alkyl, cycloalkyl, heteroalkyl, alkoxy, aryloxy, amino, silyl, alkenyl, cycloalkenyl, heteroalkenyl, alkynyl, aralkyl, aryl, heteroaryl, and combinations thereof;

wherein any one of the ring atoms to which $R^{1b}$ to $R^{1g}$ are attached may be replaced with a nitrogen atom, wherein when the ring atom is replaced with a nitrogen atom the corresponding R group is not present; and wherein L is a substituted or unsubstituted cyclometallated ligand.

18. The OLED of claim 17, wherein the first emitting compound has Formula 3:

Formula 3

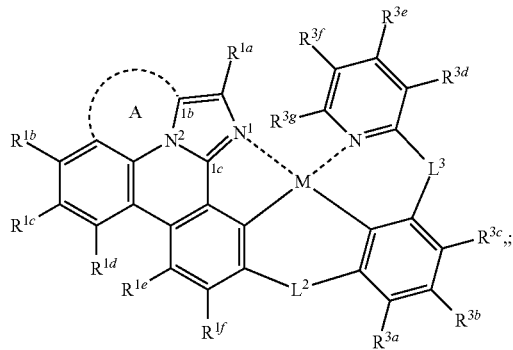

wherein M is Pt;

wherein $L^2$ and $L^3$ are each independently selected from the group consisting of a single bond, BR, NR, PR, O, S, Se, C—O, S—O, $SO_2$, $CR^1R^2$, $SiR^1R^2$, and $GeR^1R^2$;

wherein $R^{3a}$-$R^{3f}$, are each independently selected from the group consisting of hydrogen, deuterium, alkyl, cycloalkyl, heteroalkyl, alkoxy, aryloxy, amino, silyl, alkenyl, cycloalkenyl, heteroalkenyl, alkynyl, aralkyl, CN, $CF_3$, $CO_2R$, C(O)R, $C(O)NR_2$, $NR_2$, $NO_2$, OR, SR, $SO_2$, SOR, $SO_3R$, halo, aryl, heteroaryl, a heterocyclic group, and combinations thereof;

wherein any two adjacent $R^{1f}$, $R^{3a}$, $R^{3c}$, $R^{3d}$, $R^1$ and $R^2$ are optionally joined to form a ring; wherein $L^2$ and $R^{1f}$, $L^2$ and $R^{3a}$, or $L^2$ and both $R^{1f}$ and $R^{3a}$ are optionally joined to form one or more rings; and wherein $L^3$ and $R^{3c}$, $L^3$ and $R^{3d}$, or $L^3$ and both $R^{3c}$ and $R^{3d}$ are optionally joined to form one or more rings.

19. The OLED of claim 1, wherein is selected from the group consisting of

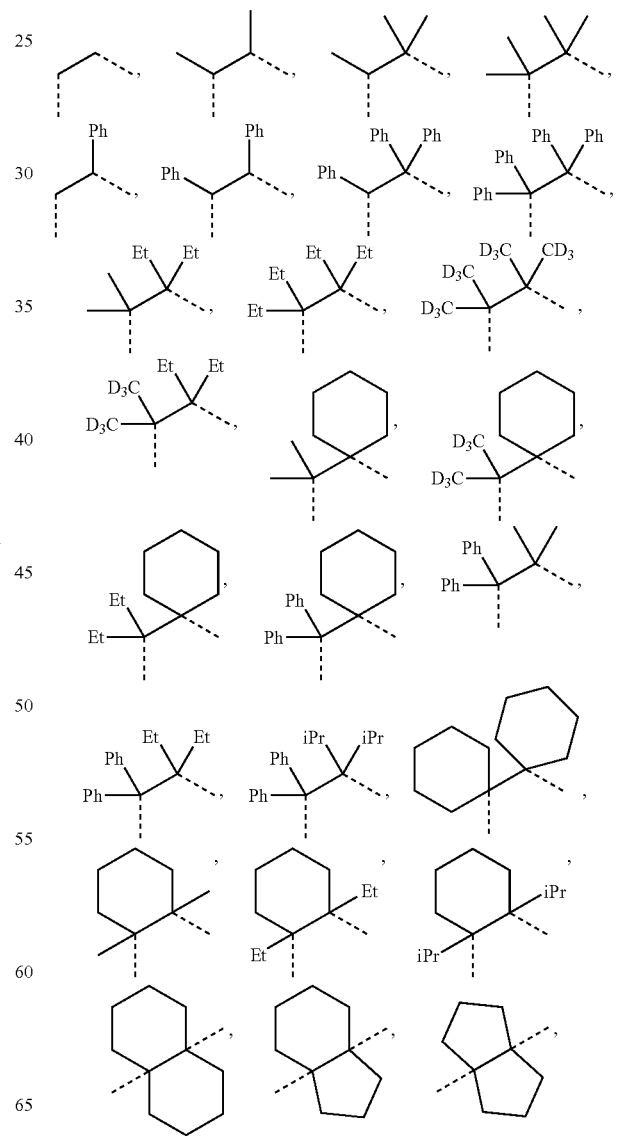

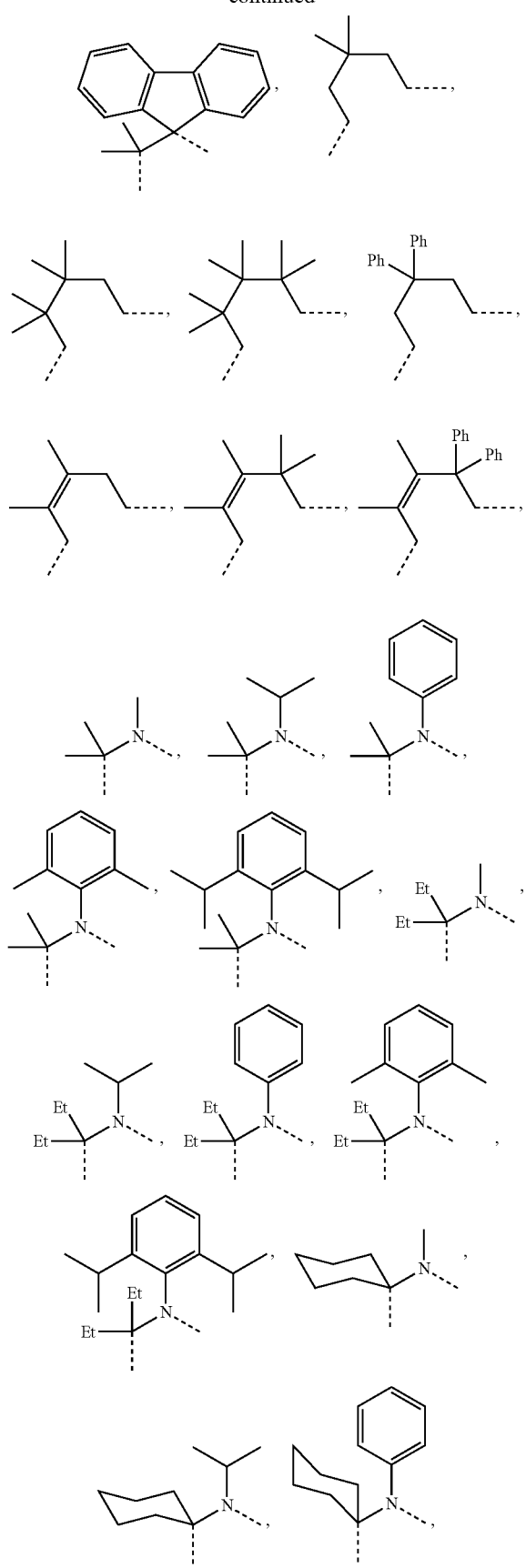
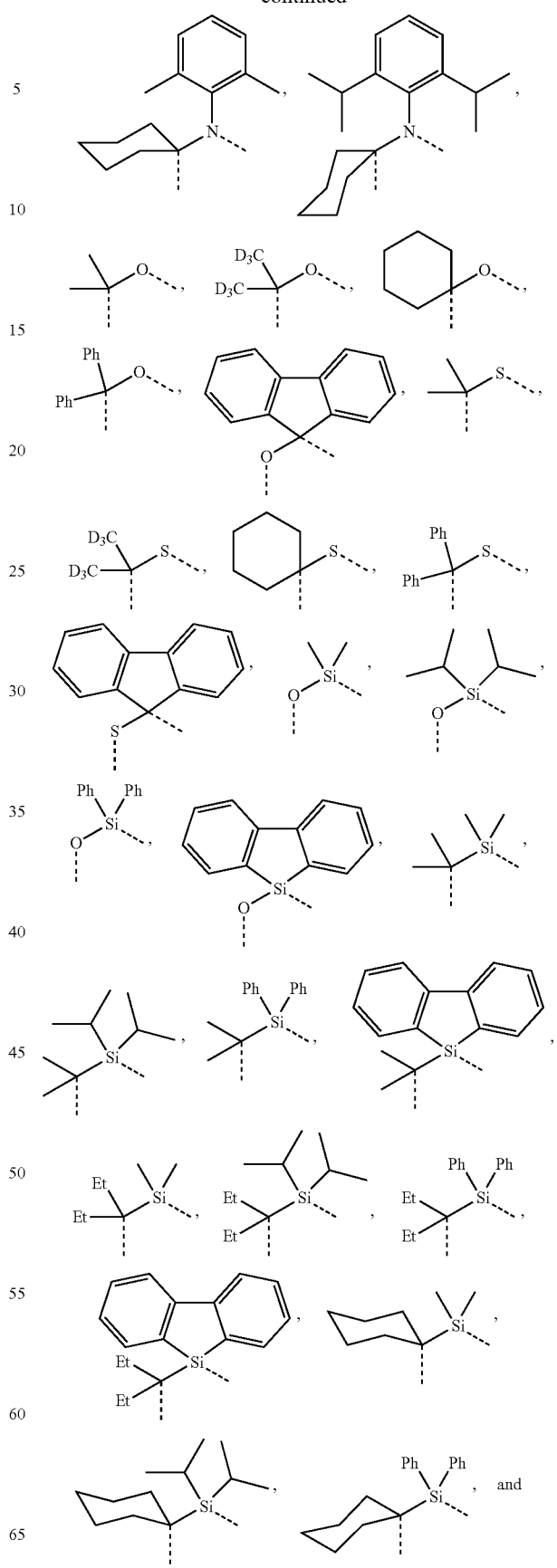

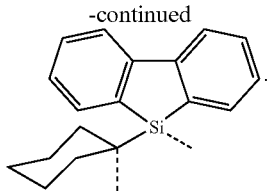
* * * * *